United States Patent [19]

Kawai et al.

[11] Patent Number: 5,387,671

[45] Date of Patent: * Feb. 7, 1995

[54] HEXA- AND HEPTAPEPTIDE ANAPHYLATOXIN-RECEPTOR LIGANDS

[75] Inventors: Megumi Kawai; Paul Wiedeman; Jay R. Luly; Yat S. Or, all of Libertyville, Ill.

[73] Assignee: Abbott Laboratories, Abbott Park, Ill.

[*] Notice: The portion of the term of this patent subsequent to Jan. 31, 2012 has been disclaimed.

[21] Appl. No.: 634,634

[22] Filed: Dec. 27, 1990

[51] Int. Cl.⁶ ............... A61K 37/00; A61K 37/02; C07K 5/00; C07K 7/00

[52] U.S. Cl. .................... 530/329; 530/317; 530/327; 514/11; 514/16; 514/17

[58] Field of Search ............ 530/329, 327, 317; 514/11, 16, 17

[56] References Cited

FOREIGN PATENT DOCUMENTS 9009162 8/1990 WIPO .

OTHER PUBLICATIONS

Kohl et al vol. 20 Eur J Immunology pp. 1463–1468, 1990.

Hartung et al, J of Immunology vol. 130, No. 3, pp. 1345–1349, Mar. 1983.

Swerlick et al., *The Journal of Immunology*, vol. 140, No. 7, Apr. 1988, pp. 2376–2381.

Mollison et al, PNAS vol. 86, pp. 292–296, Jan. 1989.

T. E. Hugli, "Structure and Function of the Anaphylatoxins," *Springer Seminars in Immunopathology*, vol. 7 (1984).

H. P. Hartung, et al., "Induction of Thromboxane Release from Macrophages by Anaphylatoxin Peptide C3a Complement and Synthetic Hexapeptide C3a 72–77," *J. Immunol.*, 130(3):1345–1349 (1983).

B. Weinstein, "The Chemistry and Biochemistry of Amino Acids, Peptides, and Proteins," Marcel Dekker, New York (1983), pp. 267–277.

*Primary Examiner*—Robert J. Hill, Jr.
*Assistant Examiner*—A. M. Davenport
*Attorney, Agent, or Firm*—Jerry F. Janssen

[57] ABSTRACT

Oligopeptide compounds or oligopeptide analogue compounds of the formula A-B-D-E-G-J-L-M-Q are ligands for the anaphylatoxin receptor and are useful in the treatment of inflammatory disease states.

Also disclosed are anaphylatoxin receptor ligand compositions and a method for modulating anaphylatoxin activity.

14 Claims, No Drawings

HEXA- AND HEPTAPEPTIDE ANAPHYLATOXIN-RECEPTOR LIGANDS

TECHNICAL FIELD

This invention relates to organic compounds that modulate anaphylatoxin activity. It also relates to methods and compositions for modulating anaphylatoxin activity in human and animal hosts in need of such treatment.

BACKGROUND OF THE INVENTION

A wide variety of conditions including infection by bacteria, viruses or fungi, infiltration by cancer cells, allergic or autoimmune disorders and physically- or chemically-induced trauma causes an inflammatory response in humans. In all of these diseases and conditions in man and in most mammals, activation of the complement system (a set of proteins, regulatory factors and proteolytic enzymes) via either the classical or the alternative pathway results in the generation of biologically active peptides which serve to amplify and exacerbate the resulting inflammation. The most active peptide, anaphylatoxin C5a, a 74-amino acid polypeptide, is generated by cleavage of the alpha-chain of native C5 at a specific site by convertases (proteolytic enzymes) of the blood complement system as well as by enzymes of the coagulation system. C5a exists in vivo in two biologically active forms. Once it is liberated from C5, the carboxyl terminal arginine of C5a is rapidly removed by carboxypeptidase-N, leaving the des-Arg derivative. Although C5a des-Arg is less active than C5a, both are potent inflammatory mediators at concentrations likely to be generated in vivo (Fernandez, H. N.; Henson, P. M.; Otani, A.; Hugli, T. E. *J. Immunol.* 1978, 120, 109.). Together, these peptides along with C3a, C4a, and their des-Arg degradation products, collectively described herein as anaphylatoxin, are capable of triggering diverse inflammatory reactions.

Among the various cell types, the neutrophil response to C5a is the best defined. Cell surface receptors specific for C5a have been demonstrated on the neutrophil (Chenoweth, D. E.; Hugli, T. E. *Proc. Natl. Acad. Sci. U.S.A.* 1978, 75, 3943-3947. Huey, R.; Hugli, T. E. *J. Immunol.* 1985, 135, 2063-2068. Rollins, T. E.; Springer, M. S. *J. Biol. Chem.* 1985, 260, 7157-7160.), and the ligand-receptor interaction promotes human polymorphonuclear leukocyte (PMN) migration in a directed fashion (chemotaxis), adherence, oxidative burst, and granular enzyme release from these cells (Hugli, T. E. *Springer Semin. Immunopathol.* 1984, 7, 193-219.). The interaction of C5a with PMN and other target cells and tissues results in increased histamine release, vascular permeability, smooth muscle contraction, and an influx into tissues of inflammatory cells, including neutrophils, eosinophils, and basophils (Hugli, T. E. *Springer Semin. Immunopathol.* 1984, 7, 193-219.). C5a may also be important in mediating inflammatory effects of phagocytic mononuclear cells that accumulate at sites of chronic inflammation (Allison, A. C.; Ferluga, J.; Prydz, H.; Scherlemmer, H. U. *Agents and Actions* 1978, 8, 27.). C5a and C5a des-Arg can induce chemotaxis in monocytes (Ward, P. A. *J. Exp. Med.* 1968, 128, 1201. Snyderman, R.; Shin, H. S.; Dannenberg, A. C. *J. Immunol.* 1972, 109, 896.) and cause them to release lysosomal enzymes (McCarthy, K.; Henson, P. S. *J. Immunol.* 1979, 123, 2511.) in a manner analogous to the neutrophil responses elicited by these agents. Recent studies suggest that C5a may have an immunoregulatory role by enhancing antibody particularly at sites of inflammation (Morgan, E. L.; Weigle, W. O.; Hugli, T. E. *J. Exp. Med.* 1982, 155, 1412. Weigle, W. O.; Morgan, E. L.; Goodman, M. G.; Chenoweth, D. E.; Hugli, T. E. *Federation Proc.* 1982, 41, 3099. Morgan, E. L.; Weigle, W. O.; Hugli, T. E. *Federation Proc.* 1984, 43, 2543.).

C5a and C5a des-Arg play important roles in host defenses against bacterial infections and possibly in the mediation of some pathologic lesions such as the leukocyte infiltration seen in the lungs during acute respiratory distress syndrome. This mechanism seems to play a role in different pathological situations like pulmonary distress during hemodialysis, leukophoresis, cardiopulmonary bypass, and in acute myocardial infarction. Complement activation has been postulated to play an important pathological role in rheumatoid arthritis, serum sickness, systemic lupus erythematosus, ulcerative colitis, and forms of hepatic cirrhosis, chronic hepatitis, and glomerulonephritis, in certain shock states, during hemodialysis, and cardiopulmonary bypass, acute pancreatitis, myocardial infarction (which may be worsened by C5a-induced leukoembolization following the interaction of complement with atheromatous plaques), asthma, bronchoconstriction, some auto-allergic diseases, transplant rejection, and post-viral encephalopathies.

By serving as antagonists by binding to and blocking the anaphylatoxin receptor, certain compounds of the present invention can reduce or prevent anaphylatoxin-mediated inflammation. Other compounds of the present invention are agonists that mimic anaphylatoxin activity, and assist the body in building its defense mechanism against invasion by infectious agents and malignancy. Additionally, these compounds may influence the immunoregulatory effects of anaphylatoxin. The possible involvement of anaphylatoxin in a wide range of diseases, as indicated by these examples, suggests that anaphylatoxin receptor ligands could have clinical applications for the treatment and prevention of the above-mentioned pathological conditions.

SUMMARY OF THE INVENTION

In accordance with the principal embodiment of the present invention, there are provided anaphylatoxin activity modifying compounds of the formula A-B-D-E-G-J-L-M-Q and the pharmaceutically acceptable salts, esters, or amides thereof.

In the generic formula given above, the groups A through Q have the following values:

A is $R_1$-$R_2$-$R_3$;

B is selected from $R_4$-$R_5$-$R_6$, $R_{31}$, $R_{32}$, $R_{35}$ and $R_{37}$;

D is selected from $R_7$-$R_8$-$R_9$, $R_{31}$, $R_{32}$, $R_{35}$ and $R_{37}$;

E is selected from $R_{10}$-$R_{11}$-$R_{12}$, $R_{31}$, $R_{32}$, $R_{35}$ and $R_{37}$;

G is selected from $R_{13}$-$R_{14}$-$R_{15}$, $R_{31}$, $R_{32}$, $R_{35}$ and $R_{37}$;

J is selected from $R_{16}$-$R_{17}$-$R_{18}$, $R_{31}$, $R_{32}$, $R_{35}$ and $R_{37}$;

L is selected from $R_{19}$-$R_{20}$-$R_{21}$, $R_{31}$, $R_{32}$, $R_{35}$ and $R_{37}$;

M is selected from a valence bond, $R_{22}$-$R_{23}$-$R_{24}$, $R_{31}$, $R_{32}$, $R_{35}$ and $R_{37}$;

Q is $R_{25}$-$R_{26}$-$R_{27}$;

B and D, taken together, optionally represent a group selected from $R_{33}$, $R_{34}$, $R_{38}$, $R_{39}$, $R_{40}$, $R_{41}$, $R_{42}$, $R_{43}$, and $R_{44}$;

D and E, taken together, optionally represent a group selected from $R_{33}$, $R_{34}$, $R_{38}$, $R_{39}$, $R_{40}$, $R_{41}$, $R_{42}$, $R_{43}$, and $R_{44}$;

E and G, taken together, optionally represent a group selected from $R_{33}$, $R_{34}$, $R_{38}$, $R_{39}$, $R_{40}$, $R_{41}$, $R_{42}$, $R_{43}$, and $R_{44}$;

G and J, taken together, optionally represent a group selected from $R_{33}$, $R_{34}$, $R_{38}$, $R_{39}$, $R_{40}$, $R_{41}$, $R_{42}$, $R_{43}$, and $R_{44}$;

J and L, taken together, optionally represent a group selected from $R_{33}$, $R_{34}$, $R_{38}$, $R_{39}$, $R_{40}$, $R_{41}$, $R_{42}$, $R_{43}$, and $R_{44}$;

L and M, taken together, optionally represent a group selected from $R_{33}$, $R_{34}$, $R_{38}$, $R_{39}$, $R_{40}$, $R_{41}$, $R_{42}$, $R_{43}$, and $R_{44}$; and one or more of the groups $R_5$-$R_6$-$R_7$; $R_8$-$R_9$-$R_{10}$; $R_{11}$-$R_{12}$-$R_{13}$; $R_{14}$-$R_{15}$-$R_{16}$; $R_{17}$-$R_{18}$-$R_{19}$; $R_{20}$-$R_{21}$-$R_{22}$; or $R_{23}$-$R_{24}$-$R_{25}$; independently optionally represent $R_{36}$.

The group $R_1$ is selected from the group consisting of lower alkyl, aryl, arylalkyl, and hydrogen.

$R_2$ is selected from the group consisting of $>CR_{99}R_{100}$ and oxygen, with the proviso that when $R_2$ is oxygen, $R_1$ is aryl, lower alkyl or arylalkyl.

$R_3$ is selected from $>C=O$ or $>CH_2$, with the proviso that when $R_3$ is $>CH_2$ then $R_2$ cannot be oxygen.

$R_4$ is selected from the group consisting of $>CH_2$, $>O$, $>S$, and $>NR_{101}$ where $R_{101}$ is hydrogen, lower alkyl, arylalkyl, alkenyl, hydroxy or alkoxy, with the proviso that when $R_4$ is $>O$ or $>S$ then $R_1$, $R_2$ and $R_3$ taken together represent a group selected from lower alkyl, arylalkyl or hydrogen.

$R_5$ is selected from the group consisting of $CR_{201}R_{202}$, $>NR_{203}$, $>C=CR_{205}R_{206}$, existing in either the Z- or E-configuration, and substituted cyclopropyl of the formula

$R_6$, $R_9$, $R_{12}$, $R_{15}$, $R_{18}$, $R_{21}$, and $R_{24}$ are independently selected from the group consisting of $>C=O$, $>CH_2$, $-CH_2C(O)-$, $-NHC(O)-$, $>C=S$, $>SO_2$, and $>P(O)X$ where X is selected from hydroxy, alkoxy, amino, alkylamino and dialkylamino.

$R_7$, $R_{10}$, $R_{13}$, $R_{16}$, $R_{19}$, and $R_{22}$, are independently selected from $>CH_2$ and $>NR_{50}$ where $R_{50}$ is selected from the group consisting of hydrogen, lower alkyl, arylalkyl, aryl, hydroxy and alkoxy.

$R_8$ is selected from the group consisting of $>CR_{210}R_{211}$, $>NR_{213}$, $>C=CR_{215}R_{216}$, existing in either the Z- or E-configuration, and substituted cyclopropyl of the formula

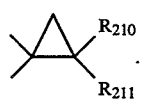

$R_{11}$ is selected from the group consisting of $>CR_{220}R_{221}$, $>NR_{223}$, $>C=CR_{225}R_{226}$, existing in either the Z- or E-configuration, and substituted cyclopropyl of the formula

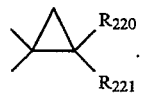

$R_{14}$ is selected from the group consisting of $>CR_{230}R_{231}$, $>NR_{233}$, $>C=CR_{235}R_{236}$, existing in either the Z- or E-configuration, and substituted cyclopropyl of the formula

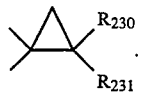

$R_{17}$ is selected from the group consisting of $>CR_{301}R_{302}$, $>NR_{303}$, $>C=CR_{305}R_{306}$, existing in either the Z- or E-configuration, and substituted cyclopropyl of the formula

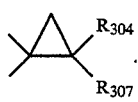

$R_{20}$ is selected from $>CR_{310}R_{311}$ or $>C=CR_{315}R_{316}$, existing in either the Z- or E-configuration, and substituted cyclopropyl of the formula

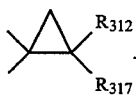

$R_{23}$ is selected from the group consisting of $>CR_{320}R_{321}$, $>C=CR_{325}R_{326}$, existing in either the Z- or E-configuration, and substituted cyclopropyl of the formula

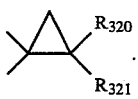

$R_{25}$ is selected from the group consisting of $>O$ and $>NR_{109}$ where $R_{109}$ is selected from hydrogen, lower alkyl, and arylalkyl.

$R_{26}$ is selected from the group consisting of hydrogen, lower alkyl, arylalkyl, and $>NR_{110}$ where $R_{110}$ is selected from hydrogen, aryl, arylalkyl, and lower alkyl, with the provisos that (i) when $R_{25}$ is $>O$, then $R_{26}$ is lower alkyl, and (ii) when $R_{26}$ is hydrogen, lower alkyl or arylalkyl, then $R_{27}$ is absent.

$R_{27}$ is selected from hydrogen, lower alkyl or aryl.

$R_{31}$ is a group having the structure

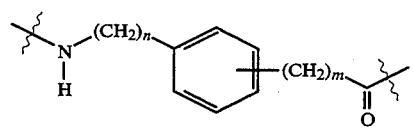

where m and n are integers independently selected from 0, 1 and 2.

$R_{32}$ is a group having the structure

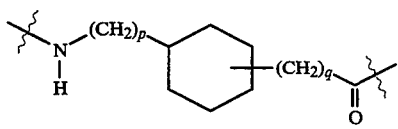

where p and q are integers independently selected from 0, 1 and 2.

$R_{33}$ is a group having the structure

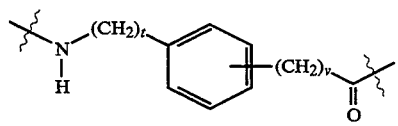

where t and v are integers independently selected from 0, 1, 2 and 3.

$R_{34}$ is a group having the structure

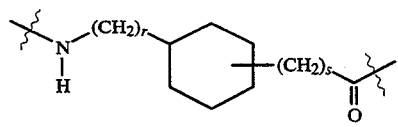

where r and s are integers independently selected from 0, 1, 2 and 3.

$R_{35}$ is a group having the structure

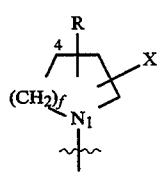

where f is an integer of 0 to 3, X is selected from >C=O and —CH$_2$—. R is selected from hydrogen and lower alkyl, with the provisos that (i) when f is 0, X is at C-2 and R is at C-3 or C-4; (ii) when f is 1, X is at C-2 and R is at C-3, C-4 or C-5 and C-3,4 are saturated or unsaturated; (iii) when f is 2, X is at C-2, C-3 or C-4 and R is at C-2, C-3, C-4, C-5 or C-6 when the position is unoccupied by X and C-3,4 or C-4,5 are saturated or unsaturated and (iv) when f is 3, X is at C-2, C-3 or C-4 and R is at C-2, C-3, C-4, C-5, C-6 or C-7 when the position is unoccupied by X and C-3,4 or C-4,5 or C-5,6 are saturated or unsaturated.

$R_{36}$ is a group having the structure

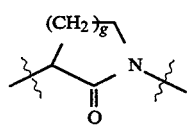

where g is an integer of from 0 to 3.

$R_{37}$ is a group having the structure

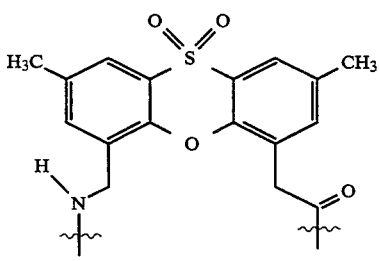

where h is 0 or 1 and j is 0 or 1 with the proviso that either h or j must be 1.

$R_{38}$ is a group having the structure

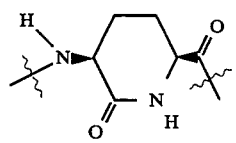

$R_{39}$ is a group having the structure

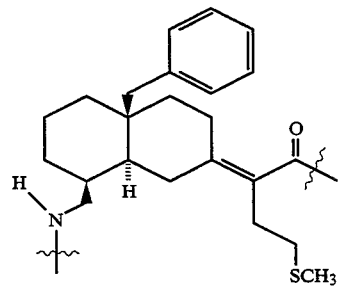

$R_{40}$ is a divalent group having the structure

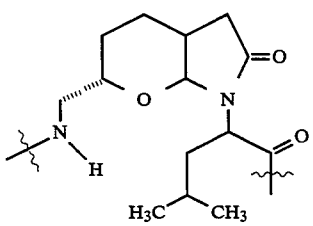

$R_{41}$ is a divalent group having the structure $R_{42}$ is a divalent group having the structure

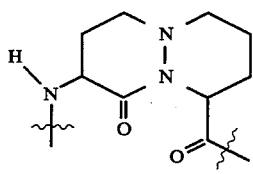

R₄₃ is a divalent group having the structure

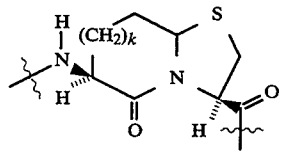

where k is an integer of from zero to two.
R₄₄ is a divalent group having the structure

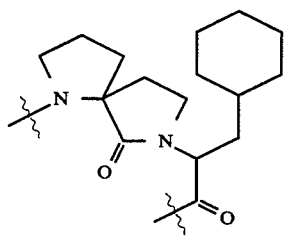

$R_1$ and $R_2$, taken together, optionally may represent aryl or hydrogen.

$R_6$ and $R_7$; $R_9$ and $R_{10}$; $R_{12}$ and $R_{13}$; $R_{15}$ and $R_{16}$; and $R_{19}$; $R_{21}$ and $R_{22}$; each pair taken together may optionally and independently represent a group selected from —C(O)NH—, >CH₂, —(CH₂)₃—, —CH(CH₃)NH—, —CH=CH—, —CH(OH)—, —C≡C—, —C(=CH₂)CH₂—, —CH(OH)CH₂—, —C(O)O—, —C(O)S—, —CH₂C(O)O—, —C(O)OCH₂—, —CH₂C(O)S—, —CH₂O—, —CH₂S—, and —NHC(O)—; with the provisos that (i) at least one of said pair, taken together, must be other than —C(O)NH— and (ii) when $R_5$ is >NR₂₀₃ or >C=CR₂₀₅R₂₀₆, $R_6$ and $R_7$, taken together, represent -C(O)NH— or —C(O)NCH₃—; (iii) when $R_8$ is >NR₂₁₃ or >C=CR₂₁₅R₂₁₆, $R_9$ and $R_{10}$, taken together, represent —C(O)NH— or —C(O)NCH₃—; (iv) when $R_{11}$ is >NR₂₂₃ or >C=CR₂₂₅R₂₂₆, $R_{12}$ and $R_{13}$, taken together represent —C(O)NH— or —C(O)NCH₃—; (v) when $R_{14}$ is >NR₂₃₃ or >C=CR₂₃₅R₂₃₆, $R_{15}$ and $R_{16}$, taken together, represent —C(O)NH— or —C(O)NCH₃—; (vi) when $R_{17}$ is >NR₃₀₃ or >C=CR₃₀₅R₃₀₆, $R_{18}$ and $R_{19}$, taken together, represent —C(O)NH— or —C(O)NCH₃—; (vii) when $R_{20}$ is >NR₃₁₃ or >C=CR₃₁₅R₃₁₆, $R_{21}$ and $R_{22}$, taken together, rep,resent —C(O)NH— or —C(O)NCH₃—.

$R_{26}$ and $R_{27}$, taken together, optionally represent hydrogen, with the proviso that when $R_{25}$ is >O, then $R_{26}$ and $R_{27}$, taken together, represent hydrogen, lower alkyl or arylalkyl.

$R_1$, $R_2$ and $R_3$, taken together, optionally represent a group selected from lower alkyl, arylalkyl, alkenyl, hydrogen, or an N-terminal protecting group.

$R_{205}$, $R_{206}$, $R_{215}$, $R_{216}$, $R_{225}$, $R_{226}$, $R_{235}$, $R_{236}$, $R_{305}$, and $R_{306}$ are independently selected from the group consisting of hydrogen, lower alkyl, aryl, arylalkyl (Arylalkyl is excluded from $R_{305}$ and $R_{306}$ when $R_{19}$-$R_{20}$-$R_{21}$ represents an L-arginyl residue.), (cycloalkyl)alkyl, amidoalkyl (For $R_{305}$ and $R_{306}$, benzoyl amides and their heterocyclic variants are excluded when $R_{19}$-$R_{20}$-$R_{21}$ represents an L-arginyl residue.), (carboxyamido) alkyl (For $R_{305}$ and $R_{306}$, aniline amides and their heterocyclic variants are excluded when $R_{19}$-$R_{20}$-$R_{21}$ represents an L-arginyl residue.), ureidoalkyl, and (heterocyclic)alkyl (For $R_{305}$ and $R_{306}$, when, $R_{19}$-$R_{20}$-$R_{21}$ represents an L-arginyl residue, then the heterocycle can only be separated by one methylene unit from the alpha-carbon.).

$R_{99}$, $R_{202}$, $R_{211}$, $R_{221}$, $R_{231}$, $R_{302}$, $R_{311}$ and $R_{321}$ are independently selected from hydrogen, lower alkyl and arylalkyl. For $R_{302}$ and $R_{311}$, arylalkyl is limited to benzyl when $R_{19}$-$R_{20}$-$R_{21}$ or $R_{22}$-$R_{23}$-$R_{24}$ represent respectively an L-arginyl residue.

$R_{100}$ is hydrogen or lower alkyl.

$R_{201}$ is selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, and sulfhydrylalkyl.

$R_{203}$, $R_{213}$, $R_{223}$, $R_{233}$, and $R_{303}$ are independently selected from the group consisting of hydrogen, lower alkyl, alkenyl, arylalkyl (Arylalkyl is limited to benzyl at $R_{303}$ when $R_{19}$-$R_{20}$-$R_{21}$ represents an L-arginyl residue), (cycloalkyl)alkyl, aminoalkyl (Aryl and arylalkyl amines are excluded from $R_{303}$ when $R_{19}$-$R_{20}$-$R_{21}$ represents an L-arginyl residue.), amidoalkyl (Benzoyl amides and their heterocyclic variants are excluded from $R_{303}$ when $R_{19}$-$R_{20}$-$R_{21}$ represents an L-arginyl residue.), hydroxyalkyl, guanidinoalkyl, carboxyalkyl, (carboxyamido)alkyl (Aniline amides and their heterocyclic variants are excluded from $R_{303}$ when $R_{19}$-$R_{20}$-$R_{21}$ represents an L-arginyl residue.), (carboxyhydrazino) alkyl, ureidoalkyl, (heterocyclic) alkyl (When $R_{19}$-$R_{20}$-$R_{21}$ represents an L-arginyl residue, then the heterocycle at $R_{303}$ can only be separated by one methylene unit from the alpha-carbon.), (thioalkoxy) alkyl, and sulfhydrylalkyl, with the proviso that none of the groups $R_{203}$, $R_{213}$, $R_{223}$, $R_{233}$, or $R_{303}$, may be a vinyl group nor have a heteroatom directly attached to the nitrogen or separated from it by one methylene unit.

$R_{210}$ is selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, ureidoalkyl, (carboxyhydrazino)alkyl, (heterocyclic)alkyl, (thioalkoxy)alkyl, and sulfhydrylalkyl.

$R_{220}$ and $R_{230}$ are independently selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, and sulfhydrylalkyl.

$R_{301}$ and $R_{310}$ are independently selected from the group consisting of hydrogen, lower alkyl, alkenyl, aryl, arylalkyl (Arylalkyl is limited to benzyl for $R_{301}$ and $R_{310}$ when $R_{19}$-$R_{20}$-$R_{21}$ and $R_{22}$-$R_{23}$-$R_{24}$ respectively represent an L-arginyl residue.), (cycloalkyl)alkyl, aminoalkyl (Aryl and arylalkyl amines are excluded for $R_{301}$ and $R_{310}$ when $R_{19}$-$R_{20}$-$R_{21}$ and $R_{22}$-$R_{23}$-$R_{24}$ respectively represent an L-arginyl residue.) amidoalkyl (Benzoyl amides and their heterocyclic variants are excluded for $R_{301}$ and $R_{310}$ when $R_{19}$-$R_{20}$-$R_{21}$ and $R_{22}$-$R_{23}$-$R_{24}$ respectively represent an L-arginyl residue.), hydroxyalkyl, guanidinoalkyl, carboxyalkyl, (carboxyamido)alkyl (Aniline amides and heterocyclic variants are excluded for $R_{301}$ and $R_{310}$ when $R_{19}$-$R_{20}$-$R_{21}$ and $R_{22}$-$R_{23}$-$R_{24}$ respectively represent an L-arginyl residue.), (carboxyhydrazino)alkyl, ureidoalkyl, (heterocyclic)alkyl (For $R_{301}$ and $R_{310}$, the heterocycle can only be separated from the alpha carbon by one methylene when $R_{19}$-$R_{20}$-$R_{21}$ and $R_{22}$-$R_{23}$-$R_{24}$ respectively represent an L-arginyl residue.), (thioalkoxy) alkyl, and sulfhydrylalkyl.

$R_{304}$ is independently selected from the group consisting of hydrogen, lower alkyl, alkenyl, aryl, arylalkyl (Arylalkyl is excluded when $R_{19}$-$R_{20}$-$R_{21}$ represents an L-arginyl residue.), (cycloalkyl)alkyl, aminoalkyl (Aryl and arylalkyl amines are excluded when $R_{19}$-$R_{20}$-$R_{21}$ represents an L-arginyl residue.), amidoalkyl (Benzoyl amides and their heterocyclic variants are excluded when $R_{19}$-$R_{20}$-$R_{21}$ represents an L-arginyl residue.), hydroxyalkyl, guanidinoalkyl, carboxyalkyl, (carboxyamido) alkyl (Aniline amides and heterocyclic variants are excluded when $R_{19}$-$R_{20}$-$R_{21}$ represents an L-arginyl residue.), (carboxyhydrazino)alkyl, ureidoalkyl, (heterocyclic)alkyl (When $R_{19}$-$R_{20}$-$R_{21}$ represents an L-arginyl residue, then the heterocycle must be directly attached to the cyclopropyl ring.), (thioalkoxy)alkyl and sulfhydrylalkyl.

$R_{307}$ and $R_{317}$ are independently selected from hydrogen; lower alkyl; aryl and arylalkyl, wherein arylalkyl is excluded for $R_{307}$ and $R_{317}$ when $R_{19}$-$R_{20}$-$R_{21}$ and $R_{22}$-$R_{23}$-$R_{24}$ respectively represent an L-arginyl residue.

$R_{312}$ is independently selected from the group consisting of hydrogen, lower alkyl, alkenyl, aryl, arylalkyl (Arylalkyl is excluded when $R_{22}$-$R_{23}$-$R_{24}$ represents an L-arginyl residue.), (cycloalkyl)alkyl, aminoalkyl (Aryl and arylalkyl amines are excluded when $R_{22}$-$R_{23}$-$R_{24}$ represents an L-arginyl residue.), amidoalkyl (When $R_{22}$-$R_{23}$-$R_{24}$ represents an L-arginyl residue, then benzoyl amides and their heterocyclic variants are excluded.), hydroxyalkyl, guanidinoalkyl, (carboxy)alkyl, (carboxyamido)alkyl (Aniline amides and heterocyclic variants are excluded when $R_{22}$-$R_{23}$-$R_{24}$ represents an L-arginyl residue.), (carboxyhydrazino)alkyl, ureidoalkyl, (heterocyclic)alkyl (When $R_{22}$-$R_{23}$-$R_{24}$ represents an L-arginyl residue, then the heterocycle must be directly attached to the cyclopropyl ring.), and sulfhydrylalkyl.

$R_{315}$ and $R_{316}$ are independently selected from the group consisting of hydrogen, lower alkyl, aryl, arylalkyl (Arylalkyl is excluded when $R_{22}$-$R_{23}$-$R_{24}$ represents an L-arginyl residue.), and (cycloalkyl)alkyl.

$R_{320}$ and $R_{323}$ are selected from the group consisting of hydrogen, lower alkyl, alkenyl, aryl, arylalkyl, (cycloalkyl)alkyl, and guanidinoalkyl.

$R_{325}$ and $R_{326}$ are independently selected from the group consisting of hydrogen, lower alkyl, aryl, arylalkyl, and (cycloalkyl)alkyl.

$R_{201}$ and $R_{202}$, $R_{210}$ and $R_{211}$, $R_{220}$ and $R_{221}$, $R_{230}$ and $R_{231}$, $R_{301}$ and $R_{302}$, $R_{310}$ and $R_{311}$, $R_{320}$ and $R_{321}$, each pair taken together, independently may optionally represent —$(CH_2)_z$— where z is an integer of from 2 to 6.

All of the foregoing definitions are with the provisos that, in the compounds of the present invention, (i) when more than one sulfhydrylalkyl is present in the compound, the compound exists in the oxidized disulfide form producing a cyclic molecule, or the two sulfhydryl moieties are connected by a $C_2$ to $C_8$ alkylene chain and (ii) when the compound contains a free amino group and carboxyl group, they can be cyclized to give the corresponding lactam.

The present invention also relates to a method for modulating anaphylatoxin activity in a mammal in need of such treatment, comprising administering to the mammal a therapeutically effective amount of a compound of claim 1.

The invention further relates to an anaphylatoxin modulating compositions comprising a pharmaceutical carrier and a therapeutically effective amount of a compound of claim 1.

DETAILED DESCRIPTION

As discussed above, C5a is the most active of a class of biologically active peptides which serves to amplify and exacerbate inflammation. While C5a contains 74 amino acid residues, it has been found in accordance with the present invention that oligopeptides containing as few as six amino acid residues are also actively bound by C5a receptors. Moreover, it has been found that peptidomimetic compounds (i.e. compounds which mimic the activity of peptides) in which certain groups replace the α-carbon, carbonyl group, and amide-nitrogen group of the individual amino acids in oligopeptides are also actively bound by C5a receptors.

The chemical structures of the compounds of the present invention are best understood by reference to the following structural formula in which it is understood that the segments are joined serially at the free valence bonds to form the compound A-B-D-E-G-J-L-M-Q

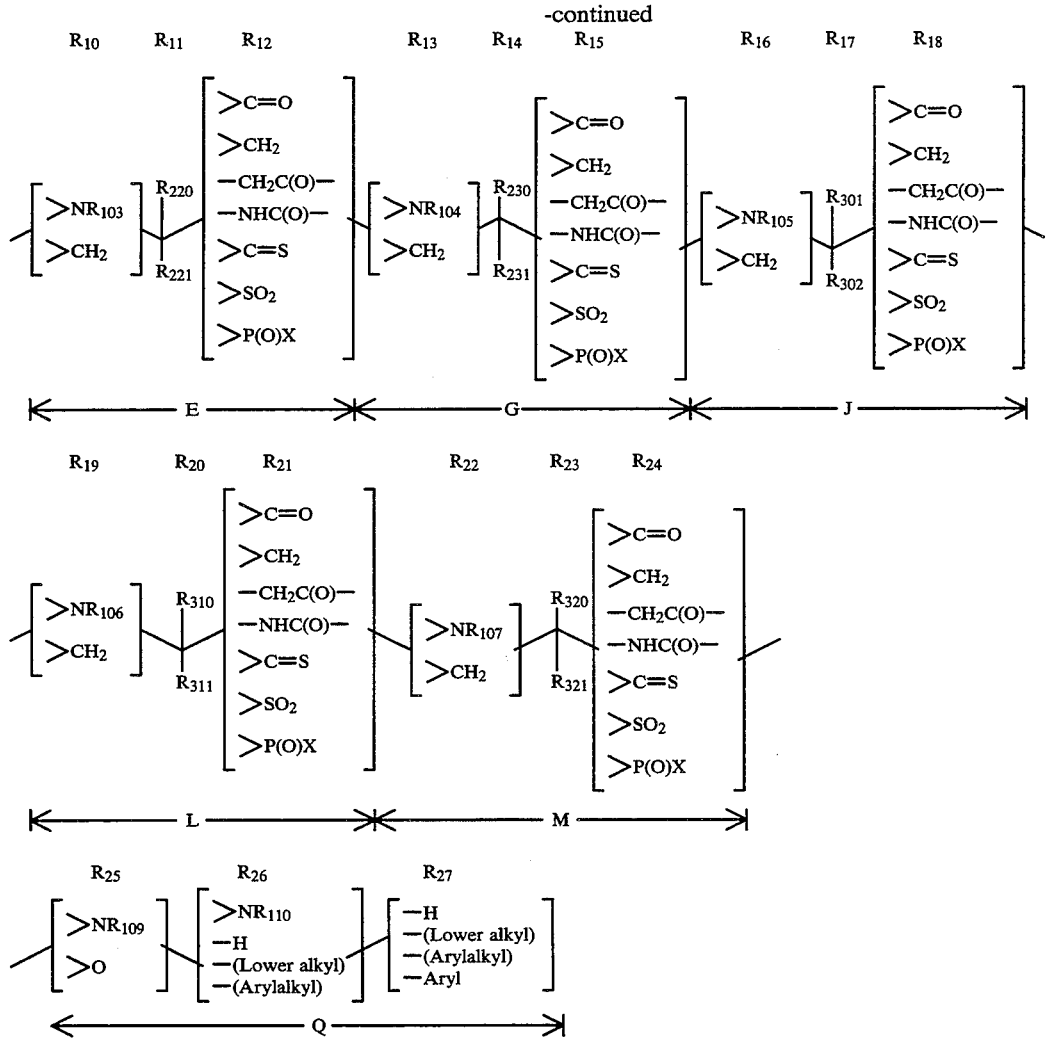

As used throughout this specification and the appended claims, the following terms have the meanings specified.

The term "alkyl" as used herein refers to monovalent straight chain or branched chain groups of 1 to 12 carbon atoms, including, but not limited to methyl, ethyl, n-propyl, isopropyl, n-butyl, sec-butyl, isobutyl, tert-butyl, and the like.

The term "lower alkyl" as used herein refers to straight or branched chain alkyl groups containing from 1 to 8 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "alkylene" as used herein refers to divalent groups of from one to twelve carbon atoms derived by the removal of two hydrogen atoms from straight or branched saturated hydrocarbons. Examples include —$CH_2$—, —$CH(CH_3)$—, —$C(CH_3)_2$—, —$CH(C_2H_5)$—, —$CH_2CH_2$—, —$CH_2CH(CH_3)$—, —$C(CH_3)_2C(CH_3)_2$—, —$CH_2CH_2CH_2$— and the like.

The term "alkenyl" as used herein refers to straight or branched chain groups of 2 to 12 carbon atoms containing a carbon-carbon double bond, including, but not limited to ethenyl, 1-propenyl, 2-propenyl, 2-methyl-1-propenyl, 1-butenyl, 2-butenyl, and the like.

The term "cycloalkyl" as used herein refers to cyclic groups, of 3 to 8 carbons, including, but not limited to cyclopropyl, cyclobutyl, cyclopentyl, cyclohexyl, and the like.

The term "(cycloalkyl)alkyl" as used herein refers to a cycloalkyl group appended to a lower alkyl group, including, but not limited to cyclohexylmethyl and cyclohexylethyl.

The term "alkoxy" as used herein refers to an alkyl group as defined above, attached to the remainder of the molecule through an oxygen atom. Alkoxy groups include, for example, methoxy, ethoxy, isopropoxy, n-butoxy, sec-butoxy, isobutoxy, tert-butoxy, and the like.

The term "sulfhydrylalkyl" as used herein refers to a —SH group appended to a lower alkyl group, as previously defined.

The term "protected sulfhydrylalkyl" refers to a sulfhydrylalkyl group, as previously defined, which has been transformed to the corresponding S-acetamidomethyl (S-Acm) or other similar protecting group such as substituted or unsubstituted arylalkyl or t-butyl as known in the art, including, but not limited to S-phenacetamidomethyl. Typically used sulfhydryl protecting groups are described by E. Gross and J. Meienhofer in Volume 3 of *The Peptides*, Academic Press, 1981.

The term "thioalkoxy" as used herein refers to an alkyl group, as previously defined, attached to the remainder of the molecule through a sulfur atom. Examples of thioalkoxy groups include, but are not limited to, thiomethoxy, thioethoxy, thioisopropoxy, n-thiobutoxy, sec-thiobutoxy, isothiobutoxy, tert-thiobutoxy and the like.

The term "(thioalkoxy)alkyl" as used herein refers to a thioalkoxy group, as just defined, appended to a lower alkyl group.

The term "(thioarylalkoxy)alkyl" as used herein refers to a group of the structure $R_{420}$—S— appended to a lower alkyl where $R_{420}$ is an arylalkyl group as defined below.

The term "aryl" as used herein refers to substituted and unsubstituted carbocyclic aromatic groups including, but not limited to phenyl, 1 - or 2 -naphthyl, fluorenyl, (1,2) -dihydronaphthyl, (1,2,3,4) -tetrahydronaphthyl, indenyl, indanyl, and the like, wherein the aryl group may be substituted with 1, 2, or 3 substituents independently selected from halo, nitro, cyano, $C_1$ to $C_{12}$ alkyl, alkoxy, aroyl and halosubstituted alkyl.

The term "arylalkyl" as used herein refers to an aryl group, as previously defined, appended to an alkyl group, including, but not limited to benzyl, 1- and 2- naphthylmethyl, halobenzyl, alkoxybenzyl, hydroxybenzyl, aminobenzyl, nitrobenzyl, guanidinobenzyl, phenylmethyl(benzyl), 1-phenylethyl, 2-phenylethyl, 1-naphthylethyl, and the like.

The term "benzyl" as used herein refers specifically to to phenyl substituted methyl in which the phenyl group may be substituted with 1, 2, or 3 substituents independently selected from halo, nitro, cyano, alkyl of from one to twelve carbon atoms, alkoxy, aroyl, and halosubstituted alkyl, and the like.

The term "aryloxy" as used herein refers to an aryl group as previously defined, attached to the parent molecular moiety through an oxygen atom. Aryloxy includes, but is not limited to phenoxy, 1-naphthoxy, 2-naphthoxy and the like.

The term "arylalkoxy" as used herein refers to an arylalkyl group as previously defined, attached to the parent molecular moiety through an oxygen atom. Arylalkoxy includes, but is not limited to benzyloxy, 2-phenethyloxy, 1-naphthylmethyloxy and the like.

The term "aroyl" as used herein refers to an aryl group as defined above, attached to the parent molecule through a carbonyl group. Examples include benzoyl and substituted benzoyl.

The term "alkylamino" as used herein refers to a group having the structure —NH(alkyl) where the alkyl portion is as defined above. Alkylamino groups include, for example, methylamino, ethylamino, isopropylamino and the like.

The term "dialkylamino" as used herein refers to a group having the structure —N(alkyl)(alkyl) where the two alkyl groups may be the same or different and are as previously defined.

The term "aminoalkyl" as used herein refers to a group having the structure —$NR_{342}R_{343}$ appended to a lower alkyl group, as previously defined. The groups $R_{342}$ and $R_{343}$ are independently selected from hydrogen, lower alkyl, aryl and arylalkyl. Additionally, $R_{342}$ and $R_{343}$ taken together, may optionally be —$(CH_2)_{mm}$— where mm is an integer of from 2 to 6.

The term "amidoalkyl" as used herein refers to a group having the structure —$NR_{344}C(O)R_{345}$ appended to a lower alkyl group, as previously defined. The groups $R_{344}$ and $R_{345}$ are independently selected from hydrogen, lower alkyl, aryl, arylalkyl, and halosubstituted alkyl. Additionally, $R_{344}$ and $R_{345}$ taken together may optionally be —$(CH_2)_{kk}$— where kk is an integer of from 2 to 6.

The term "carboxyalkyl" as used herein refers to a carboxyl group, —$CO_2H$, appended to a lower alkyl group, as previously defined.

The term "(carboxyamido)alkyl" as used herein refers to a group of the formula —$C(O)NR_{340}R_{341}$, appended to a lower alkyl group, as previously defined. The groups $R_{340}$ and $R_{341}$ are independently selected from hydrogen, lower alkyl, aryl and arylalkyl. Alternatively, $R_{340}$ and $R_{341}$ taken together may optionally be —$(CH_2)_{pp}$— wherein pp is an integer of from 2 to 6.

The term "(carboxyhydrazino)alkyl" as used herein refers to a group having the structure —$C(O)NR_{425}NHR_{430}$ appended to a lower alkyl group, as previously defined. The groups $R_{425}$ and $R_{430}$ are independently selected from hydrogen, lower alkyl, aryl and arylalkyl.

The term "guanidinoalkyl" as used herein refers to a group of the structure —$NR_{346}C(=NR_{347})NHR_{348}$ appended to a lower alkyl group, as previously defined. $R_{346}$, $R_{347}$, and $R_{348}$ are independently selected from hydrogen, lower alkyl, and aryl.

The term "ureidoalkyl" as used herein refers to a group having the structure —$NHC(O)NH_2$ appended to a lower alkyl group, as previously defined.

The term "heterocyclic" as used herein refers to any aromatic or non-aromatic 5- or 6-membered ring containing from one to three heteroatoms independently selected from the group consisting of one nitrogen, oxygen, or sulfur; one oxygen and one nitrogen; one sulfur and one nitrogen; one two or three nitrogen; wherein the 5-membered ring has 0 to 2 double bonds and the 6-membered ring has 0 to 3 double bonds, wherein the nitrogen and sulfur heteroatoms may optionally be oxidized, wherein the nitrogen heteroatom may optionally be quaternized, and including any bicyclic group in which any of the above heterocyclic rings is fused to a benzene ring. Representative heterocycles include, but are not limited to pyrrolyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazoyl, oxazolidinyl, isoxazolyl, isoxazolidinyl, morpholinyl, indolyl, quinolinyl, thiazolyl, thiazolidinyl, isothiazolyl, isothiazolidinyl, isoquinolinyl, benzimidazolyl, benzothiazolyl, benzoxazolyl, furyl, thienyl, and benzothienyl.

The term "(heterocyclic)alkyl" as used herein refers to a heterocyclic group, as previously defined, appended to an alkyl group as previously defined.

The term "hydroxyalkyl" as used herein refers to —OH appended to a lower alkyl group.

The term "naturally occuring amino acid" refers to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

The term "N-terminal protecting group" refers to those groups intended to protect the N-terminus against undesirable reactions during synthetic procedures or to prevent the attack of exopeptidases on the final compounds or to increase the solubility of the final compounds and includes, but is not limited to acyl, acetyl, pivaloyl, tert-butylacetyl, tert-butyloxycarbonyl (Boc), carbobenzyloxycarbonyl (Cbz), benzoyl groups or an L- or D-aminoacyl residue, which may itself be N-protected similarly. Other groups may be found in Volume 3 of *The Peptides*, E. Gross and J. Meienhofer, Academic Press, 1981.

The term "anaphylatoxin" is used herein to mean C5a, C4a, C3a, or the corresponding des-Arg degradation products.

The term "pharmaceutically acceptable salt" refers to non-toxic acid addition salts such as salts formed with inorganic acids such as hydrochloric acid, hydrobromic acid, phosphoric acid, sulfuric acid and perchloric acid or with organic acids such as acetic acid, oxalic acid, maleic acid, malic acid, tartaric acid, citric acid, succinic acid or malonic acid. Other pharmaceutically acceptable salts include inorganic nitrate, sulfate, acetate, malate, formate, lactate, tartrate, succinate, citrate, p-toluenesulfonate, and the like, including, but not limited to cations based on the alkali and alkaline earth metals, such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Examples of pharmaceutically acceptable, non-toxic esters of the compounds of this invention include $C_1$ to $C_6$ alkyl esters wherein the alkyl group is straight or branched chain. Acceptable esters also include $C_5$ to $C_7$ cycloalkyl esters as well as arylalkyl esters such as, but not limited to benzyl. $C_1$ to $C_4$ alkyl esters are preferred. Esters of the compound of formula I may be prepared according to conventional methods.

Examples of pharmaceutically acceptable, non-toxic amides of the compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$ to $C_3$ alkyl primary amides and $C_1$ to $C_2$ dialkyl secondary amides are preferred. Amides of the compound of formula I may be prepared according to conventional methods.

Numerous asymmetric centers may exist in the compounds of the present invention. The present invention contemplates the various stereoisomers and mixtures thereof. In particular, chiral centers can exist at $R_5$, $R_8$, $R_{11}$, $R_{14}$, $R_{17}$, $R_{20}$, and $R_{23}$. Compounds of the present invention containing up to three α-amino acid residues of non-natural configuration have also been found to be effective as modulators of anaphylotoxin activity.

Particular stereoisomers are prepared by selecting the starting amino acids or amino acid analogs having the desired stereochemistry and reacting these starting materials by the methods detailed below. Starting compounds of particular stereochemistry are either commercially available or are made by the methods detailed below and resolved by techniques well known in the organic chemical arts.

One class of preferred compounds of the present invention are those in which the groups $R_4$, $R_7$, $R_{10}$, $R_{13}$, $R_{16}$, $R_{19}$, and $R_{22}$ are independently selected from >NH and >N-(lower alkyl).

In another class of preferred compounds of the present invention, the groups $R_6$, $R_9$, $R_{12}$, $R_{15}$, $R_{18}$, $R_{21}$, and $R_{24}$ are independently selected from >C=O and >CH$_2$.

The group $R_5$ is preferably selected from >CR$_{201}$R$_{202}$ where $R_{201}$ is selected from aryl or arylalkyl; where $R_{202}$ is selected from hydrogen or lower alkyl; >NR$_{203}$ where $R_{203}$ is arylalkyl; >C=CR$_{205}$R$_{206}$, existing in the Z- or E-configuration where $R_{205}$ is selected from hydrogen or lower alkyl; where $R_{206}$ is selected from aryl or arylalkyl; and substituted cyclopropyl of the formula $$\underset{R_{202}}{\overset{R_{201}}{\diagdown\!\!\!\triangle}}$$

where $R_{201}$ is selected from aryl or arylalkyl; where $R_{202}$ is selected from hydrogen or lower alkyl.

$R_8$ is preferably selected from the group consisting of >CR$_{210}$R$_{211}$ where $R_{210}$ is selected from the group consisting of lower alkyl, arylalkyl; aminoalkyl; guanidinoalkyl; where $R_{211}$ is selected from hydrogen and lower alkyl; >NR$_{213}$ where $R_{213}$ is selected from the group consisting of lower alkyl, arylalkyl; aminoalkyl; and guanidinoalkyl; with the proviso that $R_{213}$ may not have a heteroatom directly attached to the nitrogen nor separated from it by one methylene unit; >C=CR$_{215}$R$_{216}$ where $R_{215}$ is selected from hydrogen and lower alkyl; where $R_{216}$ is selected from arylalkyl and lower alkyl; and substituted cyclopropyl of the formula $$\underset{R_{211}}{\overset{R_{210}}{\diagdown\!\!\!\triangle}}$$

where $R_{210}$ is selected from the group consisting of lower alkyl, arylalkyl; aminoalkyl; guanidinoalkyl; and (aminothioalkoxy) alkyl; where $R_{211}$ is selected from hydrogen or lower alkyl.

The group $R_{17}$ preferably is selected from the group consisting of >CR$_{301}$R$_{302}$ where $R_{301}$ is selected from the group consisting of lower alkyl; arylalkyl (Arylalkyl is limited to benzyl when $R_{19}$-$R_{20}$-$R_{21}$ represents an L-arginyl residue.); $R_{302}$ is selected from hydrogen and lower alkyl; NR$_{303}$; $R_{303}$ is selected from the group consisting of hydrogen; lower alkyl; (cycloalkyl)alkyl; and arylalkyl (Arylalkyl is limited to benzyl when $R_{19}$-$R_{20}$-$R_{21}$ represents an L-arginyl residue.); >C=CR$_{305}$R$_{306}$, existing in either the Z- or E-configuration; $R_{305}$ is selected from hydrogen and lower alkyl; $R_{306}$ is selected from aryl; arylalkyl (Arylalkyl is excluded when $R_{19}$-$R_{20}$-$R_{21}$ represents an L-arginyl residue.); lower alkyl; hydrogen; and (cycloalkyl)alkyl and substituted cyclopropyl of the formula $$\underset{R_{307}}{\overset{R_{304}}{\diagdown\!\!\!\triangle}}$$

where $R_{304}$ is selected from the group consisting of lower alkyl; aryl; arylalkyl (Arylalkyl is excluded when $R_{19}$-$R_{20}$-$R_{21}$ represents an L-arginyl residue.); and (cycloalkyl)alkyl; $R_{302}$ is selected from hydrogen and lower alkyl.

The group $R_{20}$ is preferably selected from the group consisting of $>CR_{310}R_{311}$ where $R_{310}$ is selected from the group consisting of arylalkyl (Arylalkyl is limited to benzyl when $R_{22}$-$R_{23}$-$R_{24}$ represents an L-arginyl residue.); and guanidinoalkyl; $R_{311}$ is selected from hydrogen and lower alkyl; $>C=CR_{315}R_{316}$, existing in either the Z- or E-configuration where $R_{315}$ is selected from hydrogen and lower alkyl; $R_{316}$ is selected from aryl; arylalkyl (Arylalkyl is excluded when $R_{22}$-$R_{23}$-$R_{24}$ represents an L-arginyl residue.) and aryl; and substituted cyclopropyl of the formula

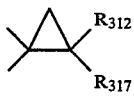

where $R_{312}$ is selected from the group consisting of aryl; arylalkyl (Arylalkyl is excluded when $R_{22}$-$R_{23}$-$R_{24}$ represents an L-arginyl residue.) and guanidinoalkyl; $R_{311}$ is selected from hydrogen and lower alkyl.

One class of preferred compounds of the present invention are those in which when G and L are alpha amino acid residues, the chirality of $R_{14}$ and $R_{20}$ is of the D- or unnatural configuration.

Specific examples of compounds, as well as their pharmaceutically acceptable salts, esters, and amides, contemplated as falling within the scope of the present invention include, but are not necessarily limited to the following:

H-Phenylalanyl-Lysyl-{3-aminomethylbenzoyl}-{(2R/S)-2-Amino-5-phenylpentanoyl}-DArginyl-OH H-Phenylalanyl-Lysyl-{3-aminomethylbenzoyl}-{(2S)-2-Amino-3-cyclohexylpropanoyl}-DArginyl-OH (N-Methyl)Phenylalanyl-Lysyl-Prolyl-Ψ{CH₂NH}-{(2R)-2-Amino-3-cyclohexylpropanoyl}-{(2S)-2-Amino-3-cyclohexylpropanoyl}-DArginyl-OH (N-Methyl)Phenylalanyl-Lysyl-Sarcosyl-D{1-Naphthylalanyl}-{(2S)-2-Amino-3-cyclohexylpropanoyl}-DArginyl-OH (N-Methyl)Phenylalanyl-Lysyl-{(N-Methyl)[(2R/S)-2-Benzyl-4-aminobutanoyl]}-Phenylalanyl-DArginyl-OH {(N- [(3′R/S) -3′-Methylamino-3′-phenylpropyl]) Lysyl-Prolyl-{(2R) -2-Amino-3 -cyclohexylpropanoyl}-Phenylalanyl-DArginyl-OH (N-Methyl)Phenylalanyl-Lysyl-{(N-Methyl)[(2R/S)-2-Cyclohexylmethyl-6-aminohexanoyl]}-Phenylalanyl-DArginyl-OH (N-Methyl)Phenylalanyl-Lysyl-Prolyl-Ψ{CH₂NH}-(2R)-2-Amino-3-cyclohexylpropanoyl}-Phenylalanyl-DArginyl-OH {(N-[(3′R/S)-3′-Amino-3′-phenylpropyl])Lysyl-Prolyl-{(2R)-2-Amino-3-cyclohexylpropanoyl}-Phenylalanyl-DArginyl-OH (N-Methyl)Phenylalanyl-Lysyl-{(N-Methyl)[(2R/S)-2-Benzyl-6-aminohexanoyl}-Phenylalanyl-DArginyl-OH (N-Methyl)Phenylalanyl-Lysyl-Prolyl-D{1-Naphthylalanyl}-Phenylalanyl-{(3R)-3-amino-7-guanidinohexanoyl}-OH (N-Methyl)Phenylalanyl-Lysyl-Prolyl-D{1-Naphthylalanyl}-{1-Naphthylalanyl}-{(1-Naphthylalanyl-{(3R)-3-amino-7-guanidinohexanoyl}-OH In one embodiment of the present invention $R_{13}$-$R_{14}$-$R_{15}$ taken together is {(2R)-2-amino-3-cyclohexylpropanoyl}. Representative of this embodiment include the following compounds, as well as their pharmaceutically acceptable salts, esters, and amides:

(N-Methyl)Phenylalanyl-Lysyl-Prolyl-{(2R)-2-Amino-3-cyclohexylpropanoyl}-Phenylalanyl-Ψ(CH₂NH)-DArginyl-OH (N-Methyl)Phenylalanyl-Lysyl-Prolyl-{(2R)-2-Amino-3-cyclohexyylpropanoyl}-Phenylalanyl-{(3R)-3-Amino-7-guanidino-hexanoyl}-OH (N-Methyl)Phenylalanyl-Lysyl-Sarcosyl-{(2R)-2-Amino-3-cyclohexylpropanoyl}-Phenylalanyl-DArginyl-OH (N-Methyl)Phenylalanyl-Lysyl-(N-Methyl)Alanyl-{(2R)-2-Amino-3-cyclohexylpropanoyl}-Phenylalanyl-DArginyl-OH H-Phenylalanyl-Lysyl-{2-[(2′S)Pyrrolidinyl]acetyl}-{(2R)-2-Amino-3-cyclohexylpropanoyl}-Phenylalanyl-DArginyl-OH (N-Methyl)Phenylalanyl-Lysyl-Prolyl-{(2R)-2-Amino-3-cyclohexylpropanoyl}-Phenylalanyl-Ψ{(R/S)CH(CH₃)NH}-Arginyl-OH (N-Methyl)Phenylalanyl-Lysyl-Prolyl-{(2R)-2-Amino-3-cyclohexylpropanoyl}-{1-Naphthylalanyl}-{(3R)-3-amino-7-guanidinohexanoyl}-OH (N-Methyl)Phenylalanyl-Lysyl-{(2R/S)-2-Methylamino-5-phenylpentanoyl}-{(2R)-2-Amino-3-cyclohexylpropanoyl}-Phenylalanyl-DArginyl-OH H-Phenylalanyl-Lysyl-Alanyl-{(2R)-2-Amino-3-cyclohexylpropanoyl}-{(N-Methyl)(2S)-2-Amino-3-cyclohexylpropanoyl}-DArginyl-OH In another embodiment of the present invention $R_{13}$-$R_{14}$-$R_{15}$ taken together is {(2R)-2-amino-3-cyclohexylpropanoyl} and $R_{16}$-$R_{17}$-$R_{18}$ taken together is {(2S)-2-amino-3-cyclohexylpropanoyl}. Representative examples of this embodiment include the following compounds, as well as their pharmaceutically acceptable salts, esters, and amides:

H-Phenylalanyl-Lysyl-{(3R/S)-1,2,3,4-Tetrahydroisoquinolin-3-carbonyl}-{(2R)-2-Amino-3-cyclohexylpropanoyl}-{(2S )-2-Amino-3-cyclohexylpropanoyl}-DArginyl-OH (N-Allyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH (N,N-Dimethyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH N-Acetyl-Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH (N-Methyl)Phenylalanyl-Lysyl-{(2S)-Azetidine-2-carbonyl}-{(2R)-2-Amino-3-cyclohexylpropanoyl}-{(2S)-2-Amino-3-cyclohexylpropanoyl}-DArginyl-OH (N-Methyl)Phenylalanyl-Norleucyl-(N-Methyl)Alanyl-{(2R)-2-Amino-3-cyclohexylpropanoyl}-{(2S)-2-Amino-3-cyclohexylpropanoyl}-DArginyl-OH H-Phenylalanyl-(N-alpha-Methyl)Lysyl-Prolyl-{(2R)-2-Amino-3-cyclohexylpropanoyl}-{(2S)-2-Amino-3-cyclohexylpropanoyl}-DArginyl-OH (N-Methyl)Phenylalanyl-Lysyl-Prolyl-{(2R)-2-Amino-3-cyclohexylpropanoyl}-{(2S)-2-Amino-3-cyclohexylpropanoyl}-(N-Methyl)Arginyl-OH (N-Methyl)Phenylalanyl-(N-alpha,N-epsilon,Dimethyl)Lysyl-Prolyl-{(2R)-2-Amino-3-cyclohexylpropanoyl}-{(2S)-2-Amino-3-cyclohexylpropanoyl}-DArginyl-OH
(N-Methyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH
(N-Ethyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH
H-Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH
H-Phenylalanyl-Lysyl-{(2S)-Azetidine-2-carbonyl}-{(2R)-2-Amino-3-cyclohexylpropanoyl}-{(2 S)-2-Amino-3-cyclohexylpropanoyl}-DArginyl-OH
(N-isopropyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH
(N,N-Diethyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH
H-Phenylalanyl-Norleucyl-(N-Methyl)Alanyl-{(2R)-2-Amino-3-cyclohexylpropanoyl}-{(2S)-2-Amino-3-cyclohexylpropanoyl}-DArginyl-OH
H-Phenylalanyl-Lysyl-Sarcosyl-{(2R)-2-Amino-3-cyclohexylpropanoyl}-{(2S)-2-Amino-3-cyclohexylpropanoyl}-DArginyl-OH
(N-Methyl)Phenylalanyl-Lysyl-{(2R)-3,3-Dimethylthiazolidine-2-carbonyl}-{(2R)-2-Amino-3-cyclohexylpropanoyl}-{(2S)-2-Amino-3-cyclohexylpropanoyl}-DArginyl-OH
(N-Methyl)Phenylalanyl-Lysyl-(N-Methyl)Phenylalanyl-{(2R)-2-Amino-3-cyclohexylpropanoyl}-{(2S)-2-Amino-3-cyclohexylpropanoyl}-DArginyl-OH
(N-Methyl)Phenylalanyl-Lysyl-D(N-Methyl)Alanyl-{(2R)-2-Amino-3-cyclohexylpropanoyl}-{(2S)-2-Amino-3-cyclohexylpropanoyl}-DArginyl-OH In another embodiment of the present invention, $R_{12}$-$R_{13}$ taken together is $\Psi(CH_2$—$NH$—) and $R_{16}$-$R_{17}$-$R_{18}$ taken together is {(2R)-2-amino-3-cyclohexylpropanoyl}. Representative examples of this embodiment include the following compounds, as well as their pharmaceutically acceptable salts, esters, and amides:

H-Vinylgylcyl-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
H-Lysyl (N-epsilon-acetyl)-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
H-Seryl-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
H-Glutamyl-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
H-Glutaminyl-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
H-Glutamyl (gamma-NHNH$_2$)-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
H-Citrullyl-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
H-(S-Benzyl)Cysteinyl-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
H-Methionyl-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
H-(S-aminomethyl)Cysteinyl-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
H-{(2R)-2-amino-3-chloropropanoyl)-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
{2-Acetamido-3-phenylacryloyl}-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
(N-Methyl)Phenylglycyl-Lysyl-Prolyl-$\Psi${$CH_2$—NH}-{(2R)-2-Amino-3-cyclohexylpropanoyl}-{(2S)-2-Amino-3-cyclohexylpropanoyl}-DArginyl-OH
(N-Methyl)Phenylalanyl-Lysyl-Prolyl-$\Psi${$CH_2$—NH}-{(2R)-2-Amino-3-cyclohexylpropanoyl}-Aza-phenylalanyl-DArginyl-OH
(N-Methyl)Phenylalanyl-Lysyl-Azaglycyl-$\Psi${$CH_2$—NH}-{(2R)-2-Amino-3-cyclohexylpropanoyl}-{(2S)-2-Amino-3-cyclohexylpropanoyl}-DArginyl-OH
(N-Methyl)Phenylalanyl-Lysyl-Prolyl-$\Psi(CH_2NH)$-{(2R)-2-Amino-3-cyclohexylpropanoyl}-{(2S)-2-Amino-3-cyclohexylpropanoyl}-DPhenylalanyl-OH
(N-Methyl)Phenyl-Lysyl-Prolyl-$\Psi(CH_2$—NH)-{(2R)-2-Amino-3-cyclohexylpropanoyl}-Phenylalanyl-DPhenylalanyl-OH In another embodiment of the present invention, $R_1$-$R_2$-$R_3$ taken together as a group is methyl, $R_4$-$R_5$-$R_6$ taken together as a group is L-phenylalanine, and $R_7$-$R_8$-$R_9$ taken together is L-lysine. Representative examples of this embodiment include the following compounds, as well as their pharmaceutically acceptable salts, esters, and amides:

(N-Methyl)Phenylalanyl-Lysyl-Glycyl-$\Psi${S (O$_2$)-NH}-{(2R)-2-Amino-3-cyclohexylpropanoyl}-{(2S)-2-Amino-3-cyclohexylpropanoyl}-$\Psi${$CH_2$—NH}-DArginyl-OH
(N-Methyl)Phenylalanyl-Lysyl-Prolyl-$\Psi${C≡C}-{(2R)-2-Amino-3-cyclohexylpropanoyl}-{(2S)-2-Amino-3cyclohexylpropanoyl}-DArginyl-OH
(N-Methyl)Phenylalanyl-Lysyl-Prolyl-$\Psi${C(=S)—NH}-{(2R)-2-Amino-3-cyclohexylpropanoyl}-{(2S)-2-Amino-3-cyclohexylpropanoyl}-DArginyl-OH
(N-Methyl)Phenylalanyl-Lysyl-Prolyl-$\Psi${$CH_2$—O}-{(2R)-2-Amino-3-cyclohexylpropanoyl}-{(2S)-2-Amino-3-cyclohexylpropanoyl}-DArginyl-OH
(N-Methyl)Phenylalanyl-Lysyl-Prolyl-$\Psi${$CH_2$—S}-{(2R)-2-Amino-3-cyclohexylpropanoyl}-{(2S)-2-Amino-3-cyclohexylpropanoyl}-DArginyl-OH
(N-Methyl)Phenylalanyl-Lysyl-$\Psi${C(=O)-S}-Glycyl-{(2R)-2-Amino-3-cyclohexylpropanoyl}-{(2S)-2-Amino-3-cyclohexylpropanoyl}-DArginyl-OH
(N-Methyl)Phenylalanyl-Lysyl-$\Psi${$CH_2$C(=O)-S}-Glycyl-{(2R)-2-Amino-3-cyclohexylpropanoyl}-{(2S)-2-Amino-3-cyclohexylpropanoyl}-DArglnyl-OH
(N-Methyl)Phenylalanyl-Lysyl-$\Psi${CH=CH}-Glycyl-{(2R)-2-Amino-3-cyclohexylpropanoyl}-{(2S)-2-Amino-3-cyclohexylpropanoyl}-DArginyl-OH
(N-Methyl)Phenylalanyl-Lysyl-Prolyl-$\Psi${C(=O)—$CH_2$-{(2R)-2-Amino-3-cyclohexylpropanoyl}-{(2S)-2-Amino-3-cyclohexylpropanoyl}-DArginyl-OH (N-Methyl)Phenylalanyl-Lysyl-Prolyl-Ψ{CH(OH)—CH$_2$}-{(2R)-2-Amino-3-cyclohexylpropanoyl}-{(2S)-2-Amino-3-cyclohexylpropanoyl}-DArginyl-OH (N-Methyl)Phenylalanyl-Lysyl-Prolyl-Ψ{C(=CH$_2$)—CH$_2$}-{(2R)-2-Amino-3-cyclohexylpropanoyl}-{(2S)-2-Amino-3-cyclohexylpropanoyl}-DArginyl-OH (N-Methyl)Phenylalanyl-Lysyl-Ψ{C(=O)—N(OMe)}-Glycyl{(2R)-2-Amino-3-cyclohexylpropanoyl}-{(2S)-2-Amino-3-cyclohexylpropanoyl}-DArginyl-OH (N-Methyl)Phenylalanyl-Lysyl-Prolyl-Ψ{PO (OH)-NH}-{(2R)-2-Amino-3-cyclohexylpropanoyl}-{(2S)-2-Amino-3-cyclohexylpropanoyl}-DArginyl-OH (N-Methyl)Phenylalanyl-Lysyl-Prolyl-Ψ{PO(OMe)—NH}-{(2R)-2-Amino-3-cyclohexylpropanoyl}-{(2S)-2-Amino-3cyclohexylpropanoyl}-DArginyl-OH (N-Methyl)Phenylalanyl-Lysyl-Prolyl-Ψ{PO(NHMe)—NH}-{(2R)-2-Amino-3-cyclohexylpropanoyl}-{(2S)-2-Amino-3-cyclohexylpropanoyl}-DArginyl-OH (N-Methyl)Phenylalanyl-Lysyl-Prolyl-Ψ{PO(NMe$_2$)—NH}-{(2R)-2-Amino-3-cyclohexylpropanoyl}-{(2S)-2-Amino-3-cyclohexylpropanoyl}-DArginyl-OH (N-Methyl)Phenylalanyl-Lysyl-Prolyl-Ψ{PO(NH$_2$)—NH}-{(2R)-2-Amino-3-cyclohexylpropanoyl}-{(2S)-2-Amino-3-cyclohexylpropanoyl}-DArginyl-OH (N-Methyl)Phenylalanyl-Lysyl-Ψ{CH$_2$C(=O)—O}-Glycyl-{(2R)-2-Amino-3-cyclohexylpropanoyl}-{(2S)-2-Amino-3-cyclohexyl-propanoyl}-DArginyl-OH (N-Methyl)Phenylalanyl-Lysyl-Prolyl-{(2R)-2-Amino-3-cyclohexylpropanoyl}-{(2S)-2-Amino-3-cyclohexylpropanoyl}-Ψ{CH$_2$—N(CH$_2$CH$_2$C$_6$H$_5$)}-DArginyl-OH.

Method of Treatment

The compounds of the present invention serve to modulate the activity of anaphylatoxin. Certain compounds of the present invention function as anaphylatoxin antagonists, while others function as agonists. The antagonist compounds of the present invention block the anaphylatoxin receptor and prevent anaphylatoxin activity, which makes those compounds useful in the treatment and prevention of injurious conditions or diseases in which anaphylatoxin may be involved. Disease states in which anaphylatoxin is involved include asthma, bronchial allergy, chronic inflammation, systemic lupus erythematosus, vasculitis, serum sickness, angioedema, rheumatoid arthritis, osteoarthritis, gout, bullous skin diseases, hypersensitivity pneumonitis, idiopathic pulmonary fibrosis, immune complex-mediated glomerulonephritis, psoriasis, allergic rhinitis, adult respiratory distress syndrome, acute pulmonary disorders, endotoxin shock, hepatic cirrhosis, pancreatitis, inflammatory bowel diseases (including Crohn's disease and ulcerative colitis), thermal injury, Gram-negative sepsis, necrosis in myocardial infarction, leukophoresis, exposure to medical devices (including but not limited to hemodialyzer membranes and extracorpeal blood circulation equipment), chronic hepatitis, transplant rejection, post-viral encephalopathies, and/or ischemia induced myocardial or brain injury. These compounds may also be used as prophylactics for such conditions as shock accompanying Dengue fever. In addition, a combination of antibiotic and anti-inflammatory agent such as corticosteroids (e.g., methylprednisolone) and one or more of the above mentioned compounds may be employed.

Certain compounds of the invention are useful therapeutic agents because of their ability to mimic or promote anaphylatoxin activity and are therefore useful in stimulating the inflammatory response and immune response in mammals who are deficient in this regard. These agonist compounds may be used to assist the body in building its defense mechanism against invasion by infectious microorganisms or other stress. Interaction by these agonists at the anaphylatoxin receptor makes them useful in treating conditions or diseases including, but not limited to cancers (such as lung carcinoma), immunodeficiency diseases, and severe infections.

In some cases this will involve preventing the underlying cause of the disease state and in other cases, while the underlying disease will not be affected, the compounds of this invention will have the benefit of ameliorating the symptoms or preventing the manifestations of the disease.

The compounds of the present invention may be administered orally, parenterally, by inhalation spray, rectally, or topically in dosage unit formulations containing conventional nontoxic pharmaceutically acceptable carriers, adjuvants and vehicles as desired.

The term "parenteral" as used herein includes subcutaneous, intravenous, intramuscular, intrasternal, intra-arterial injection or infusion techniques, without limitation. The term "topically" encompasses administration rectally and by inhalation spray, as well as by the more common routes of the skin and the mucous membranes of the mouth and nose.

Actual dosage levels of active ingredients in the pharmaceutical compositions of this invention may be varied so as to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.001 mg to about 100 mg, more typically from about 0.1 mg to about 20 mg, of active compound per kilogram of body weight per day are administered daily to a mammalian host. If desired, the effective daily dose may be divided into multiple doses for purposes of administration, e.g. two to four separate doses per day.

Formulation of Pharmaceutical Composition

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents such as sugars, sodium chloride, and the like, Prolonged absorption of the injectable pharmaceutical form may be brought about by the inclusion of agents which delay abdorption such as aluminum monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alignates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternaryammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Anaphylatoxin Receptor Binding Ki Determination

Specific inhibition of C5a binding activity of representative compounds of the present invention was measured using 0.03–1 nM $^{125}$I-C5a with 2.5–25 ug/mL of purified PMNL membrane fragments (Borregaard, N.; Heiple, J. M.; Simons, E. R.; and Clark, R. A. *J. Cell. Biol.* 1983, 97, 52–61.). Free and membrane-bound ligand were separated by filtration. Binding potencies for representative examples of compounds of this invention are listed in Table 1.

TABLE 1

| In vitro C5a Receptor Binding Potency of Compounds of this Invention. | | | |
|---|---|---|---|
| Example | Ki uM | Example | Ki uM |
| 2 | 1.0 | 56 | 0.014 |
| 4 | 180 | 61 | 0.22 |
| 7 | 2.2 | 62 | 0.26 |
| 10 | 85 | 79 | 14.5 |
| 17 | 2.5 | 103 | 0.36 |
| 19 | 130 | 121 | 21 |
| 34 | 0.034 | 134 | 6.8 |
| 40 | 0.59 | 143 | 4.2 |
| 43 | 0.023 | 156 | 0.66 |
| 44 | 30 | 170 | 2.6 |

Synthesis of the Compounds

The novel compounds and salts thereof of the invention can be utilized effectively as therapeutic agents. Accordingly, the present invention further relates to therapeutic compositions comprising a novel compound having the general formula I or salts thereof as an active component.

The compounds of the invention may be prepared by a synthetic method of elongation of a peptide chain through condensation of one amino acid by one, or by a method of coupling fragments consisting of two or several amino acids, or by a combination of these methods in accordance with conventional peptide synthesis methods using starting materials commercially available or synthesized by methods know in the art.

The condensation of two amino acids, the condensation of an amino acid with a peptide or the condensation of one peptide with another peptide may be effected in accordance with conventional condensation methods such as azide method, mixed acid anhydride method, symmetrical anhydride method, DCC(dicyclohexylcarbodiimide) method, active ester method (p-nitrophenyl ester method, N-hydroxysuccinimide ester method, cyanomethyl ester method and the like), Woodward reagent K method, DCC-HOBT(1-hydroxybenzotriazole) method and the like. These condensation reactions may be done by either solution methods or solid phase synthetic methods. When the peptide chain is elongated by the solid phase method, the C-terminal amino acid is linked to an insoluble carrier. As the insoluble carrier, any that can produce a detachable bond by reacting with a carboxyl group in a C-terminal amino acid may be used, and the examples thereof involve, for example, halomethyl resins such as chloromethyl resin, bromomethyl resin and the like, hydroxy-methyl resin, benzhydrylamine resin, and t-alkyloxycarbonyl hydrazide resin.

As conventional polypeptide synthesis, branched chain amino and carboxyl groups at alpha and omega positions in amino acids may be protected/deprotected if necessary. The protecting groups for amino groups which can be used involve, for example, benzyloxycarbonyl (Z), o-chlorobenzyloxycarbonyl ((2-Cl)Z), p-nitrobenzyloxycarbonyl (Z(NO2)), p-methoxy-benzyloxycarbonyl (Z(OMe)), t-butoxycarbonyl (Boc), t-amyloxycarbonyl (Aoc), isobornyloxycarbonyl, admantyloxycarbonyl, 2-(4-biphenyl)-2-propyloxycarbonyl (Bpoc), 9-fluorenyl-methoxycarbonyl (Fmoc), methylsulfonylethoxycarbonyl (Msc), trifluoroacetyl, phthalyl, formyl, 2-nitrophenylsulfenyl (Nps), diphenylphosphinothioyl (Ppt), and dimethylphosphinothioyl (Mpt).

Examples of protecting groups for carboxyl groups include, for example, benzyl ester (OBn), cyclohexyl ester, 4-nitrobenzyl ester (OBnNO2), t-butyl ester (OtBu), 4-picolyl ester (OPic) and the like.

In the course of the synthesis of the present novel compounds, specific amino acids having functional groups other than amino and carboxyl groups in the branched chain such as arginine, cysteine, serine, and the like may be protected, if necessary, with suitable protecting group. It is preferable that for example, the guanidino group (N$^G$) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mds), 1,3,5-trimethylphenylsulfonyl (Mts) and the like, and the thiol group in cysteine may be protected with benzyl, p-methoxybenzyl, triphenylmethyl, acetamidomethyl, ethylcarbamyl, 4-methylbenzyl (4-MeBn), 2,4,6-trimethylbenzyl (Tmb) and the like, and the hydroxyl group in serine may be protected with benzyl (Bn), t-butyl, acetyl, tetrahydropyranyl and the like.

N-Acetylated peptides were prepared in analogy to Example 55. The following literature procedures were used to prepare N-alkyl- or N,N-dialkyl-amino acid derivatives. Lovett, J. A.; Portoghese, P. J. Med. Chem. 1987, 30, 1144-1149. Borch, R. F.; Hassid, A. I. J. Org. Chem. 1972, 37, 1673-1674. Hansen, D. W.; Pilipauskas, D. J. Org. Chem. 1985, 50, 945-950. Grieco, P. A.; Basha, A. J. Org. Chem. 1987, 52, 5746-5749. Shuman, R. T.; Smithwick, E. L.; Smiley, D. L.; Brooke, G. S.; Gesellchen, P. D. "Peptide: Structure and Function", Proceedings of the Eighth American Peptide Symposium, 1984; p 143-146. Cheung, S. T.; Benoiton, N. L. Can. J. Chem. 1977, 55, 906-910. These reactions were carried out either on the elongated peptide-resin or on amino acid derivatives and then incorporated into the peptide-resin.

The following literature procedures were used to prepare (2'S, 3S)-3-amino-2-oxo-1-pyrrolidine-{2'-(4'-6'-amino)}-hexanoic acid, and (2'R,3S)-3-amino-2-oxo-1-pyrrolidine-{2'-(6'-amino)}-hexanoic acid: Freidinger, R. M.; Perlow, D. S.; Veber, D. F. J. Org. Chem. 1982, 47, 104-109. The preparations of Boc-beta-homo amino acid derivatives: N-Boc-(3S)-amino-4-phenyl-n-butanoic acid, N-Boc-(3R)-amino-4-cyclohexyl-n-butanoic acid, N-Boc-(3S)-amino-4-cyclohexyl-n-butanoic acid, N-Boc-(3S)-amino-7-N-Benzyloxycarbonyl-amino-n-heptanoic acid, N-Boc-(3S)-amino-6-guanidino-n-hexanoic acid and N-Boc-(3S)-pyrrolidineacetic acid were performed by the following literatures; Wakiyama, T.; Uratani, H.; Teshima, T.; Shiba, T. Bull. Chem. Soc. Jpn. 1975, 48, 2401. and Rodriguez, M.; Fulcrand, P.; Lauer, J.; Aumelas, A.; Martinez, J. J. Med. Chem. 1989, 32, 522.

The obtained beta-homo amino acid derivatives were incorporated into Merrifield resin as described in: Stewart, J. M.; Young, J. D. "Solid Phase Peptide Synthesis", 2nd edition; Pierce Chemical Co.: Rockford, Ill., 1984; p 71-72. The peptide resin obtained was washed and dried, followed by cleavage and purification to yield the desired peptide analog. The following compounds were prepared by this method (examples; 94, 106, 107, 109, 110, 113, 118, 145, 146, 148, 149, 152, 158, and 160).

The following fragments are dipeptidemimetics, i.e. each fragment replaces two amino acid residues in the sequence; they are prepared as described in the literature:

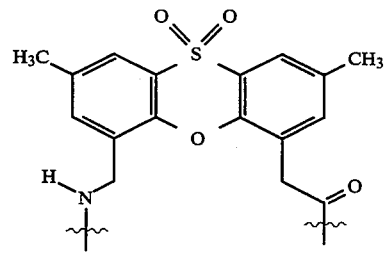

Fragment-1

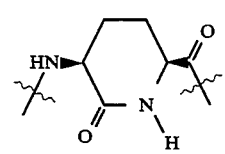

Fragment-2

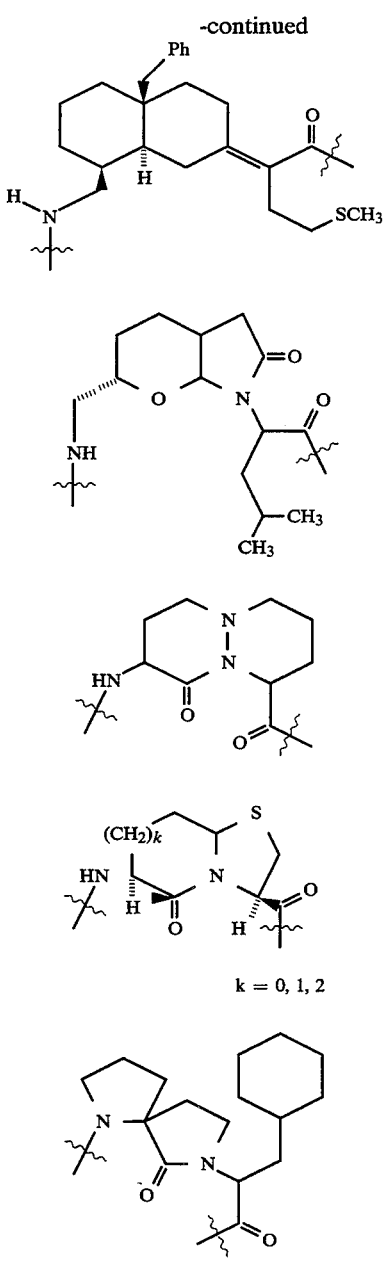

Fragment-3

Fragment-4

Fragment-5 k = 0, 1, 2

Fragment-7

References
1. Fiegel, M. *J. Am. Chem. Soc.* 1986, 108, 181.
2. Kemp, D. S.; McNamara, P. E. *J. Org. Chem.* 1985, 50, 5834.
3. Belanger, P. C.; Dufresne, C.; Scheigetz, J.; Yang, R. N.; Springer, J. P.; Dmitrienko, G. I. *Can. J. Chem.* 1982, 60, 1019.
4. Krstenansky, J. L.; Baranowdki, R. L.; Currie, B. L. *Biochem. Biophys. Res. Commun.* 1982, 109, 1368.
5. Attwood, M. R.; Francis, R. J.; Hassall, C. H.; Krohn, A.; Lawton, G.; Natoff, I. L.; Nixon, J. S.; Redshaw, S.; Thomas, W. A. *FEBS Lett.* 1984, 165, 201.
6. (a) Nagai, U.; Sato, K. *Tetrahedron Lett.* 1985, 647. (b) Baldwin, J.; Lee, E. *Tetrahedron Lett.* 1986, 42, 6551.
7. Hinds, M. G.; Richards, N. G. J.; Robinson, J. A. *J. Chem. Soc Chem. Commun.*, 1988, 1147.

Fragment-6

The compounds of the invention are prepared by standard solid phase peptide synthesis conditions as described in "Solid Phase Peptide Synthesis" by J. M. Stewart and J. D. Young, Second Edition (1984) and as illustrated in Examples 1 and 2 in the experimental section.

The compounds of the invention may also be prepared by partial solid phase synthesis, fragment condensation methods and classical solution methods as exemplified by the methods described in "Peptide Synthesis", Second Edition, M. Bodanszky, Y. S. Klausner, and M. A. Ondetti (1976).

The standard chirality descriptors "R" and "S" are used to indicate an isomerically pure center, "RS" to indicate a mixture, and "R/S" to indicate a single pure isomer of undetermined configuration. The descriptor "±" refers to a d,l mixture of amino acids at the indicated residue. The descriptor Ψ{X} indicates the group, X, that is a replacement for the standard peptide bond, —C(O)NH—. The descriptor "*" or "**" when written in a chemical name indicates the site of a disulfide or amide linkage, respectively.

The foregoing may be better understood by reference to the following examples which are provided for illustration and not limitation of the practice of the invention. Unless otherwise indicated, the standard peptide methods described above and in examples 1 and 2 are used to assemble the different products, using the precursors indicated by the specific peptide sequence. The synthetic product was at least 95% pure, and gave NMR and mass spectra consistent with the proposed structure.

EXAMPLE 1

(N-Methyl)Phenylalanyl-Lysyl(N-epsilon-Cbz)-Prolyl-{(2R)-2-Amino-3-cyclohexylpropanoyl}-Phenylalanyl-Ψ(CH₂NH)-DArginyl(N-guanidino-Tos)-Merrifield Resin Boc-DArg(N-guanidino-Tos)-Merrifield resin (0.4–1.0 g) was placed in a solid phase peptide synthesis vessel and amino acids were attached to the resin sequentially in the following order: Boc-(2R)-2-Amino-3-cyclohexylpropanoic acid, Boc-Proline, (N-alpha-Boc,N-epsilon-Cbz)Lysine, Boc-N-MethylPhenylalanine. Commercially available N-Boc-Phenylalanine was converted to its N,O-dimethylhydroxamate, which was reduced with lithium aluminum hydride to yield N-Boc-Phenylalanal, according to the literature; Nahms, S.; Weinreb, S. M. *Tetrahedron Lett.*, 1981, 22, 3815. After the sequence was stopped at Agenda A step 2, N-Boc-Phenylalanal (3.5 equivalent mole) in 10 mL of DMF containing 0.1% glacial acetic acid was added, followed by sodium cyanoborohydride (10 equivalent mole). The reaction was allowed to proceed at room temperature for 1 hour. After the peptide resin obtained was washed with DMF (3×10 mL) and methylene chloride (3×10 mL), the next synthetic protocol (Agenda A step 2) was initiated to yield the protected peptide resin: (N-Methyl)Phenylalanyl-Lysyl(N-epsilon-Cbz)-Prolyl-{(2R)-2-Amino-3-cyclohexylpropanoyl}-Phenylalanyl-Ψ(CH₂NH)-Arginyl (N-guanidino-Tos)-Merrifield Resin. After the final amino acid was coupled, the protected peptide resin was removed from the reaction vessel by washing the resin three times with 20 mL DMF into a 30–60 mL sintered glass funnel, followed by washing the resin three times with 20 mL methylene chloride. The resin was dried at least five hours and then weighed.

Other amino aldehydes (Boc-N-MethylPhenylalanal, N-alpha-Boc-N-epsilon-Cbz-Lycinal, Boc-(2S)-2-Amino-3-cyclohexylpropanal and Boc-Prolinal were prepared by literature methods: Anhoury, M. L.; Crooy, P.; DeNeys, R.; Eliaers, J. *J. Chem. Soc. Perkin 1* 1974, 191; Hamada, Y.; Shioiri, T. *Chem. Pharm. Bull.* 1982, 30, 1921.

Agenda A

1. De-block: 45% trifluoroacetic acid (TFA) in methylene chloride containing 2.5% anisole (v/v/v).
2. Neutralization: 10% diisopropylethylamine (DIEA) in methylene chloride (v/v).
3. Single Coupling: 0.2–0.4M Boc-amino acid derivative in N,N-dimethylformamide (DMF), 0.2–0.4M diisopropylcarbodiimide (DIC) in methylene chloride, reaction time, 60 minutes
4. Resin base washing: 10% DIEA in methylene chloride (v/v).
5. Single Coupling repeated: same as Step 3.
6. Go to next amino acid residue (go back to Step 1).
7. Upon attachment of the final amino acid to the growing peptide chain, the protecting group (t-Boc) is removed as in Step 1.

EXAMPLE 2

(N-Methyl)Phenylalanyl-Lysyl-Prolyl-{(2R)-2-Amino-3-cyclohexylpropanoyl}-Phenylalanyl-Ψ(CH$_2$NH)-DArginyl-OH The protected peptide resin of Example 1 (0.6 g) was treated with 1.0 mL anisole and 10 mL hydrogen fluoride (HF) for 60 minutes at 0° C. The HF and anisole were removed in vacuo at 0° C., and the mixture of the peptide and resin was washed with diethyl ether (2×25 mL). The crude peptide was extracted from the mixture by treatment with portions of 20% aqueous acetic acid (4×25 mL), lyophilized to a dry amorphous powder (148 mg), and purified by high performance liquid chromatography (HPLC) {column: 21.4 mm ID×25 cm or 41.4 mm ID×25 cm, Dynamax (Rainin), 8 μm silica, C18 reverse-phase column}. The sample (100 mg) was purified by gradient elution {from 20 to 60% (80% acetonitrile in water with 0.1% trifluoroacetic acid)} at a flow rate of 15–45 mL/min. yield: 68.3 mg FAB+ MS: (M+H)+ = 847 Amino Acid Anal.: Cha (0.95), Lys (0.99), Pro (1.07), MePhe (0.95).

EXAMPLE 3

Fmoc-Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH

EXAMPLE 4 (Sequence ID NO. 1)

H-Histidyl-{6-Aminohexanoyl}-Glutaminyl-Leucyl-Glycyl-Arginyl-OH

FAB+ MS: (M+H)+ = 723.

EXAMPLE 5

H-Phenylalanyl-Lysyl-{4-Aminobutanoyl}-{(2S)-2-Amino-3-cyclohexylpropanoyl}-Leucyl-DAlanyl-Arginyl-OH

FAB+ MS: (M+H)+ = 872.

EXAMPLE 6

(N-Methyl)Phenylalanyl-Lysyl-(Fragment-1)-{(2S)-2-Amino-3-cyclohexylpropanoyl}-Ψ{CH$_2$—NH}-DArginyl-OH Fragment-1 is prepared as described in the literature: Fiegel, M. *J. Am. Chem. Soc.* 1986, 108, 181 and incorporated into the peptide by classical solution methods as described in "Peptide Synthesis", Second Edition, M. Bodanszky, Y. S. Klausner, and M. A. Ondetti (1976).

EXAMPLE 7

H-Phenylalanyl-Lysyl-{3-Aminopropanoyl}-{(2S)-2-Amino-3-cyclohexylpropanoyl}-Leucyl-DAlanyl-Arginyl-OH FAB+ MS: (M+H)+ = 858 Amino Acid Anal.: Phe (1.09), Lys (0.95), Cha (0.94), Leu (1.05), Ala (0.94), Arg (0.98)

EXAMPLE 8

H-Phenylalanyl-Lysyl-Alanyl-{(2S)-2-Amino-3-cyclohexylpropanoyl}-{(3RS)-3-Aminocyclohexylcarbonyl}-Arginyl-OH

FAB+ MS: (M+H)+ = 799.

EXAMPLE 9

(N-Methyl)Phenylalanyl-Lysyl-(Fragment-2)-{(2S)-2-Amino-3-cyclohexylpropanoyl}-Ψ{CH$_2$—NH}-DArginyl-OH Fragment-2 is prepared as described in the literature: Kemp, D. S.; McNamara, P. E. *J. Org. Chem.* 1985, 50, 5834 and incorporated into the peptide by classical solution methods as described in "Peptide Synthesis", Second Edition, M Bodanszky, Y. S. Klausner, and M. A. Ondetti (1976).

EXAMPLE 10

H-Phenylalanyl-Lysyl-Alanyl-{(2S)-2-Amino-3-cyclohexylpropanoyl}-{6-Aminohexanoyl}-Arginyl-OH

FAB+ MS: (M+H)+ = 787.

EXAMPLE 11

H-Phenylalanyl-Lysyl-Alanyl-{(2S)-2-Amino-3-cyclohexylpropanoyl}-Isonipecotyl-Arginyl-OH

FAB+ MS: (M+H)+ = 785.

EXAMPLE 12

(N-Methyl)Phenylalanyl-Lysyl-(Fragment-3)-{(2S)-2-Amino-3-cyclohexylpropanoyl}-Ψ{CH$_2$—NH}-DArginyl-OH Fragment-3 is prepared as described in the literature: Belanger, P. C.; Dufresne, C.; Scheigetz, J.; Yang, D. N.; Springer, J. P.; Dmitrienko, G. I. *Can. J. Chem.* 1982, 60, 1019 and incorporated into the peptide by classical solution methods as described in "Peptide Synthesis", Second Edition, M Bodanszky, Y. S. Klausner, and M. A. Ondetti (1976).

EXAMPLE 13

H-Phenylalanyl-Lysyl-Alanyl-{(2S)-2-Amino-3-cyclohexylpropanoyl}-Nipecotyl(±)-Arginyl-OH

FAB+ MS: (M+H)+ = 785.

EXAMPLE 14

H-Phenylalanyl-Lysyl-Alanyl-{(2S)-2-Amino-3-cyclohexylpropanoyl}-{4-Aminobutanoyl}-Arginyl-OH

FAB+ MS: (M+H)+ =759.

EXAMPLE 15

(N-Methyl)Phenylalanyl-Lysyl-(Fragment-4)-{(2S)-2-Amino-3-cyclohexylpropanoyl}-Ψ{CH$_2$—NH}-DArginyl-OH Fragment-4 is prepared as described in the literature: Krstenansky, J. L.; Baranowdki, R. L.; Currie, B. L. *Biochem. Biophys. Res. Commun.* 1982, 109, 1368 and incorporated into the peptide by classical solution methods as described in "Peptide Synthesis", Second Edition, M. Bodanszky, Y. S. Klausner, and M. A. Ondetti (1976).

EXAMPLE 16

H-Phenylalanyl-Lysyl-Alanyl-{(2S)-2-Amino-3-cyclohexylpropanoyl}-{3-Aminopropanoyl}-Arginyl-OH

FAB+ MS: (M+H)+ =745.

EXAMPLE 17

H-Phenylalanyl-Lysyl-(N-Methyl)Alanyl-{(2S)-2-Amino-3-cyclohexylpropanoyl}-Leucyl-DAlanyl-Arginyl-OH

FAB+ MS: (M+H)+ =872.

EXAMPLE 18

(N-Methyl)Phenylalanyl-Lysyl-(N-Methyl)Alanyl-{(2R)-2-Amino-3-cyclohexylpropanoyl}-{(2S)-2-Amino-3-cyclohexylpropanoyl}-{(2R)-2-Amino-3-cyclohexylpropanoyl}OH

EXAMPLE 19

H-Phenylalanyl-Lysyl-Alanyl-{(2S)-2-Amino-3-cyclohexylpropanoyl}-{3-Aminopropanoyl}-DArginyl-OH

FAB+ MS: (M+H)+ =745.

EXAMPLE 20

H-phenylalanyl-Lysyl-{3-Aminopropanoyl}-Leucyl-DAlanyl-Arginyl-OH

FAB+ MS: (M+H)+ =705.

EXAMPLE 21

(N-Methyl)Phenylalanyl-Lysyl-(Fragment-5)-{(2S)-2-Amino-3-cyclohexylpropanoyl}-Ψ{CH$_2$—NH}-DArginyl-OH Fragment-5 is prepared as described in the literature: Attwood, M. R.; Francis, R. J.; Hassall, C. H.; Krohn, A.; Lawton, G.; Natoff, I. L.; Nixon, J. S.; Redshaw, S.; Thomas, W. A. *FEBS Lett.* 1984, 165, 201 and incorporated into the peptide by classical solution methods as described in "Peptide Synthesis", Second Edition, M. Bodanszky, Y. S. Klausner, and M. A. Ondetti (1976).

EXAMPLE 22

H-Phenylalanyl-Lysyl-{6-Aminohexanoyl}-Leucyl-DAlanyl-Arginyl-OH

FAB+ MS: (M+H)+ =747.

EXAMPLE 23

H-Phenylalanyl-Lysyl-Alanyl-(N-Methyl)Alanyl-Leucyl-DAlanyl-Arginyl-OH

FAB+ MS: (M+H)+ =872.

EXAMPLE 24

(N-Methyl)Phenylalanyl-Lysyl-(Fragment-6)-{(2S)-2-Amino-3-cyclohexylpropanoyl}-Ψ{CH$_2$—NH}-DArginyl-OH Fragment-6 is prepared as described in the literature: (a) Nagai, U.; Sato, K. *Tetrahedron Lett.* 1985, 647; (b) Baldwin, J.; Lee, E. *Tetrahedron Lett.* 1986, 42, 6551 and incorporated into the peptide by classical solution methods as described in "Peptide Synthesis", Second Edition, M Bodanszky, Y S Klausner, and M. A. Ondetti (1976).

EXAMPLE 25

H-Lysyl-Alanyl-(N-Methyl)Alanyl-{(2S)-2-Amino-3-cyclohexylpropanoyl}-Leucyl-DAlanyl-Arginyl-OH

FAB+ MS: (M+H)+ =878.

EXAMPLE 26 (Sequence ID NO. 2)

(N-Methyl)Phenylalanyl-Lysyl-Alanyl-{(2S)-2-Amino-3-cyclohexylpropanoyl}-Alanyl-(N-Methyl)Alanyl-Arginyl-OH

FAB+ MS: (M+H)+ =844.

EXAMPLE 27

(N-Methyl)Phenylalanyl-Lysyl-(N-Hydroxy)Asparaginyl-{(2R)-2-Amino-3-cyclohexylpropanoyl}-{(2S)-2-Amino-3-cyclohexylpropanoyl}-Ψ{CH$_2$-NH}-DArginyl-OH

EXAMPLE 28

(N-2-Phenethyl)Lysyl-Alanyl-{(2S)-2-Amino-3-cyclohexylpropanoyl}-Alanyl-(N-Methyl)Alanyl-Arginyl-OH

FAB+ MS: (M+H)+ =787.

EXAMPLE 29

(N-Isopropyl)Phenylalanyl-Lysyl-Alanyl-{(2S)-2-Amino-3-cyclohexylpropanoyl}-Alanyl-(N-Methyl)Alanyl-Arginyl-OH

FAB+ MS: (M+H)+ =872.

EXAMPLE 30

(N-Methyl)Phenylalanyl-Lysyl-Glycyl-Ψ{S(O$_2$)—NH}-{(2R)-2-Amino-3-cyclohexylpropanoyl}-{(2S)-2-Amino-3cyclohexylpropanoyl}-Ψ{CH$_2$—NH}-DArginyl-OH

EXAMPLE 31

H-Phenylalanyl-Lysyl-{(3R/S)-1,2,3,4-Tetrahydroisoquinolin-3-carbonyl}-{(2R)-2-Amino-3-cyclohexylpropanoyl}-{(2S)-2-Amino-3-cyclohexylpropanoyl}-DArginyl-OH FAB+ MS: (M+H)+ =915 Amino Acid Anal.: Phe (0.97), Lys (1.00), Cha (1.95), Arg (1.04).

EXAMPLE 32

H-Phenylalanyl-Lysyl-{(3R/S)-1,2,3,4-Tetrahydroisoquinolin-3-carbonyl}-{(2R)-2-Amino-3-cyclohexylpropanoyl}-{(2S)-2-Amino-3-cyclohexylpropanoyl}-DArginyl-OH FAB+ MS: (M+H)+ =915 Amino Acid Anal.: Phe (0.98), Lys (1.02), Cha (1.88), Arg (1.04).

EXAMPLE 33

(N-Methyl)Phenylalanyl-Phenylalanyl-(N-Methyl)Alanyl-{(2R)-2-Amino-3-cyclohexylpropanoyl}-{(2S)-2-Amino-3-cyclohexylpropanoyl}-DArginyl-OH

EXAMPLE 34

(N-Methyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH FAB+ MS: (M+H)+ =855 Amino Acid Anal.: Ala (0.89), Lys (1.07), Cha (2.05), Arg (1.06).

EXAMPLE 35

(N-Ethyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH FAB+ MS: (M+H)+ =869 Amino Acid Anal.: Lys (1.00), Cha (1.98), Arg (1.01)

EXAMPLE 36

(N-Methyl)Phenylalanyl-Lysyl-Prolyl-$\Psi${C≡C}-{(2R)-2-Amino-3-cyclohexylpropanoyl}-{(2S)-2-Amino-3-cyclohexylpropanoyl}-DArginyl-OH The Boc-Prolyl-$\Psi${C≡C}-{(2R)-2-Amino-3-cyclohexylpropanoyl}-OH alkyne isostere is prepared in analogy to the literature (van Marsenile, M.; Gysen, C.; Tourwe, D.; van Binst, G. *Bull. Soc. Chim. Belg.*, 1986, 108, 825.) and incorporated into the peptide by classical solution methods as described in "Peptide Synthesis", Second Edition, M. Bodanszky, Y. S. Klausner, and M. A. Ondetti (1976).

EXAMPLE 37

H-Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH FAB+ MS: (M+H)+ =841 Amino Acid Anal.: Phe (0.99), Lys (1.01), Cha (1.98), Arg (1.01).

EXAMPLE 38

H-Phenylalanyl-Lysyl-{3-aminomethylbenzoyl}-{(2R/S)-2-Amino-5-phenylpentanoyl}-DArginyl-OH Commercially available 3-cyanobenzoic acid was hydrogenated in the presence of palladium on charcoal in methanol to yield 3-aminomethylbenzoic acid. This was reacted with Boc-ON to obtain Boc-aminomethylbenzoic acid and incorporated into the peptide by solid phase peptide synthesis methodology as described in Example 1 and isolated according to the procedures described in Example 2.

FAB+ MS: (M+H)+ =758.

EXAMPLE 39

(N-Methyl)Phenylalanyl-Lysyl-Prolyl-$\Psi${C(=S)—NH}-{(2R)-2-Amino-3-cyclohexylpropanoyl}-{(2S)-2-Amino-3-cyclohexylpropanoyl}-DArginyl-OH The Boc-Prolyl-$\Psi${C(=S)—NH}-{(2R)-2-Amino-3-cyclohexylpropanoyl}-OH dipeptide is prepared in analogy to the literature (Maziak, L.; Lajoie, G.; Belleau, B. *J. Am. Chem. Soc.*, 1986, 108, 182.) and incorporated into the peptide by classical solution methods as described in "Peptide Synthesis", Second Edition, M. Bodanszky, Y. S. Klausner, and M. A. Ondetti (1976).

EXAMPLE 40

H-Phenylalanyl-Lysyl-Alanyl-{(2R)-2-Amino-3-cyclohexylpropanoyl}-{(N-Methyl)(2S)-2-Amino-3cyclohexylpropanoyl}-DArginyl-OH

FAB+ MS: (M+H)+ =841.

EXAMPLE 41

(N-Allyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH FAB+ MS: (M+H)+ =881 Amino Acid Anal.: Lys (0.99), Cha (1.97), Arg (1.01).

EXAMPLE NO. 42

(N-Methyl)Phenylalanyl-Lysyl-Prolyl-$\Psi${CH$_2$—O}-{(2R)-2-Amino-3-cyclohexylpropanoyl}-{(2S)-2-Amino-3-cyclohexylpropanoyl}-DArginyl-OH The Boc-Prolyl-$\Psi${CH$_2$—O}-{(2R)-2-Amino-3-cyclohexylpropanoyl}-OH dipeptide is prepared in analogy to the literature (Rubini, E.; Gilson, C.; Selinger, Z.; Chorev, M. *Tetrahedron.*, 1986, 42, 6039.) and incorporated into the peptide by classical solution methods as described in "Peptide Synthesis", Second Edition, M Bodanszky, Y. S. Klausner, and M. A. Ondetti (1976).

EXAMPLE 43

H-Phenylalanyl-Lysyl-{(2S)-Azetidine-2-carbonyl}-{(2R)-2-Amino-3-cyclohexylpropanoyl}-{(2S)-2-Amino-3-cyclohexylpropanoyl}-DArginyl-OH FAB+ MS: (M+H)+ =839 Amino Acid Anal.: Phe (0.93), Lys (1.01), Cha (2.08), Arg (1.07).

EXAMPLE 44

H-Phenylalanyl-Lysyl-{(2S)-3,3-Dimethyl-thiazolidine-2-carbonyl}-{(2R)-2-Amino-3-cyclohexylpropanoyl}-{(2S)-2-Amino-3-cyclohexylpropanoyl}-DArginyl-OH FAB+ MS: (M+H)+ =899 Amino Acid Anal.: Phe (0.93), Lys (0.99), Cha (2.01), Arg (1.08).

EXAMPLE 45

(N-Methyl)Phenylalanyl-Arginyl-(N-Methyl)Alanyl-{(2R)-2-Amino-3-cyclohexylpropanoyl}-{(2S)-2-Amino-3-cyclohexylpropanoyl}-DArginyl-OH

EXAMPLE 46

(N,N-Dimethyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH FAB+ MS: (M+H)+ =869 Amino Acid Anal.: Lys (0.96), Cha (2.11), Arg (1.04)

EXAMPLE 47

(N-Isopropyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH FAB+ MS: (M+H)+ =883 Amino Acid Anal.: Lys (0.99), Cha (1.92), Arg (1.01).

EXAMPLE 48

(N-Methyl)Phenylalanyl-Lysyl-Prolyl-$\Psi${CH$_2$—S}-{(2R)-2-Amino-3-cyclohexylpropanoyl}-{(2S)-2-Amino-3-cyclohexylpropanoyl}-DArginyl-OH The Boc-Prolyl-$\Psi${CH$_2$—S}-{(2R)-2-Amino-3-cyclohexylpropanoyl}-OH dipeptide is prepared in analogy to the literature (Spatola, A.; Anwer, M.; Rockwell, A.; Gierasch, L. *J. Am. Chem. Soc.,* 1986, 108, 825.) and incorporated into the peptide by classical solution methods as described in "Peptide Synthesis", Second Edition, M. Bodanszky, Y. S. Klausner, and M. A. Ondetti (1976).

EXAMPLE 49

(N,N-Diethyl)Phenylalanyl-Lysyl-(N-Methyl)Alanyl-{(2R)-2-Amino-3-cyclohexylpropanoyl}-{(2S)-2-Amino-3-cyclohexylpropanoyl}-DArginyl-OH FAB+ MS: (M+H)+ =897 Amino Acid Anal.: Lys (0.94), Cha (1.97), Arg (1.06).

EXAMPLE 50

H-Phenylalanyl-Norleucyl-(N-Methyl)Alanyl-{(2R)-2-Amino-3-cyclohexylpropanoyl}-{(2S)-2-Amino-3-cyclohexylpropanoyl}-DArginyl-OH FAB+ MS: (M+H)+ =826 Amino Acid Anal.: Phe (0.97), Nle (1.01), Cha (1.83), Arg (1.03).

EXAMPLE 51

N-Boc-(N-Methyl)Phenylalanyl-Lysyl (N-epsilon-Boc)-Prolyl-{(2R)-2-Amino-3-cyclohexylpropanoyl-OH Commercially available D-Phenylalanine methyl ester hydrochloride (12 g) was hydrogenated using 5% rhodium on carbon (1.2 g) in 250 mL of methyl alcohol to yield (2R)-2-amino-3-cyclohexyl propanoic acid methyl ester hydrochloride in 97% yield. This (5.0 g, 18.4 mmole) was coupled with Boc-L-Proline (3.97 g, 18.4 mmole) by using standard methods [(1-hydroxybenzotriazole monohydrate (HOBt) (2.74 g, 20 mmole), N-Methylmorpholine (NMM) (2.23 mL, 20 mmole) and 1-(3-dimethylaminopropyl-3-ethylcarbodiimide hydrochloride (EDC) (3.89 g, 20 mmole) by the methods described in "Peptide Synthesis", Second Edition, Bodanszky, M.; Klausner, Y. S. and Ondetti, M. A., (1976) in 71% yield. The Boc-group was cleaved, and the obtained prolyl-(2R)-2-amino-3-cyclohexylpropanoic acid methyl ester hydrochloride was reacted with N-alpha-Cbz-N-epsilon-Boc-Lysine in quantitative yield according to the method mentioned above. The N-alpha-Cbz group was removed by hydrogenolysis (20%-palladium on charcoal 10% w/w) in acetic acid-isopropanol, and the obtained product was coupled with Boc-(N-Methyl)Phenylalanine by the method described above to obtain N-Boc-(N-Methyl)Phenylalanyl-Lysyl(N-epsilon-Boc)-Prolyl-{(2R)-2-Amino-3-cyclohexylpropanoic acid methyl ester in quantitative yield. Finally, the methyl ester (7.33 g, 9.5 mmole) was saponified by treatment with 1.5 equivalent molar of lithium hydroxide (598 mg, 14.25 mmole) in 115 mL of methanol-water (2:1) mixture to obtain the title compound in 83% yield.

FAB+ MS: (M+H)+ =758

This fully protected peptide was used to prepared the compounds (Examples 139, 140, 142, 143, and 167).

EXAMPLE 52

H-Phenylalanyl-Lysyl-Alanyl-{(2R)-2-Amino-3-cyclohexylpropanoyl}-{(3R/S)-1,2,3,4-Tetrahydroisoquinolin-3-carbonyl }-DArginyl-OH

FAB+ MS: (M+H)+ =833.

EXAMPLE 53

H-Phenylalanyl-Lysyl-Alanyl-{(2R)-2-Amino-3-cyclohexylpropanoyl}-{(3R/S)-1,2,3, 4-Tetrahydroisoquinolin-3-carbonyl}-DArginyl-OH

FAB+ MS: (M+H)+ =833.

EXAMPLE 54

(N-Methyl)Phenylalanyl-Lysyl-Phenylalanyl-{(2R)-2 -Amino-3-cyclohexylpropanoyl}-{(2S)-2-Amino-3-cyclohexylpropanoyl}-$\Psi$(CH$_2$NH)-DArginyl-OH

EXAMPLE 55

N-Acetyl-Phenylalanyl-Lysyl-(N-Methyl)Alanyl-{(2R)-2 -Amino-3-cyclohexylpropanoyl}-{(2S)-2-Amino-3-cyclohexylpropanoyl}-DArginyl-OH;

The trifluoroacetic acid salt of H-Phenylalanyl-Lysyl-(N-epsilon-Cbz)-(N-Methyl)Alanyl-{(2R)-2-Amino-3-cyclohexylpropanoyl}-{(2S)-2-Amino-3-cyclohexylpropanoyl}-DArginyl(N-guanidino-Tos)-OResin (0.56 g) was prepared according to the procedure described in Example 1. The peptide-resin obtained was washed with 10%-diisopropylethylamine (DIEA) in methylene chloride (3×15 mL, 45 seconds each) and methylene chloride (4×15 mL). 10%-DIEA in methylene chloride (15 mL) was introduced into the reaction vessel and acetic anhydride (0.47 mL, 5 mmole) was added. It was reacted at room temperature for 1 hour and repeated if necessary (until the Kaiser test was negative). The N-acetyl-peptide resin was treated with HF and anisole to yield 130 mg of dried powder. A portion of the powder was purified by HPLC, using the procedures described in Example 2 to yield the pure title product.

FAB+ MS: (M+H)+ =883.

EXAMPLE 56

H-Phenylalanyl-Lysyl-Sarcosyl-{(2R)-2-Amino-3-cyclohexylpropanoyl}-{(2S)-2-Amino-3-cyclohexylpropanoyl}-DArginyl-OH FAB+ MS: (M+H)+ =827 Amino Acid Anal.: Phe (0.94), Cha (1.99), Lys (0.95), Arg (1.11).

EXAMPLE 57

(N-Methyl)Phenylalanyl-Lysyl-$\Psi${C(=O)—S }-Glycyl-{(2R)-2-Amino-3-cyclohexylpropanoyl }-{(2 S)-2-Amino-3-cyclohexylpropanoyl}-DArginyl-OH The N-alpha-Boc-Lysyl(N-epsilon-Cbz)-$\Psi${C(=O)—S}-Glycyl-OH dipeptide is prepared by standard coupling of N-alpha-Boc-N-epsilon-Cbz-Lysine mixed anhydride with thiolactic acid and incorporated into the peptide by classical solution methods as described in "Peptide Synthesis", Second Edition, M. Bodanszky, Y. S. Klausner, and M. A. Ondetti (1976).

EXAMPLE 58

(N-Methyl)Phenylalanyl-Lysyl-{(2S)-Azetidine-2-carbonyl}-{(2R)-2-Amino-3-cyclohexylpropanoyl}-{(2S)-2-Amino-3-cyclohexylpropanoyl}-DArginyl-OH FAB+ MS: (M+H)+ =853 Amino Acid Anal.: MePhe (0.92), Lys (1.00), Cha (1.97), Arg (2.42).

EXAMPLE 59

(N-Methyl)Phenylalanyl-Lysyl-{(2R)-3,3-Dimethylthiazolidine-2-carbonyl}-{(2R)-2-Amino-3-cyclohexylpropanoyl}-{(2S)-2-Amino-3-cyclohexylpropanoyl}-DArginyl-OH

FAB+ MS: (M+H)+ =913.

EXAMPLE 60

(N-Methyl)Phenylalanyl-Lysyl-Ψ{CH$_2$C(=O)—S}-Glycyl-{(2R)-2-Amino-3-cyclohexylpropanoyl}-{(2S)-2-Amino-3-cyclohexylpropanoyl}-DArginyl-OH The Boc-Lysyl(N-epsilon-Cbz)-Ψ{CH$_2$C(=O)—S}-Glycyl-OH dipeptide is prepared by a standard coupling of N-Boc-Lysine-(N-epsilon-Cbz)-Ψ{CH$_2$C(=O)-}—OH mixed anhydride with thiolactic acid and incorporated into the peptide by classical solution methods as described in "Peptide Synthesis", Second Edition, M. Bodanszky, Y. S. Klausner, and M. A. Ondetti (1976).

EXAMPLE 61

(N-Methyl)Phenylalanyl-Lysyl-(N-Methyl)Phenylalanyl-{(2R)-2-Amino-3-cyclohexylpropanoyl}-{(2S)-2-Amino-3-cyclohexylpropanoyl}-DArginyl-OH FAB+ MS: (M+H)+ =931 Amino Acid Anal.: Lys (0.97), Cha (1.93), Arg (1.03).

EXAMPLE 62

(N-Methyl)Phenylalanyl-Norleucyl-(N-Methyl)Alanyl-{(2R)-2-Amino-3-cyclohexylpropanoyl}-{(2S)-2-Amino-3-cyclohexylpropanoyl}-DArginyl-OH FAB+ MS: (M+H)+ =840 Amino Acid Anal.: Nle (1.02), Cha (1.95), Arg (1.00).

EXAMPLE 63

(N-Methyl)Phenylalanyl-Lysyl-Ψ{CH=CH}-Glycyl-{(2R)-2-Amino-3-cyclohexylpropanoyl}-{(2S)-2-Amino-3-cyclohexylpropanoyl }-DArginyl-OH The N-alpha-Boc-Lysyl(N-epsilon-Cbz)-Ψ{CH=CH}-Glycyl-OH dipeptide isostere is prepared in analogy to the literature (Spaltenstein, A.; Carpino, P.; Miyake, F.; Hopkins, P *Tetrahedron Lett.,* 1986, 27, 2095) and incorporated into the peptide by classical solution methods as described in "Peptide Synthesis", Second Edition, M. Bodanszky, Y. S. Klausner, and M. A. Ondetti (1976).

EXAMPLE 64

H-Phenylalanyl-(N-alpha-Methyl)Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =867 Amino Acid Anal.: Phe (0.97), Pro (1.14), Cha, MeLys (3.08), Arg (1.03).

EXAMPLE 65

(N-Methyl)Phenylalanyl-Lysyl-D (N-Methyl)Phenylalanyl-{(2R)-2-Amino-3-cyclohexylpropanoyl}-{(2S)-2-Amino-3-cyclohexylpropanoyl}-DArginyl-OH FAB+ MS: (M+H)+ =931 Amino Acid Anal.: Lys (0.97), Cha (1.98), Arg (1.03).

EXAMPLE 66

(N-Methyl)Phenylalanyl-Lysyl-Prolyl-Ψ{C(=O)—CH$_2$}-{(2R)-2-Amino-3-cyclohexylpropanoyl}-{(2S)-2-Amino-3-cyclohexylpropanoyl}-DArginyl-OH The Boc-Prolyl-Ψ{C(=O)—CH$_2$}-{(2R)-2-Amino-3-cyclohexylpropanoyl}-OH dipeptide isostere is prepared in analogy to the literature (McMurray, J.; Dyckes, D. *J. Org. Chem.,* 1985, 50, 1112.) and incorporated into the peptide by classical solution methods as described in "Peptide Synthesis", Second Edition, M Bodanszky, Y, S. Klausner, and M. A. Ondetti (1976).

EXAMPLE 67

H-{(2'S,3S)-3Amino-2-oxo-1-pyrrolidine-[2'-(6'-amino)-hexanoyl]}-Prolyl-{(2R)-2-Amino-3-cyclohexylpropanoyl}-{(2S)-2-Amino-3-cyclohexylpropanoyl}-DArginyl-OH FAB+ MS: (M+H)+ =789 Amino Acid Anal.: Pro (0.97), Cha (2.03), Arg (1.03).

EXAMPLE 68

H-{(2'S,3R)-3-Amino-2-oxo-1-pyrrolidine-[2'-(6'-amino)hexanoyl]}-Prolyl-{(2R)-2-Amino-3-cyclohexylpropanoyl}-{(2S)-2-Amino-3-cyclohexylpropanoyl}-DArginyl-OH FAB+ MS: (M+H)+ =789 Amino Acid Anal.: Pro (0.93), Cha (2.23), Arg (1.07).

EXAMPLE 69

(N-Methyl)Phenylalanyl-Lysyl-{(2S)-2-Amino-3-cyclohexylpropanoyl}-{(2R)-2-Amino-3-cyclohexylpropanoyl}-{(2S)-2-Amino-3-cyclohexylpropanoyl}-Ψ(CH$_2$NH)-DArginyl-OH

EXAMPLE 70

(N-Methyl)Phenylalanyl-Lysyl-Prolyl-{(2R)-2-Amino-3-cyclohexylpropanoyl}-{(2S)-2-Amino-3-cyclohexylpropanoyl}-(N-Methyl)Arginyl-OH FAB+ MS: (M+H)+ =881 Amino Acid Anal.: Lys (0.92), Pro (1.09), Cha (1.91).

EXAMPLE 71

H-Phenylalanyl-Lysyl-{3-aminomethylbenzoyl}-{(2S)-2-Amino-3-cyclohexylpropanoyl}-DArginyl-OH

FAB+ MS: (M+H)+ =736.

EXAMPLE 72

(N-Methyl)Phenylalanyl-Lysyl-Prolyl-Ψ{CH(OH)—CH$_2$}-{(2R)-2-Amino-3-cyclohexylpropanoyl}-{(2S)-2-Amino-3-cyclohexylpropanoyl}-DArginyl-OH The Boc-Prolyl-Ψ{C(=O)—CH$_2$}-{(2R)-2-Amino-3-cyclohexylpropanoyl}-OH dipeptide isostere (Example No. 66) is reduced to Boc-Prolyl-Ψ{CH(OH)—CH$_2$}-{(2R)-2-Amino-3-cyclohexylpropanoyl}-OH with sodium borohydride in methanol and incorporated

EXAMPLE 73

(N-Methyl)Phenylalanyl-(N-alpha,N-epsilon,Dimethyl)Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+=895 Amino Acid Anal.: MePhe (1.01), Cha (1.88), Arg (1.00), Pro (1.01).

EXAMPLE 74

(N-Methyl)Phenylalanyl-(N-alpha,N-delta,Dimethyl)Ornithyl-Prolyl-{(2R)-2-Amino-3-cyclohexylpropanoyl}-{(2S)-2-Amino-3-cyclohexylpropanoyl}-DArginyl-OH FAB+ MS: (M+H)+=881 Amino Acid Anal.: MePhe (0.88), Pro (1.07), Cha (1.98), Arg (1.00).

EXAMPLE 75

(N-Methyl)Phenylalanyl-Lysyl-Prolyl-Ψ{C(=CH$_2$)—CH$_2$}-{(2R)-2-Amino-3-cyclohexylpropanoyl}-{(2S)-2-Amino-3-cyclohexylpropanoyl}-DArginyl-OH The Boc-Prolyl-Ψ{C(=CH$_2$)—CH$_2$}-{(2R)-2-Amino-3-cyclohexylpropanoyl}-OH isostere is prepared by condensing methylenetriphenylphosphorane and Boc-Prolyl-Ψ{C(=O)—CH$_2$}-{(2R)-2-Amino-3-cyclohexylpropanoyl}-OH, and incorporated into the peptide by classical solution methods as described in "Peptide Synthesis", Second Edition, M. Bodanszky, Y. S. Klausner, and M. A. Ondetti (1976).

EXAMPLE 76

(N-Methyl)Phenylalanyl-Lysyl-{3-Aminopropanoyl}-{(2R)-2-Amino-3-cyclohexylpropanoyl}-{(2S)-2-Amino-3-cyclohexylpropanoyl}-DArginyl-OH FAB+ MS: (M+H)+=841 Amino Acid Anal.: MePhe (1.04), Lys (0.99), Cha (1.87), Arg (1.01).

EXAMPLE 77

(N-Methyl)Phenylalanyl-Lysyl-D(N-Methyl)Alanyl-{(2R)-2-Amino-3-cyclohexylpropanoyl}-{(2S)-2-Amino-3-cyclohexylpropanoyl}-DArginyl-OH FAB+ MS: (M+H)+=855 Amino Acid Anal.: MePhe (1.01), Lys (0.96), Cha (1.90), Arg (1.04).

EXAMPLE 78

(N-Methyl)Phenylalanyl-Lysyl-Ψ{C(=O)-N(OMe)}-Glycyl-{(2R)-2-Amino-3-cyclohexylpropanoyl}-{(2S)-2-Amino-3-cyclohexylpropanoyl}-DArginyl-OH The Boc-N(OMe)-Glycine is prepared as described in the literature (Ottenheijm, H.; Herscheid, J. *J. Chem. Rev.*, 1986, 86, 697.) and incorporated into the peptide by classical solution methods described in "Peptide Synthesis", Second Edition, M Bodanszky, Y. S. Klausner, and M. A. Ondetti (1976).

EXAMPLE 79

(N-Methyl)Phenylalanyl-Lysyl-Ψ{CH$_2$NH}-Prolyl-{(2R)-2-Amino-3-cyclohexylpropanoyl}-{(2S)-2-Amino-3-cyclohexylpropanoyl}-DArginyl-OH FAB+ MS: (M+H)+=853 Amino Acid Anal.: Cha (1.96), Arg (1.00).

EXAMPLE 80

(N-Methyl)Phenylalanyl-Lysyl-Prolyl-Ψ{CH$_2$NH}-{(2R)-2-Amino-3-cyclohexylpropanoyl}-{(2S)-2-Amino-3-cyclohexylpropanoyl}-DArginyl-OH FAB+ MS: (M+H)+=853 Amino Acid Anal.: Lys (0.52), Cha (0.98), Arg (1.00).

EXAMPLE 81

(N-Methyl)Phenylalanyl-Lysyl-Arginyl-{(2R)-2-Amino-3-cyclohexylpropanoyl}-{(2S)-2-Amino-3-cyclohexylpropanoyl}Ψ(CH2NH)-DArginyl-OH

EXAMPLE 82

(N-Methyl)Phenylalanyl-Lysyl-Sarcosyl-{(2R)-2-Amino-3-cyclohexylpropanoyl}-Phenylalanyl-DArginyl-OH FAB+ MS: (M+H)+=835 Amino Acid Anal.: Sar (0.56), MePhe (0.97), Phe (1.09), Cha (0.91), Lys (0.96), Arg (1.08).

EXAMPLE 83

(N-Methyl)Phenylalanyl-Lysyl-(N-Methyl)Alanyl-{(2R)-2-Amino-3-cyclohexylpropanoyl}-Phenylalanyl-DArginyl-OH FAB+ MS: (M+H)+=849 Amino Acid Anal.: MePhe (0.99), Phe (1.06), Cha (0.94), Lys (0.97), Arg (1.04).

EXAMPLE 84

(N-Methyl)Phenylalanyl-Lysyl-Prolyl-Ψ{PO(OH)—NH}-{(2R)-2-Amino-3-cyclohexylpropanoyl}-{(2S)-2-Amino-3-cyclohexylpropanoyl}-DArginyl-OH The Boc-Prolyl-Ψ{PO(OH)—NH}-{(2R)-2-Amino-3-cyclohexylpropanoyl}-OH dipeptide isostere is prepared in analogy to the procedure described in the literature (Bartlett, P.; Marlowe, C. *Biochemistry*, 1987, 26, 8554) and incorporated into the peptide by classical solution methods as described in "Peptide Synthesis", Second Edition, M. Bodanszky, Y. S. Klausner, and M. A. Ondetti (1976).

EXAMPLE 85

H-Phenylalanyl-Lysyl-Alanyl-{(3RS)-1,2,3,4-Tetrahydroisoquinolin-3-carbonyl}-{(2S)-2-Amino-3-cyclohexylpropanoyl}-DArginyl-OH

FAB+ MS: (M+H)+=833.

EXAMPLE 86

(N-Methyl)Phenylalanyl-Lysyl-Prolyl-{(2R)-2-Amino-3-cyclohexylpropanoyl}-(N-Methyl)Phenylalanyl-DArginyl-OH FAB+ MS: (M+H)+=875 Amino Acid Anal.: MePhe (1.74), Lys (0.71), Cha (0.94), Arg (1.00), Pro (1.00).

EXAMPLE 87

(N-Methyl)Phenylalanyl-Lysyl-Prolyl-Ψ{PO(OMe)-NH}-{(2R)-2-Amino-3-cyclohexylpropanoyl}-{(2S)-2-Amino-3-cyclohexylpropanoyl}-DArginyl-OH The Boc-Prolyl-Ψ{PO(OMe)-NH}-{(2R)-2-Amino-3-cyclohexylpropanoyl}-OH dipeptide isostere is prepared in analogy to the procedure described in the literature (Bartlett, P.; Marlowe, C. *Biochemistry*, 1987, 26, 8554) and incorporated into the peptide by classical solution methods as described in "Peptide Synthesis", Second Edition, M. Bodanszky, Y. S. Klausner, and M. A. Ondetti (1976).

EXAMPLE 88

(N-Methyl)Phenylalanyl-Lysyl-Prolyl-{(2R)-2-Amino-3-cyclohexylpropanoyl}-(N-Methyl)Phenylalanyl-Arginyl-OH FAB+ MS: (M+H)+ =875 Amino Acid Anal.: MePhe (1.65), Lys (0.64), Cha (1.88), Arg (0.98), Pro (1.02).

EXAMPLE 89

(N-Methyl)Phenylalanyl-Lysyl-Prolyl-{(2R)-2-Amino-3-cyclohexylpropanoyl}-Ψ{CH$_2$NH}-Phenylalanyl-DArginyl-OH FAB+ MS: (M+H)+ =847 Amino Acid Anal.: MePhe (1.05), Lys (0.92), Cha (1.88), Arg (1.04), Pro (0.96).

EXAMPLE 90

(N-Methyl)Phenylalanyl-Lysyl-Prolyl-Ψ{PO(NH-Me)—NH}-{(2R)-2-Amino-3-cyclohexylpropanoyl}-{(2S)-2-Amino-3-cyclohexylpropanoyl}-DArginyl-OH The Cbz-Prolyl-Ψ{PO(OH)-NH}-{(2R)-2-Amino-3-cyclohexylpropanoyl}-OBu$^t$ dipeptide isostere is prepared in analogy to the procedure described in the literature (Bartlett, P.; Marlowe, C. Biochemistry, 1987, 26, 8554), coupled with methyl amine and deprotected to give Cbz-Prolyl-Ψ{PO(NHMe)-NH}-{(2R)-2-Amino-3-cyclohexylpropanoyl}OH. Cbz-Prolyl-Ψ{PO(NH-Me)—NH}-{(2R)-2-Amino-3-cyclohexylpropanoyl}-OH is incorporated into the peptide by classical solution methods as described in "Peptide Synthesis", Second Edition, M Bodanszky, Y. S. Klausner, and M. A. Ondetti (1976).

EXAMPLE 91

(N-Methyl)Phenylalanyl-Lysyl-Prolyl-(2R)-2-Amino-3-cyclohexylpropanoyl}-(N-Methyl)Phenylalanyl-Ψ{CH$_2$NH}-Arginyl-OH FAB+ MS: (M+H)+ =861 Amino Acid Anal.: Pro (1.28), Lys (1.00), Cha (0.53).

EXAMPLE 92

(N-Methyl)Phenylalanyl-Lysyl-Prolyl-{(2R)-2-Amino-3-cyclohexylpropanoyl}-Phenylalanyl-Ψ{CH$_2$NH}-Arginyl-OH FAB+ MS: (M+H)+ =847 Amino Acid Anal.: Pro (1.00), Lys (0.96), Cha (1.04), MePhe (1.16).

EXAMPLE 93

(N-Methyl)Phenylalanyl-Lysyl-Prolyl-{(2R)-2-Amino-3-cyclohexylpropanoyl}-Phenylalanyl-Ψ(CH$_2$NH)-DArginyl-NHNH$_2$ The peptide-resin is prepared in analogy to Example 1 stopping on Agenda A at step 5 to afford N-Boc-(N-Methyl)Phenylalanyl-Lysyl(N-epsilon-Cbz)-Prolyl-{(2R)-2-Amino-3-cyclohexylpropanoyl}-Phenylalanyl-Ψ(CH$_2$NH)-DArginyl (N-guanidino-Tos)-Merrifield Resin. This is treated with hydrazine by the methods described in "Solid Phase Peptide Synthesis", 2nd edition, Stewart, J. M.; Young, J. D. Pierce Chemical Co.: Rockford, Ill., 1984: p 91 to afford the title compound.

EXAMPLE 94

H-Phenylalanyl-{(3S)-3,7-Diaminoheptanoyl}-Prolyl-{(2R)-2-Amino-3-cyclohexylpropanoyl}-Phenylalanyl-DArginyl-OH

FAB+ MS: (M+H) + =861.

EXAMPLE 95

H-Phenylalanyl-Lysyl-Alanyl-{(N-Methyl)-(2R)-2-Amino-3-cyclohexylpropanoyl}-{(2S)-2-Amino-3-cyclohexylpropanoyl}-DArginyl-OH

FAB+ MS: (M+H)+ =841.

EXAMPLE 96

(N-Methyl)Phenylalanyl-Lysyl-Prolyl-Ψ{PO(NMe$_2$)—NH}-{(2R)-2-Amino-3-cyclohexylpropanoyl}-{(2S)-2-Amino-3-cyclohexylpropanoyl}-DArginyl-OH The Cbz-Prolyl-Ψ{PO(OH)—NH}-{(2R)-2-Amino-3-cyclohexylpropanoyl}-OBu$^t$ dipeptide isostere is prepared in analogy to the procedure described in the literature (Bartlett, P.; Marlowe, C. Biochemistry, 1987, 26, 8554), coupled with dimethyl amine and deprotected to give Cbz-Prolyl-Ψ{PO(NMe$_2$)-NH}-{(2R)-2-Amino-3-cyclohexylpropanoyl}-OH. Cbz-Prolyl-Ψ{PO(NMe$_2$)—NH}-{(2R)-2-Amino-3-cyclohexylpropanoyl}-OH is incorporated into the peptide by classical solution methods as described in "Peptide Synthesis", Second Edition, M. Bodanszky, Y. S. Klausner, and M. A. Ondetti (1976).

EXAMPLE 97

(N-Methyl)Phenylalanyl-(R/S)Lysyl-Ψ{CH$_2$NH}-Prolyl-{(2R)-2-Amino-3-cyclohexylpropanoyl}-Phenylalanyl-DArginyl-OH FAB+ MS: (M+H)+ =847 Amino Acid Anal.: Phe (1.00), Cha (0.97), Arg (1.00).

EXAMPLE 98

(N-Methyl)Phenylalanyl-(R/S)Lysyl-Ψ{CH$_2$NH}-Prolyl-{(2R)-2-Amino-3-cyclohexylpropanoyl}-Phenylalanyl-DArginyl-OH FAB+ MS: (M+H)+ =847 Amino Acid Anal.: Phe (1.00), Cha (0.97), Arg (1.00).

EXAMPLE 99

(N-Methyl)Phenylalanyl-Lysyl-Prolyl-Ψ{PO(NH$_2$)-NH}-{(2R)-2-Amino-3-cyclohexylpropanoyl}-{(2S)-2-Amino-3-cyclohexylpropanoyl}-DArginyl-OH The Cbz-Prolyl-Ψ{PO(OH)-NH}-{(2R)-2-Amino-3cyclohexylpropanoyl}-OBu$^t$ dipeptide isostere is prepared in analogy to the procedure described in the literature (Bartlett, P.; Marlowe, C. Biochemistry, 1987, 26, 8554), coupled with ammonia and deprotected to give Cbz-Prolyl-Ψ{PO(NH$_2$)-NH}-{(2R)-2-Amino-3-cyclohexylpropanoyl}-OH. Cbz-Prolyl-Ψ{PO(NH$_2$)-NH}-{(2R)-2-Amino-3-cyclohexylpropanoyl}-OH is incorporated into the peptide by classical solution methods as described in "Peptide Synthesis", Second Edition, M. Bodanszky, Y. S. Klausner, and M. A. Ondetti (1976).

EXAMPLE 100

(N-Methyl)Phenylalanyl-Lysyl-{4-Aminobutanoyl}-Phenylalanyl-DArginyl-OH

FAB+ MS: (M+H)+=696 Amino Acid Anal.: MePhe (0.90), Phe (1.02), Lys (1.06), Arg (1.01).

EXAMPLE 101

N-Boc-(N-Methyl)Phenylalanyl-Lysyl(N-epsilon-Boc)-Prolyl{(2R)-2-Amino-3-cyclohexylpropanoyl-Phenylalanyl-OH N-Boc-(N-Methyl)Phenylalanyl-Lysyl (N-epsilon-Boc)-Prolyl-{(2R)-2-Amino-3-cyclohexylpropanoic acid (Example 51) (1.5 g, 2 mole) was reacted with H-phenylalanine methyl ester hydrochloride in tetrahydrofuran by the mixed anhydride method (isobutylchloroformate and N-methylmorpholine) as described in "Peptide Synthesis", second Edition, Bodanszky, M.; Klausner, Y. S. and Ondetti, M. A., (1976) to obtain N-Boc-(N-Methyl)Phenylalanyl-Lysyl(N-epsilon-Boc)-Prolyl-{(2R)-2-Amino-3-cyclohexylpropanoyl}-Phenylalanine Methyl ester in quantitative yield. The methyl ester (1.7 g, 1.8 mmole) was hydrolyzed using 1.5 equivalent mole of lithium hydroxide (160 mg, 2.7 mmole) in 20 mL of methanol and water (2:1) using to the procedures described in Example 51 to yield the title compound in 99% yield.

FAB+ MS: (M+H)+=905

This fully protected peptide was used to prepare the compounds (Examples 170, 171, 174, and 175).

EXAMPLE 102

(N-Methyl)Phenylalanyl-Lysyl-Ψ{CH$_2$C(=O)—O}-Glycyl-{(2R)-2-Amino-3-cyclohexylpropanoyl}-{(2S)-2-Amino-3-cyclohexylpropanoyl}-DArginyl-OH The Boc-Lysyl(Cbz)-Ψ{CH$_2$C(=O)}-OH is prepared by the Arndt-Eistert procedure as described in the literature (Wakamiya, T.; Uratani, H.; Teshima, T.; Shiba, T. Bull. Chem. Soc. Jpn. 1975, 48, 2401. ) Boc-Lys(Cbz)-Ψ{CH$_2$C(=O)-O}-Glycyl-OH is prepared in analogy to Example 60 and incorporated into the peptide by classical solution methods as described in "Peptide Synthesis", Second Edition, M Bodanszky, Y. S. Klausner, and M. A. Ondetti (1976).

EXAMPLE 103

(N-Methyl)Phenylalanyl-Lysyl-Prolyl-Ψ{CH$_2$NH}-(2R)-2-Amino-3-cyclohexylpropanoyl}-Phenylalanyl-DArginyl-OH

FAB+ MS: (M+H)+=847.

EXAMPLE 104

(N-Methyl)Phenylalanyl-Lysyl-{(N-Methyl)-7-aminoheptanoyl}-Phenylalanyl-DArginyl-OH This compound was prepared in analogy to Example 115.

FAB+ MS: (M+H)+=752 Amino Acid Anal.: MePhe (0.90), Phe (1.05), Lys (0.93), Arg (1.11).

EXAMPLE 105

(N-Methyl)Phenylalanyl-Lysyl-Prolyl-{(2R)-2-Amino-3-cyclohexylpropanoyl}-{(2S)-2-Amino-3-cyclohexylpropanoyl}-Ψ{CH$_2$—N(CH$_2$CH$_2$C$_6$H$_5$)}-DArginyl-OH Boc-(N-Methyl)Phenylalanyl-Lysyl(N-epsilon-Cbz)-Prolyl-{(2R)-2-Amino-3-cyclohexylpropanoyl}-{(2S)-2-Amino-3-cyclohexylpropanoyl}-Ψ[CH$_2$NH]-DArginyl(guanidino-Tos)Merrified resin is prepared in Example 1 stopping on Agenda A at step 2. Commercially available phenylacetaldehyde (3.5 equivalent mole) in DMF containing 0.1% glacial acetic acid is added, followed by sodium cyanoborohydride (10 equivalent mole). The reaction is allowed to proceed at room temperature for 1 hour. After the peptide resin obtained is washed with DMF (3 times) and methylene chloride (3 times), the synthetic protocol is resumed on Agenda A at step 2. The peptide-resin is then treated using the methods described in Example 2.

EXAMPLE 106

H-Phenylalanyl-Lysyl-Prolyl-{(2R)-2-Amino-3-cyclohexylpropanoyl}-{(3S)-3-Amino-4-phenyl-butanoyl}-DArginyl-OH

FAB+ MS: (M+H)+=861.

EXAMPLE 107

H-Phenylalanyl-Lysyl-Prolyl-{(3R)-3-Amino-4-cyclohexylbutanoyl}-Phenylalanyl-DArginyl-OH

FAB+ MS: (M+H)+=861.

EXAMPLE 108

(N-Methyl)Phenylalanyl-Lysyl-Prolyl-Ψ(CH$_2$NH)-{(2R)-2-Amino-3-cyclohexylpropanoyl}-{(2S)-2-Amino-3-cyclohexylpropanoyl}-DPhenylalanyl-OH

EXAMPLE 109

H-{(3S)-3-amino-4-phenylbutanoyl}-Lysyl-prolyl-{(2R)-2-Amino-3-cyclohexylpropanoyl}-Phenylalanyl-DArginyl-OH

FAB+ MS: (M+H)+=861.

EXAMPLE 110

H-Phenylalanyl-Lysyl-Prolyl-{(2R)-2-Amino-3-cyclohexylpropanoyl}-{(3S)-3-Amino-4-phenyl-butanoyl}-DArginyl-OH

FAB+ MS: (M+H)+=861.

EXAMPLE 111

(N-Methyl)Phenylalanyl-Lysyl-Prolyl-{(2R)-2-Amino-3-cyclohexylpropanoyl}-Phenylalanyl-Ψ(CH$_2$NH)-. DArginylNH(Benzyl)

The peptide is prepared in analogy to Example 1 stopping on Agenda A step 5 to yield N-Boc-(N-Methyl)Phenylalanyl-Lysyl(N-epsilon-Cbz)-Prolyl-{(2R)-2-Amino-3-cyclohexylpropanoyl}-Phenylalanyl-Ψ(CH$_2$NH)-DArginyl(N-guanidino-Tos)-Merrifield Resin. This is treated with methanol and triethylamine by the methods described in "Solid Phase Peptide Synthesis", 2nd edition, Stewart, J. M.; Young, J. D. Pierce Chemical Co.: Rockford, Ill., 1984: p 91. The methyl ester obtained is saponified using lithium hydroxide, followed by reaction with benzylamine by the standard coupling procedures. The obtained peptide is treated using the methods described in Example 2.

EXAMPLE 112

H-Phenylalanyl-Lysyl-Prolyl-{(N-Methyl)-(2R)-2-Amino-3-cyclohexylpropanoyl}-{(2S)-2-Amino-3-cyclohexylpropanoyl}-DArginyl-OH

FAB+ MS: (M+H)+=867.

EXAMPLE 113

H-Phenylalanyl-Lysyl-{2-[(2′S)pyrrolidinyl]acetyl}-{(2R)-2-Amino-3-cyclohexylpropanoyl}-phenylalanyl-DArginyl-OH

FAB+ MS: (M+H)+ =861.

EXAMPLE 114

H-Vinylgylcyl-Lysyl-Prolyl-Ψ{$CH_2$-NH}-{(2R)-2-Amino-3-cyclohexylpropanoyl}-{(2S)-2-Amino-3-cyclohexylpropanoyl}-DArginyl-OH

EXAMPLE 115

(N-Methyl)Phenylalanyl-Lysyl-{6-(Methylamino)hexanoyl}-Phenylalanyl-DArginyl-OH

Boc-6-aminohexanoic acid (5.00 g, 21.6 mmol) was dissolved in THF (120 mL). The solution was cooled to 0° C., and then 80% sodium hydride (1.94 g, 64.8 mmol) was introduced portionwise. After 1 h, iodomethane was added to the heterogeneous mixture, and the resultant mixture was permitted to warm gradually to ambient temperature overnight. After cooling to 0° C., the mixture was quenched with water (250 mL), extracted with hexane (2×100 mL) and acidified with 1M $KHSO_4$. The aqueous phase was extracted with ether (3×150 mL), and the combined organic extracts were dried over magnesium sulfate and concentrated under reduced pressure to furnish a colorless oil in quantitative yield. Boc-6-(N-Methyl)aminohexanoic acid was used to construct the peptide-resin as described in: Stewart, J. M.; Young, J. D. "Solid Phase Peptide Synthesis", 2nd edition; Pierce Chemical Co.: Rockford, Ill., 1984.

FAB+ MS: (M+H)+ =738 Amino Acid Anal.: MePhe (0.93), Phe (1.03), Lys (0.95), Arg (1.09).

EXAMPLE 116

(N-Methyl)Phenylalanyl-Lysyl-Sarcosyl-D{1-Naphthylalanyl}-{2-Naphthylalanyl}-DArginyl-OH

FAB+ MS: (M+H)+ =929.

EXAMPLE 117

H-Lysyl(N-epsilon-acetyl)-Lysyl-Prolyl-Ψ{$CH_2$-NH}-{(2R)-2-Amino-3-cyclohexylpropanoyl}-{(2S)-2-Amino-3-cyclohexylpropanoyl}-DArginyl-OH

EXAMPLE 118

(N-Methyl)Phenylalanyl-Lysyl-Prolyl-{(2R)-2-Amino-3-cyclohexylpropanoyl}-Phenylalanyl-{(3R)-3-Amino-7-guanidino-hexanoyl}-OH (3R)-3-Boc-amino-7-(guanidino-Tos)-hexanoic acid was prepared from Boc-DArginyl (guanidino-Tos)-OH by the method described in the literature; (Wakiyama, T.; Uratani, H.; Teshima, T.; Shiba, T. *Bull. Chem. Soc. Jpn.* 1975, 48, 2401. and Rodriguez, M.; Fulcrand, P.; Lauer, J.; Aumelas, A.; Martinez, J. *J. Med. Chem.*, 1989, 32, 522), and incorporated into the Merrifield resin as described in: Stewart, J. M.; Young, J. D. "Solid Phase Peptide Synthesis", 2nd edition; Pierce Chemical Co.: Rockford, Ill., 1984; p 71–72.

FAB+ MS: (M+H)+ =875.

EXAMPLE 119

(N-Methyl)Phenylalanyl-Lysyl-Sarcosyl-D{1-Naphthylalanyl}-{(2S)-2-Amino-3-cyclohexylpropanoyl}-DArginyl-OH

FAB+ MS: (M+H)+ =885.

EXAMPLE 120

H-Seryl-Lysyl-Prolyl-Ψ{$CH_2$-NH}-{(2R)-2-Amino-3-cyclohexylpropanoyl}-{(2S)-2-Amino-3-cyclohexylpropanoyl}-DArginyl-OH

EXAMPLE 121

(N-Methyl)Phenylalanyl-Lysyl-{4-(Methylamino)-butanoyl}-Phenylalanyl-DArginyl-OH This compound was prepared in analogy to Example 115.

FAB+ MS: (M+H)+ =710 Amino Acid Anal.: MePhe (0.97), Phe (1.03), Lys (0.95), Arg (1.03).

EXAMPLE 122

(N-Methyl)Phenylalanyl-Lysyl-{(N-Methyl)[(2R/S)-2-Benzyl-4-aminobutanoyl]}-Phenylalanyl-DArginyl-OH This compound was prepared in analogy to Example 131.

FAB+ MS: (M+H)+ =800 Amino Acid Anal.: MePhe (0.95 ), Phe (1.05), Lys (0.93), Arg (1.07).

EXAMPLE 123

H-Glutamyl-Lysyl-Prolyl-Ψ{$CH_2$-NH}-{(2R)-2-Amino-3-cyclohexylpropanoyl}-{(2S)-2-Amino-3-cyclohexylpropanoyl}-DArginyl-OH

EXAMPLE 124

{(N-[(3′R/S)-3′-Amino-3′-phenylpropyl])Lysyl-Prolyl-{(2R)-2-Amino-3-cyclohexylpropanoyl}-Phenylalanyl-DArginyl-OH FAB+ MS: (M+H)+ =847 Amino Acid Anal.: Phe (1.00), Lys (0.94), Cha (1.00), Arg (1.04), pro (1.02).

EXAMPLE 125

{(N-[(3′R/S)-3′-Amino-3′-phenylpropyl])Lysyl-Prolyl-{(2R)-2-Amino-3-cyclohexylpropanoyl}-Phenylalanyl-DArginyl-OH FAB+ MS: (M+H)+ =847 Amino Acid Anal.: Phe (1.00), Lys (0.97), Cha (0.99), Arg (1.02), Pro (1.01).

EXAMPLE 126

H-Glutaminyl-Lysyl-Prolyl-Ψ{$CH_2$-NH}-{(2R)-2-Amino-3-cyclohexylpropanoyl}-{(2S)-2-Amino-3-cyclohexylpropanoyl}-DArginyl-OH

EXAMPLE 127

{(N-[(3′R/S)-3′-Methylamino-3′-phenylpropyl])Lysyl-Prolyl-{(2R)-2-Amino-3-cyclohexylpropanoyl}-Phenylalanyl-DArginyl-OH FAB+ MS: (M+H)+ =861 Amino Acid Anal.: Phe (1.00), Lys (0.96), Cha (1.03), Arg (1.06), Pro (0.91).

EXAMPLE 128

{(N-[(3'R/S)-3'-Methylamino-3'-phenylpropyl])Lysyl-Prolyl{(2R)-2-Amino-3-cyclohexylpropanoyl}-Phenylalanyl-DArginyl-OH FAB+ MS: (M+H)+ =861 Amino Acid Anal.: Phe (1.00), Lys (0.97), Cha (0.99), Arg (1.03), Pro (1.10).

EXAMPLE 129

(N-Methyl)Phenyl-Lysyl-Prolyl-Ψ(CH$_2$—NH)-{(2R)-2-Amino-3-cyclohexylpropanoyl}-Phenylalanyl-DPhenylalanyl-OH

EXAMPLE 130

(N-Methyl)Phenylalanyl-Lysyl-{(N-Methyl)[(2R/S)-2-Benzyl-4-aminobutanoyl]}-Phenylalanyl-DArginyl-OH This compound was one of the diastereomers of Example 131.

FAB+ MS: (M+H)+ =800 Amino Acid Anal.: MePhe (0.92), Phe (1.05), Lys (0.98), Arg (1.05).

EXAMPLE 131

(N-Methyl)Phenylalanyl-Lysyl-{(N-Methyl)[(2R/S)-2-Benzyl-6-aminohexanoyl}-Phenylalanyl-DArginyl-OH Lithium diisopropylamide was prepared at 0° C. over 0.5 h from n-butyl lithium (2.45 mL, 6.12 mmol, 2.5M in hexanes) and diisopropylamine (0.86 mL, 6.12 mmol) in THF (25 mL). This solution was cooled to −78° C. followed by the introduction of Boc-(N-methyl)-aminohexanoic acid (0.50 g, 2.04 mmol) in a minimum of THF. After 0.5 h, benzyl bromide (0.73 mL, 6.12 mmol) was added followed by gradual warming to room temperature. The reaction mixture was quenched with saturated aqueous ammonium chloride, and the THF was removed under reduced pressure. The residue was taken into ethyl acetate which was washed with saturated aqueous ammonium chloride and brine. The organic phase was dried over magnesium sulfate and concentrated under reduced pressure. Chromatographic purification (silica gel, 5% MeOH/CHCl$_3$) provided Boc-(N-methyl)-2-benzyl-aminohexanoic acid (687 mg, 99%) as a colorless oil: $^1$H NMR (CDCl$_3$, 300 MHz) δ 7.32-7.15(m, 6 H), 3.16(br t, J=7 Hz, 2 H), 2.98 (dd, J=7 & 13 Hz, 1 H), 2.80 (s, 3 H), 2.80-2.60 (m, 2 H), 1.75-1.15 (series of m, 6 H), 1.43 (s, 9 H); MS (EI) m/e 336 (MH+), 280 (M-C$_4$H$_9$), 236 (M-Boc), 218. This was used to prepare the title compound using the methods described in: Stewart, J. M.; Young, J. D. "Solid Phase Peptide Synthesis", 2nd edition; Pierce Chemical Co.: Rockford, Ill., 1984;

FAB+ MS: (M+H)+ =828 Amino Acid Anal.: MePhe (0.85), Phe (0.98), Lys (0.98), Arg (1.04).

EXAMPLE 132

H-Glutamyl(gamma-NHNH$_2$)-Lysyl-Prolyl-Ψ{CH$_2$—NH}-{(2R)-2-Amino-3-cyclohexylpropanoyl}-{(2S)-2-Amino-3-cyclohexylpropanoyl}-DArginyl-OH

EXAMPLE 133

(N-Methyl)Phenylalanyl-Lysyl-Prolyl-{(2R)-2-Amino-3-cyclohexylpropanoyl}-Phenylalanyl-Ψ(CH$_2$NH)-DArginyl-NH$_2$ After the final amino acid is incorporated into the peptide-resin, the sequence is stopped on Agenda A at step 5 to yield N-Boc-(N-Methyl)Phenylalanyl-Lysyl(N-epsilon-Cbz)-Prolyl-{2R)-2-Amino-3-cyclohexylpropanoyl}-Phenylalanyl-Ψ(CH$_2$NH)-DArginyl (N-guanidino-Tos)-Merrifield resin. This is treated with ammonia using the methods described in "Solid Phase Peptide Synthesis", 2nd edition, Stewart, J. M.; Young, J. D. Pierce Chemical Co.: Rockford, Ill., 1984: p 91.

EXAMPLE 134

(N-Methyl)Phenylalanyl-Lysyl-{(N-Methyl)[(2R/S)-2-Benzyl-6-aminohexanoyl}-Phenylalanyl-DArginyl-OH This compound was isolated as one of the diastereomers of Example 131.

FAB+ MS: (M+H)+ =828 Amino Acid Anal.: MePhe (0.93), Phe (1.00), Lys (0.98), Arg (1.03).

EXAMPLE 135

H-Citrullyl-Lysyl-Prolyl-Ψ{CH$_2$-NH}-{(2R)-2-Amino-3-cyclohexylpropanoyl}-{(2S)-2-Amino-3-cyclohexylpropanoyl}-DArginyl-OH

EXAMPLE 136

(N-Methyl)Phenylalanyl-Lysyl-{(N-Methyl)[(2R/S)-2-Cyclohexylmethyl-6-aminohexanoyl]}-Phenylalanyl-DArginyl-OH This compound was prepared in analogy to Example 131.

FAB+ MS: (M+H)+ =834 Amino Acid Anal.: MePhe (0.89), Phe (0.97), Lys (1.00), Arg (1.04).

EXAMPLE 137

(N-Methyl)Phenylalanyl-Lysyl-{(N-Methyl)[(2R/S)-2-Cyclohexylmethyl-6-aminohexanoyl]}-phenylalanyl-DArginyl-OH This compound was one of the diastereomers of Example 136.

FAB+ MS: (M+H)+ =834 Amino Acid Anal.: MePhe (0.93), Phe (0.99), Lys (0.99), Arg (1.02).

EXAMPLE 138

H-(S-Benzyl)Cysteinyl-Lysyl-Prolyl-Ψ{CH$_2$-NH}-{(2R)-2-Amino-3-cyclohexylpropanoyl}-{(2S)-2-Amino-3-cyclohexylpropanoyl}-DArginyl-OH

EXAMPLE 139

(N-Methyl)Phenylalanyl-Lysyl-Prolyl-{(2R)-2-Amino-3-cyclohexylpropanoyl}-Phenylalanyl-Ψ{(R/S)CH(CH$_3$)NH}-DArginyl-OH Commercially available Boc-Phenylalanine was reacted with methyl lithium to yield 3-{N-Boc-amino}-4-phenylbutane-2-one as described in the literature: Kawai, M.; Boparai, A. S.; Bernatowicz, M. S.; Rich, D. H. J. Org. Chem. 1983, 48, 1876.

Reductive amination of 3-{N-Boc-amino}-4-phenylbutane-2-one reacted with D-Arginine(guanidino-Tos) benzyl ester using NaCNBH$_3$ in 1% acetic acid-methanol gave Boc-Phenylalanyl-Ψ{(RS)CH(CH$_3$)NH}-DArginyl(guanidino-Tos)-OBenzyl that was a mixture of diastereomers which were separable by silica gel column chromatography. Rf(7% ethanol in ethyl acetate)=0.61 and 0.57. One of the diastereomers of Boc-Phenylalanyl-Ψ{(R/S)CH(CH$_3$)NH}-DArginyl(Tos)-OBenzyl was treated with 4N hydrochloric acid in dioxane, and coupled with N-Boc-(N-Methyl)Phenylalanyl-Lysyl(N-epsilon-Boc)-prolyl-{(2R)-2-Amino-3-cyclohexylpropanoic acid (Example 51) by the standard methods previously described. The peptide obtained was treated with hydrogen fluoride (HF) and purified using the methods described in Example 2.
FAB+ MS: (M+H)+ =861.

EXAMPLE 140

(N-Methyl)Phenylalanyl-Lysyl-Prolyl-{(2R)-2-Amino-3-cyclohexylpropanoyl}-Phenylalanyl-Ψ{(R/S)CH(CH₃)NH}-Arginyl-OH This compound was prepared in analogy to Example 139.
FAB+ MS: (M+H)+ =861.

EXAMPLE 141

H-Methionyl-Lysyl-Prolyl-Ψ{CH₂-NH}-{(2R)-2-Amino-3-cyclohexylpropanoyl}-{(2S)-2-Amino-3-cyclohexylpropanoyl}-DArginyl-OH

EXAMPLE 142

(N-Methyl)Phenylalanyl-Lysyl-Prolyl-{(2R)-2-Amino-3-cyclohexylpropanoyl}-Phenylalanyl-Ψ{(R/S)CH(CH₃)NH}-DArginyl-OH This compound was prepared as described in Example 139 and represents the other diastereomer.
FAB+ MS: (M+H)+ =861.

EXAMPLE 143

(N-Methyl)Phenylalanyl-Lysyl-Prolyl-{(2R)-2-Amino-3-cyclohexylpropanoyl}-Phenylalanyl-Ψ{(R/S)CH(CH₃)NH}-Arginyl-OH This compound was prepared in analogy to Example 139.
FAB+ MS: (M+H)+ =861.

EXAMPLE 144

H-(S-Aminomethyl)Cysteinyl-Lysyl-Prolyl-Ψ{CH₂-NH}-{(2R)-2-Amino-3-cyclohexylpropanoyl}-{(2S)-2-Amino-3-cyclohexylpropanoyl}-DArginyl-OH

EXAMPLE 145

(N-Methyl)Phenylalanyl-Lysyl-Prolyl-D{1-Naphthylalanyl}-Phenylalanyl-{(3R)-3-amino-7-guanidinohexanoyl}-OH This compound was prepared in analogy to Example 118.
FAB+ MS: (M+H)+ =919.

EXAMPLE 146

(N-Methyl)Phenylalanyl-Lysyl-Prolyl-D{1-Naphthylalanyl}-{1Naphthylalanyl}-{(3R)-3-amino-7-guanidinohexanoyl}-OMe This compound was prepared in analogy to Example 139, except that (3R)-3-N-Boc-amino-7-(guanidino-Tos)hexanoic acid methyl ester and Boc-D and L-1-Naphthylalanyl-OH were used to obtain the fully protected analogue: N-Boc-(N-Methyl)Phenylalanyl-Lysyl(N-epsilon-Cbz)-Prolyl-D{1-Naphthylalanyl}-{1-Naphthylalanyl}-{(3R)-3-amino-7-(guanidino-Tos)hexanoic acid methyl ester. This was treated with HF using the procedures described in Example 2 to yield the title compound.
FAB+ MS: (M+H)+ =983.

EXAMPLE 147

H-{(2R)-2-amino-3-chloropropanoyl)-Lysyl-prolyl-Ψ{CH₂NH}-{(2R)-2-Amino-3-cyclohexylpropanoyl}-{(2S)-2-Amino-3-cyclohexylpropanoyl}-DArginyl-OH

EXAMPLE 148

(N-Methyl)Phenylalanyl-Lysyl-Prolyl-{(2R)-2-Amino-3-cyclohexylpropanoyl}-{1-Naphthylalanyl}-{(3R)-3-amino-7-guanidinohexanoyl}-OH This compound was prepared in analogy to Example 118
FAB+ MS: (M+H)+ =925.

EXAMPLE 149

(N-Methyl)Phenylalanyl-Lysyl-Prolyl-D{1-Naphthylalanyl}-{1-Naphthylalanyl}-{(3R)-3-amino-7-guanidinohexanoyl}-OMe This compound was prepared in analogy to Example 146
FAB+ MS: (M+H)+ =939.

EXAMPLE 150

(N-Methyl)Phenylalanyl-Lysyl-Sarcosyl-D{1-Naphthylalanyl}D{2-Naphthylalanyl}-DArginyl-OH

FAB+ MS: (M+H)+ =929.

EXAMPLE 151

{2-Acetamido-3-phenylacryloyl}-Lysyl-Prolyl-Ψ{CH₂-NH}-{(2R)-2-Amino-3-cyclohexylpropanoyl}-{(2S)-2-Amino-3-cyclohexylpropanoyl}-DArginyl-OH

EXAMPLE 152

(N-Methyl)Phenylalanyl-Lysyl-Prolyl-D{1-Naphthylalanyl}-{1-Naphthylalanyl}-{(3R)-3-amino-7-guanidinohexanoyl-OH This compound was prepared in analogy to Example 118
FAB+ MS: (M+H)+ =969.

EXAMPLE 153

(N-Methyl)Phenylalanyl-Lysyl-(N-Methyl)Phenylalanyl-{(2R)-2-Amino-3-cyclohexylpropanoyl}-Phenylalanyl-DArginyl-OH FAB+ MS: (M+H) +=925 Amino Acid Anal.: MePhe (2.01), Phe (1.00), Cha (1.01), Lys (0.89), Arg (1.12).

EXAMPLE 154

(N-Methyl)Phenylglycyl-Lysyl-Prolyl-Ψ{CH₂-NH}-{(2R)-2-Amino-3-cyclohexylpropanoyl}-{(2S)-2-Amino-3-cyclohexylpropanoyl}-DArginyl-OH

EXAMPLE 155

(N-Methyl)Phenylalanyl-Lysyl-{(2R/S)-2-Methylamino-5-phenylpentanoyl}-{(2R)-2-Amino-3-cyclohexylpropanoyl}-Phenylalanyl-DArginyl-OH FAB+ MS: (M+H)+ =953 Amino Acid Anal.: MePhe (1.06), Phe (0.78), Cha (0.99), Lys (1.00), Arg (1.16).

EXAMPLE 156

(N-Methyl)Phenylalanyl-Lysyl-{(2R/S)-2-Methylamino-5-phenylpentanoyl}-{(2R)-2-Amino-3-cyclohexylpropanoyl}-Phenylalanyl-DArginyl-OH FAB+ MS: (M+H)+=953 Amino Acid Anal.: MePhe (1.02 ), Phe (0.94), Cha (0.96), Lys (0.92), Arg (1.15).

EXAMPLE 157

(N-Methyl)Phenylalanyl-Lysyl-Sarcosyl-D{1-Naphthylalanyl}-{2-Naphthylalanyl}-DArginyl-OH

FAB+ MS: (M+H)+=929.

EXAMPLE 158

(N-Methyl)Phenylalanyl-Lysyl-Prolyl-{(3R)-3-Amino-4-cyclohexylbutanoyl}-Phenylalanyl-DArginyl-OH

FAB+ MS: (M+H)+=875.

EXAMPLE 159

(N-Methyl)Phenylalanyl-Lysyl-Prolyl-Ψ{CH$_2$-NH}-{(2R)-2-Amino-3-cyclohexylpropanoyl}-Azaphenylalanyl-DArginyl-OH.

EXAMPLE 160

(N-Methyl)Phenylalanyl-Lysyl-Prolyl-{(3S)-3-Amino-4-cyclohexylbutanoyl}-Phenylalanyl-DArginyl-OH

FAB+ MS: (M+H)+=875.

EXAMPLE 161

(N-Methyl)Phenylalanyl-Lysyl-Prolyl-{3-amino-2,2-dibenzylpropanoyl}-DArginyl-OH

FAB+ MS: (M+H)+=812.

EXAMPLE 162

(N-Methyl)Phenylalanyl-Lysyl-Azaglycyl-Ψ{CH$_2$-NH}-{(2R)-2-Amino-3-cyclohexylpropanoyl}-{(2S)-2-Amino-3-cyclohexylpropanoyl}-DArginyl-OH

EXAMPLE 163

(N-Methyl)Phenylalanyl-Lysyl-Prolyl-{(2R)-2-Amino-3-cyclohexylpropanoyl}-{3-amino-2,2-dibenzylpropanoyl}-DArginyl-OH

FAB+ MS: (M+H)+=965.

EXAMPLE 164

(N-Methyl)Phenylalanyl-Lysyl-Prolyl-{(2R)-2-Amino-3-cyclohexylpropanoyl}-{(2R/S)-3-Amino-2-benzylpropanoyl}-DArginyl-OH

FAB+ MS: (M+H)+=875.

EXAMPLE 165

(N-Methyl)Phenylalanyl-Lysyl-Prolyl-{(2R)-2-Amino-3-cyclohexylpropanoyl}-{(2R/S)-3-Amino-2-benzylpropanoyl}-DArginyl-OH

FAB+ MS: (M+H)+=875.

EXAMPLE 166

{6-Aminohexanoyl}-Prolyl-{(2R)-2-(4'-phenylbutylamino)-3-cyclohexylpropanoyl}-{(2S)-2-Amino-3-cyclohexylpropanoyl}-DArginyl-OH

FAB+ MS: (M+H)+=823.

EXAMPLE 167

(N-Methyl)Phenylalanyl-Lysyl-Prolyl-{(2R)-2-Amino-3-cyclohexylpropanoyl}-DPhenylalanyl-Ψ{(R/S)CH(CH$_3$)NH}-Arginyl-OH This compound was prepared in analogy to Example 139.

FAB+ MS: (M+H)+=861.

EXAMPLE 168

(N-Methyl)Phenylalanyl-Lysyl-Prolyl-{(2R/S)-2-Benzyl-3-aminopropanoyl}-Phenylalanyl-DArginyl-OH

FAB+ MS: (M+H)+=869.

EXAMPLE 169

(N-Methyl)Phenylalanyl-Ψ{CH$_2$NH}-Lysyl-Prolyl-{(2R)-2-Amino-3-cyclohexylpropanoyl}-Phenylalanyl-DArginyl-OH

FAB+ MS: (M+H)+=847.

EXAMPLE 170

(N-Methyl)Phenylalanyl-Lysyl-Prolyl-{(2R)-2-Amino-3-cyclohexylpropanoyl}-Phenylalanyl-{(3R)-Amino-4-phenylbutanoic acid}

Commercially available 2-{N-Boc-amino}-3-phenyl-n-propanol (2.0 g, 8 mmole) was mesylated using methanesulfonyl chloride and triethylamine in methylene chloride and reacted with potassium cyanide in N,N-dimethylsulfoxide (DMSO) to obtain (3R)-N-Boc-amino-4-phenyl-butyronitrile in 81% yield. This was hydrolyzed to give (3R)-amino-4-phenyl-butanoic acid hydrochloride in 62% yield (FAB+ MS: (M+H)+=180). N-Boc-(N-Methyl)Phenylalanyl-Lysyl(N-epsilon-Boc)-Prolyl-{(2R)-2-Amino-3-cyclohexylpropanoyl-Phenylalanine (Example 101) was reacted with (3R)-amino-4-phenyl-butanoic acid hydrochloride in N,N-dimethylformamide (DMF) via mixed anhydride formation [isobutylchloroformate (IBCF) and N-methylmorpholine (NMM)]. The peptide obtained was treated with 50%-trifluoroacetic acid (TFA) in methylene chloride or 4N-hydrochloric acid in dioxane and purified by RP-HPLC by the methods described in Example 2.

FAB+ MS: (M+H)+=866.

EXAMPLE 171

(N-Methyl)Phenylalanyl-Lysyl-Prolyl-{(2R)-2-Amino-3-cyclohexylpropanoyl}-Phenylalanyl-D-(N-Methyl)-Phenylalanyl-OH N-Boc-(N-Methyl)Phenylalanyl-Lysyl(N-epsilon-Boc)-Prolyl-{(2R)-2-Amino-3-cyclohexylpropanoyl}-Phenylalanine (Example 101) was reacted with (N-Methyl)-D-Phenylalanine in N,N-dimethylformamide (DMF) via mixed anhydride formation [isobutylchloroformate (IBCF) and N-methylmorpholine (NMM)]. The peptide obtained was treated with 50%-trifluoroacetic acid (TFA) in methylene chloride or 4N-hydrochloric acid in dioxane and purified by RP-HPLC by the methods described in Example 2.

FAB+ MS: (M+H)+=866.

EXAMPLE 172

(N-Methyl)Phenylalanyl-Lysyl-Ψ{[R/S]CH(OH)}-Glycyl-{(2R)-2-Amino-3-cyclohexylpropanoyl}-{(2S)-2-Amino-3-cyclohexylpropanoyl}-DArginyl-OH (3RS)-Hydroxy-(4S)-N-Boc-amino-8-N-benzyloxycarbonylamino-octanoic acid was prepared using the method described in the literature: Salituro, F. G.; Agarwal, N.; Hofmann, T.; Rich, D. H. *J. Med. Chem.* 1987, 30, 286. This was incorporated into the peptide by the procedures described in Example 1 and treated using the techniques described in Example 2. The diastereomers were separated on RP-HPLC.

FAB+ MS: (M+H)+ =814.

EXAMPLE 173

(N-Methyl)Phenylalanyl-Lysyl-Ψ{[R/S]CH(OH)}-Glycyl-{(2R)-2-Amino-3-cyclohexylpropanoyl}-{(2S)-2-Amino-3-cyclohexylpropanoyl}-DArginyl-OH This compound was prepared as described in Example 172 and represents the other diastereomer.

FAB+ MS: (M+H)+ =814.

EXAMPLE 174

(N-Methyl)Phenylalanyl-Lysyl-Prolyl-{(2R)-2-Amino-3-cyclohexylpropanoyl}-Phenylalanyl-Ψ{C(=O)O}-(S)Phenylalanyl-OH N-Boc-(N-Methyl)Phenylalanyl-Lysyl (N-epsilon-Boc)-Prolyl-{(2R)-2-Amino-3-cyclohexylpropanoyl}-Phenylalanine (Example 101) (135.8 mg, 0.15 mmole) was dissolved in 3 mL of methylene chloride at −20° C., and triethylamine (TEA) (25 μL, 0.18 mmole) and isobutyl chloroformate (IBCF) (25 μL, 0.18 mole) were added. This was followed by the addition of L-3-phenyllactic acid (49.9 mg, 0.3 mmole) in 1 mL of DMF containing triethylamine (41.8 μL, 0.3 mmole), and the reaction was stirred at −20° C. for 1 hr and at room temperature for one over night. The solvent was removed and the residue dissolved in ethyl acetate which was washed with brine, 10%-potassium hydrogen sulfate, brine, and dried over magnesium sulfate. The solvent was removed and the residue was treated with 4N hydrochloric acid in dioxane to yield crude product, HPLC purification of which gave 21.2 mg of pure title compound.

FAB+ MS: (M+H)+ =853.

EXAMPLE 175

(N-Methyl)Phenylalanyl-Lysyl-Prolyl-{(2R)-2-Amino-3-cyclohexylpropanoyl}-Phenylalanyl-Ψ{C(=O)OCH$_2$}-(S)Phenylglycyl-OH The title compound was prepared using the procedure described for Example 174, except (S)-Tropic acid was used instead of phenyllactic acid.

FAB+ MS: (M+H)+ =853.

EXAMPLE 176

H-Phenylalanyl-Lysyl-{3-(R/S)-Aminomethylcyclohexylcarbonyl}-{(2S)-2-Amino-3-cyclohexylpropanoyl}-DArginyl-OH N-Boc-(3RS)-Aminomethylcyclohexanecarboxylic acid was prepared from commercially available 3-cyanobenzoic acid by catalytic hydrogenation using palladium on charcoal in methanol to give the 3-aminomethylbenzoic acid. This was reacted with Boc-ON, followed by hydrogenation with rhodium on aluminum oxide in methanol to yield N-Boc-(3RS)-aminomethylcyclohexane carboxylic acid. FAB+ MS: (M+H)+ =258 This compound was then incorporated into the peptide using the methods described in Example 1 and isolated by the method described in Example 2. The diastereomers were separated by RP-HPLC.

FAB+ MS: (M+H)+ =742.

EXAMPLE 177

H-Phenylalanyl-Lysyl-{3-(R/S)Aminomethylcyclohexylcarbonyl}-{(2S)-2-Amino-3-cyclohexylpropanoyl}-DArginyl-OH This compound was prepared as described in Example 176 and represents the other diastereomer.

FAB+ MS: (M+H)+ =742.

EXAMPLE 178

H-Phenylalanyl-Lysyl-{Fragment-7}-{(2S)-2-Amino-3-cyclohexylpropanoyl}-DArginyl-OH Fragment-7 was prepared as described in the literature: Hinds, M. G.; Richards, N. G. J.; Robinson, J. A. *J. Chem. Soc Chem. Commun.*, 1988, 1147 and incorporated into the peptide by classical solution methods as described in "Peptide Synthesis", Second Edition, M. Bodanszky, Y. S. Klausner, and M. A. Ondetti (1976). FAB+ MS: (M+H)+ =879; Calcd for $C_{46}H_{74}N_{10}O_7 \cdot 3.75$ CF$_3$COOH: C,49.17; H, 6.00; N,10.72%. Found; C,49.20; H,6.16, N, 11.08%

The foregoing examples are merely illustrative of the invention and are not intended to limit the invention to the disclosed compounds. Variations and changes which are obvious to one skilled in the art are intended to be within the scope and nature of the invention which is defined in the appended claims.

We claim:

1. An anaphylotoxin activity modulating compound of the formula:

A-B-D-E-G-J-L-M-Q or a pharmaceutically acceptable salt thereof wherein the groups A through Q have the values:

A is $R_1$-$R_2$-$R_3$;
B is selected from the group consisting of $R_4$-$R_5$-$R_6$, $R_{31}$, $R_{32}$, $R_{35}$ and $R_{37}$;
D is selected from the group consisting of $R_7$-$R_8$-$R_9$, $R_{31}$, $R_{32}$, $R_{35}$ and $R_{37}$;
E is selected from the group consisting of $R_{10}$-$R_{11}$-$R_{12}$, $R_{31}$, $R_{32}$, $R_{35}$ and $R_{37}$;
G is selected from the group consisting of $R_{13}$-$R_{14}$-$R_{15}$, $R_{31}$, $R_{32}$, $R_{35}$ and $R_{37}$;
J is selected from the group consisting of $R_{16}$-$R_{17}$-$R_{18}$, $R_{31}$, $R_{32}$, $R_{35}$ and $R_{37}$;
L is selected from the group consisting of $R_{19}$-$R_{20}$-$R_{21}$, $R_{31}$, $R_{32}$, $R_{35}$ and $R_{37}$;
M is a valence bond, or is selected from the group consisting of $R_{22}$-$R_{23}$-$R_{24}$, $R_{31}$, $R_{32}$, $R_{35}$, and $R_{37}$;
Q is $R_{25}$-$R_{26}$-$R_{27}$; or B and D, taken together, optionally represent a group selected from the group consisting of $R_{33}$, $R_{34}$, $R_{38}$, $R_{39}$, $R_{40}$, $R_{41}$, $R_{42}$, $R_{43}$, and $R_{44}$;
D and E, taken together, optionally represent a group selected from the group consisting of $R_{33}$, $R_{34}$, $R_{38}$, $R_{39}$, $R_{40}$, $R_{41}$, $R_{42}$, $R_{43}$, and $R_{44}$;
E and G, taken together, optionally represent a group selected from the group consisting of $R_{33}$, $R_{34}$, $R_{38}$, $R_{39}$, $R_{40}$, $R_{41}$, $R_{42}$, $R_{43}$, and $R_{44}$;
G and J, taken together, optionally represent a group selected from the group consisting of $R_{33}$, $R_{34}$, $R_{38}$, $R_{39}$, $R_{40}$, $R_{41}$, $R_{42}$, $R_{43}$, and $R_{44}$;
J and L, taken together, optionally represent a group selected from the group consisting of $R_{33}$, $R_{34}$, $R_{38}$, $R_{39}$, $R_{40}$, $R_{41}$, $R_{42}$, $R_{43}$, and $R_{44}$;
L and M, taken together, optionally represent a group selected from the group consisting of $R_{33}$, $R_{34}$, $R_{38}$, $R_{39}$, $R_{40}$, $R_{41}$, $R_{42}$, $R_{43}$, and $R_{44}$; and one or more of the groups $R_5$-$R_6$-$R_7$, $R_8$-$R_9$-$R_{10}$, $R_{11}$-$R_{12}$-$R_{13}$, $R_{14}$-$R_{15}$-$R_{16}$, $R_{17}$-$R_{18}$-$R_{19}$, $R_{20}$-$R_{21}$-$R_{22}$, and $R_{23}$-$R_{24}$-$R_{25}$, independently may optionally represent $R_{36}$;

wherein (a) $R_1$ is selected from the group consisting of lower alkyl, aryl, arylalkyl, and hydrogen;

(b) $R_2$ is selected from the group consisting of $>CR_{99}R_{100}$ and oxygen, with the proviso that when $R_2$ is oxygen, $R_1$ is aryl, lower alkyl, or arylalkyl;

(c) $R_3$ is selected from the group consisting of $>C=O$ and $>CH_2$, with the proviso that when $R_3$ is $>CH_2$ then $R_2$ cannot be oxygen;

(d) $R_4$ is $>NR_{101}$ where $R_{101}$ is selected from the group consisting of hydrogen, lower alkyl, arylalkyl, and alkenyl;

(e) $R_5$ is selected from the group consisting of $>CR_{201}R_{202}$, $>NR_{203}$, $>C=CR_{205}R_{206}$, existing in either the Z- or E-configuration, and substituted cyclopropyl of the formula

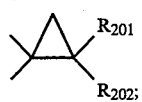

(f) $R_6$, $R_9$, $R_{12}$, $R_{15}$, and $R_{18}$ are independently selected from the group consisting of $>C=O$, $>CH_2$, $-CH_2C(O)-$, $-NHC(O)-$, $>C=S$, $>SO_2$, and $>P(O)X$ where X is selected from hydroxy, alkoxy, amino, alkylamino and dialkylamino;

(g) $R_7$, $R_{10}$, $R_{13}$, $R_{16}$, $R_{19}$, and $R_{22}$, are independently selected from the group consisting of $>CH_2$ and $>NR_{50}$ where $R_{50}$ is selected from the group consisting of hydrogen, lower alkyl, arylalkyl, aryl, hydroxy and alkoxy;

(h) $R_{21}$, and $R_{24}$ are independently selected from the group consisting of $>C=O$, $-CH_2C(O)-$, $-NHC(O)-$, $>C=S$, $>SO_2$, and $>P(O)X$ where X is selected from the group consisting of hydroxy, alkoxy, amino, alkylamino and dialkylamino, with the proviso that when $R_{22}$-$R_{23}$-$R_{24}$ is present, $R_{21}$ is $>CH_2$ (i) $R_8$ is selected from the group consisting of $>CR_{210}R_{211}$, $>NR_{213}$, $>C=CR_{215}R_{216}$, existing in either the Z- or E-configuration, and substituted cyclopropyl of the formula

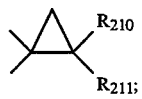

(j) $R_{11}$ is selected from the group consisting of $>CR_{220}R_{221}$, $>NR_{223}$, $>C=CR_{225}R_{226}$, existing in either the Z- or E-configuration, and substituted cyclopropyl of the formula

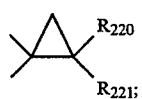

(k) $R_{14}$ is selected from the group consisting of $>CR_{230}R_{231}$, $>NR_{233}$, $>C=CR_{235}R_{236}$, existing in either the Z- or E-configuration, and substituted cyclopropyl of the formula

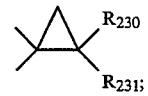

(l) $R_{17}$ is selected from the group consisting of $>CR_{301}R_{302}$, $>NR_{303}$, $>C=CR_{305}R_{306}$, existing in either the Z- or E-configuration, and substituted cyclopropyl of the formula

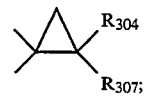

(m) $R_{20}$ is selected from the group consisting of $>CR_{310}R_{311}$, $>C=CR_{315}R_{316}$, existing in either the Z- or E-configuration, and substituted cyclopropyl of the formula

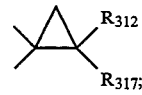

(n) $R_{23}$ is selected from the group consisting of $>CR_{320}R_{321}$, $>C=CR_{325}R_{326}$, existing in either the Z- or E-configuration, and substituted cyclopropyl of the formula

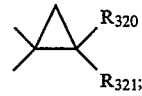

(o) $R_{25}$ is selected from the group consisting of $>O$, and $>NR_{109}$ where $R_{109}$ is selected from the group consisting of hydrogen, lower alkyl, and arylalkyl;

(p) $R_{26}$ is selected from the group consisting of hydrogen, lower alkyl, arylalkyl and $>NR_{110}$ where $R_{110}$ is selected from the group consisting of hydrogen, lower alkyl, or arylalkyl with the provisos that
 (i) when $R_{25}$ is $>O$ then $R_{26}$ is lower alkyl, and
 (ii) when $R_{26}$ is hydrogen, lower alkyl, or arylalkyl, then $R_{27}$ is absent;

(q) $R_{27}$ is selected from the group consisting of hydrogen, and aryl;

(r) $R_{31}$ is

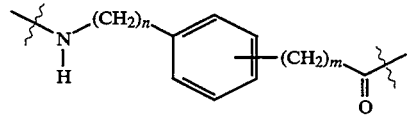

where m and n are integers independently selected from 0, 1 and 2;

(s) $R_{32}$ is

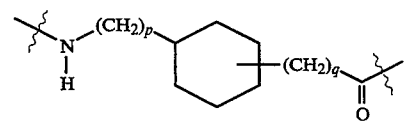

where p and q are integers independently selected from 0, 1 and 2;

(t) $R_{33}$ is

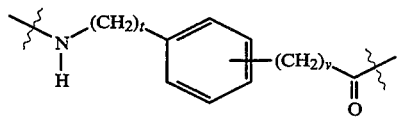

where t and v are integers independently selected from 0, 1, 2 and 3;

(u) $R_{34}$ is

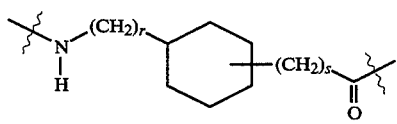

where r and s are integers independently selected from 0, 1, 2 and 3;

(v) $R_{35}$ is

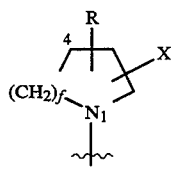

where f is an integer of 0 to 2, X is selected from the group consisting of >C=O and —CH$_2$— and R is selected from the group consisting of hydrogen and lower alkyl, with the provisos that
(i) when f is 0, X is at C-2 and R is at C-3 or C-4;
(ii) when f is 1, X is at C-2 and R is at C-3, C-4 or C-5 and C-3,4 are saturated or unsaturated;
(iii) when f is 2, X is at C-2, C-3 or C-4 and R is at C-2, C-3, C-4, C-5 or C-6 when the position is unoccupied by X and C-3,4 or C-4,5 are saturated or unsaturated; and (w) $R_{36}$ is

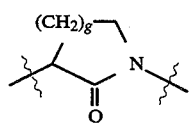

where g is an integer of from 0 to 3;

(x) $R_{37}$ is

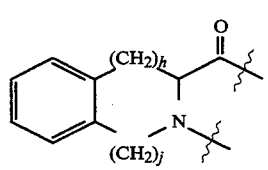

wherein h is 1 and j is 0 or 1;

(y) $R_{38}$ is

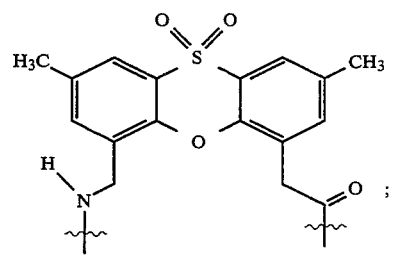

(z) $R_{39}$ is

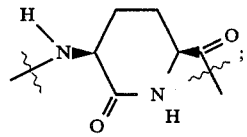

(aa) $R_{40}$ is

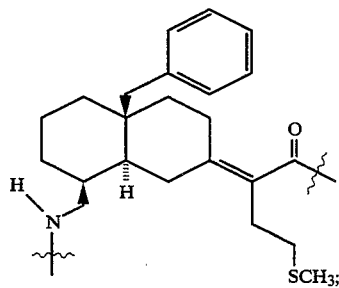

(ab) $R_{41}$ is

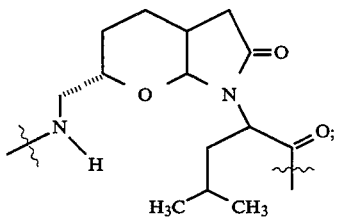

(ac) $R_{42}$ is

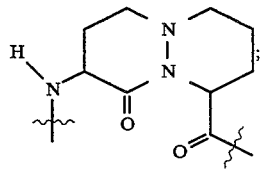

(ad) $R_{43}$ is

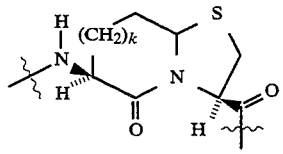

where k is an integer of from zero to two;

(ae) $R_{44}$ is

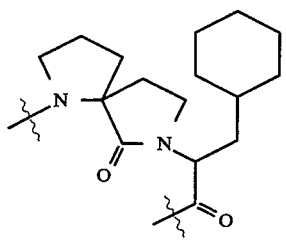

(af) R₁ and R₂, taken together, optionally represent a group selected from the group consisting of aryl, and hydrogen;

(ag) R₁, R₂ and R₃, taken together, optionally represent a group selected from the group consisting of lower alkyl, arylalkyl, alkenyl, hydrogen, and an N-terminal protecting group;

(ah) R₆ and R₇; R₉ and R₁₀; R₁₂ and R₁₃; R₁₅ and R₁₆; R₁₈ and R₁₉; R₂₁ and R₂₂; each pair taken together, optionally and independently represent a group selected from the group consisting of —C(O)NH—, >CH₂, —(CH₂)₃—, —CH=CH—, —CH(OH)—, —C≡C—, —C(=CH₂)CH₂—, —CH(OH)CH₂—, —C(O)O—, —C(O)S—, —CH₂C(O)O—, —CH₂C(O)S—, —CH₂O—, ≠ CH₂S—, and —NHC(O)—, with the provisos that
(i) at least one of said pair, taken together, must be other than —C(O)NH—; and
(ii) when R₅ is >NR₂₀₃ or >C=CR₂₀₅R₂₀₆, R₆ and R₇, taken together, represent —C(O)NH— or —C(O)NCH₃;
(iii) when R₈ is >NR₂₁₃ or >C=CR₂₁₅R₂₁₆, R₉ and R₁₀, taken together, represent —C(O)NH— or —C(O)NCH₃—;
(iv) when R₁₁ is >NR₂₂₃ or >C=CR₂₂₅R₂₂₆, R₁₂ and R₁₃, taken together represent —C(O)NH— or —C(O)NCH₃—;
(v) when R₁₄ is >NR₂₃₃ or >C=CR₂₃₅R₂₃₆, R₁₅ and R₁₆, taken together, represent —C(O)NH— or —C(O)NCH₃—;
(vi) when R₁₇ is >NR₃₀₃ or >C=CR₃₀₅R₃₀₆, R₁₈ and R₁₉, taken together, represent —C(O)NH— or —C(O)NCH₃—;
(vii) when R₂₀ is >C=CR₃₁₅R₃₁₆, R₂₁ and R₂₂, taken together, represent —C(O)NH— or —C(O)NCH₃—;

(ai) R₂₆ and R₂₇, taken together, optionally represent hydrogen, with the proviso that when R₂₅ is >O then R₂₆ and R₂₇, taken together, represent hydrogen, lower alkyl, or arylalkyl;

(aj) R₉₉, R₂₀₂, R₂₁₁, R₂₂₁, R₂₃₁, R₃₀₂, R₃₁₁, and R₃₂₁ are independently selected from the group consisting of hydrogen, arylalkyl with the proviso that for R₃₀₂ and R₃₁₁, arylalkyl is limited to benzyl when R₁₉-R₂₀-R₂₁ or R₂₂-R₂₃-R₂₄ respectively represent an L-arginyl residue, and lower alkyl;

(ak) R₁₀₀ is selected from the group consisting of hydrogen, and lower alkyl;

(al) R₂₀₁ is selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, and sulfhydrylalkyl;

(am) R₂₀₁ and R₂₀₂, R₂₁₀ and R₂₁₁, R₂₂₀ and R₂₂₁, R₂₃₀ and R₂₃₁, R₃₀₁ and R₃₀₂, R₃₁₀ and R₃₁₁, R₃₂₀ and R₃₂₁, each pair taken together, independently may optionally represent —(CH₂)ᵤ— where z is an integer of from 2 to 6;

(an) R₂₀₃ is selected from the group consisting of hydrogen, lower alkyl, alkenyl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, and sulfhydrylalkyl with the proviso that R₂₀₃ may not be a vinyl group nor have a heteroatom directly attached to the nitrogen or separated from it by one methylene unit;

(ao) R₂₀₅, R₂₀₆, R₂₁₅, R₂₁₆, R₂₂₅, R₂₂₆, R₂₃₅, R₂₃₆, R₃₀₅, and R₃₀₆ are independently selected from the group consisting of hydrogen, lower alkyl, aryl, arylalkyl, wherein arylalkyl is excluded from R₃₀₅ and R₃₀₆ when R₁₉-R₂₀-R₂₁ represents an L-arginyl residue, (cycloalkyl)alkyl, amidoalkyl, wherein benzoyl amides and their heterocyclic variants are excluded from R₃₀₅ and R₃₀₆ when R₁₉-R₂₀-R₂₁ represents an L-arginyl residue (carboxyamido)alkyl, wherein aniline amides and their heterocyclic variants are excluded from R₃₀₅ and R₃₀₆ when R₁₉-R₂₀-R₂₁ represents an L-arginyl residue; ureidoalkyl, and (heterocyclic)alkyl, wherein when R₁₉-R₂₀-R₂₁ represents an L-arginyl residue, then the heterocycle at from R₃₀₅ and R₃₀₆ can only be separated by one methylene unit from the alpha-carbon;

(ap) R₂₁₀ selected from the group consisting of lower alkyl, arylalkyl, aminoalkyl, and guanidinoalkyl;

(aq) R₂₁₃ is selected from the group consisting of lower alkyl, arylalkyl, aminoalkyl, and guanidinoalkyl with the proviso that R₂₁₃ may not be a vinyl group nor have a heteroatom directly attached to the nitrogen or separated from it by one methylene unit;

(ar) R₂₂₀ is selected from the group consisting of hydrogen, lower alkyl, arylalkyl, (cycloalkyl)alkyl, and guanidinoalkyl;

(as) R₂₂₃ is selected from the group consisting of hydrogen, lower alkyl, arylalkyl, (cycloalkyl)alkyl, and guanidinoalkyl, with the proviso that R₂₂₃ may not be a vinyl group nor have a heteroatom directly attached to the nitrogen or separated from it by one methylene unit;

(at) R₂₃₀ is selected from the group consisting of hydrogen, lower alkyl, arylalkyl, and (cycloalkyl)alkyl;

(au) R₂₃₃ is selected from the group consisting of hydrogen, lower alkyl, arylalkyl, and (cycloalkyl)alkyl with the proviso that R₂₃₃ may not be a vinyl group nor have a heteroatom directly attached to the nitrogen or separated from it by one methylene unit;

(av) R₃₀₁ is independently selected from the group consisting of hydrogen; lower alkyl; alkenyl; aryl; arylalkyl, wherein arylalkyl is limited to benzyl, when R₁₉-R₂₀-R₂₁ represents an L-arginyl residue; (cycloalkyl)alkyl; aminoalkyl, wherein aryl and arylalkyl amines are excluded when R₁₉-R₂₀-R₂₁ represents an L-arginyl residue; amidoalkyl, wherein benzoyl amides and their heterocyclic variants are excluded when R₁₉-R₂₀-R₂₁ represents an L-arginyl residue; hydroxyalkyl; guanidinoalkyl; carboxyalkyl; (carboxyamido)alkyl, wherein aniline amides of aspartyl residues and heterocyclic variants are excluded when $R_{19}$-$R_{20}$-$R_{21}$ represents an L-arginyl residue; carboxyhydrazino)alkyl; ureidoalkyl; (heterocyclic)alkyl, wherein when $R_{19}$-$R_{20}$-$R_{21}$ represents an L-arginyl residue, then the heterocycle can only be separated by one methylene unit from the alpha-carbon; (thioalkoxy)alkyl; and sulfhydrylalkyl;

(aw) $R_{303}$ is independently selected from the group consisting of lower alkyl, arylalkyl, wherein arylalkyl is limited to benzyl when $R_{19}$-$R_{20}$-$R_{21}$ represents an L-arginyl residue, and (cycloalkyl)alkyl, with the proviso that $R_{303}$ may not be a vinyl group or have a heteroatom directly attached to the nitrogen or separated from it by one methylene unit;

(ax) $R_{304}$ is independently selected from the group consisting of hydrogen; lower alkyl; alkenyl; aryl, arylalkyl, wherein arylalkyl is excluded when $R_{19}$-$R_{20}$-$R_{21}$ represents an L-arginyl residue; (cycloalkyl)alkyl; aminoalkyl, wherein aryl and arylalkyl amines are excluded when $R_{19}$-$R_{20}$-$R_{21}$ represents an L-arginyl residue; amidoalkyl, wherein benzoyl amides and their heterocyclic variants are excluded when $R_{19}$-$R_{20}$-$R_{21}$ represents an L-arginyl residue; hydroxyalkyl; guanidinoalkyl; carboxyalkyl; (carboxyamido)alkyl, wherein aniline amides and heterocyclic variants are excluded when $R_{19}$-$R_{20}$-$R_{21}$ represents an L-arginyl residue; (carboxyhydrazino)alkyl; ureidoalkyl; (heterocyclic)alkyl, wherein (heterocyclic)alkyl is excluded when R $_{19}$-$R_{20}$-$R_{21}$ represents an L-arginyl residue; (thioalkoxy)alkyl; and sulfhydrylalkyl;

(ay) $R_{307}$ and $R_{317}$ are independently selected from hydrogen; lower alkyl; aryl and arylalkyl, wherein arylalkyl is excluded for $R_{307}$ and $R_{317}$ when $R_{19}$-$R_{20}$-$R_{21}$ and $R_{22}$-$R_{23}$-$R_{24}$ respectively represent an L-arginyl residue;

(az) $R_{310}$ is independently selected from the group consisting of hydrogen; lower alkyl; alkenyl; aryl; arylalkyl, wherein arylalkyl is limited to benzyl when $R_{22}$-$R_{23}$-$R_{24}$ represents an L-arginyl residue; (cycloalkyl)alkyl; aminoalkyl, aryl and arylalkyl amines are excluded when $R_{22}$-$R_{23}$-$R_{24}$ represents an L-arginyl residue; amidoalkyl, wherein benzoyl amides and their heterocyclic variants are excluded, when $R_{22}$-$R_{23}$-$R_{24}$ represents an L-arginyl residue; hydroxyalkyl; guanidinoalkyl; (carboxyamido)alkyl, wherein aniline amides of aspartyl residues and heterocyclic variants are excluded when $R_{22}$-$R_{23}$-$R_{24}$ represents an L-arginyl residue; (carboxyhydrazino)alkyl; ureidoalkyl; (heterocyclic)alkyl, wherein when $R_{22}$-$R_{23}$-$R_{24}$ represents an L-arginyl residue, then the heterocycle can only be separated by one methylene unit from the alpha-carbon; and sulfhydrylalkyl;

(ba) $R_{312}$ is independently selected from the group consisting of hydrogen; lower alkyl; alkenyl; aryl; arylalkyl, wherein arylalkyl is excluded when $R_{22}$-$R_{23}$-$R_{24}$ represents an L-arginyl residue; (cycloalkyl)alkyl; aminoalkyl, wherein aryl and arylalkyl amines are excluded when $R_{22}$-$R_{23}$-$R_{24}$ represents an L-arginyl residue; amidoalkyl, wherein benzoyl amides and their heterocyclic variants are excluded when $R_{22}$-$R_{23}$-$R_{24}$ represents an L-arginyl residue; hydroxyalkyl; guanidinoalkyl; carboxyalkyl; (carboxyamido)alkyl, wherein aniline amides and heterocyclic variants are excluded when $R_{22}$-$R_{23}$-$R_{24}$ represents an L-arginyl residue; (carboxyhydrazino)alkyl; ureidoalkyl; (heterocyclic)alkyl, wherein (heterocyclic)alkyl is excluded when $R_{22}$-$R_{23}$-$R_{24}$ represents an L-arginyl residue; (thioalkoxy)alkyl; and sulfhydrylalkyl;

(bb) $R_{315}$ and $R_{316}$ are independently selected from the group consisting of hydrogen, lower alkyl, arylalkyl, wherein arylalkyl is excluded when $R_{22}$-$R_{23}$-$R_{24}$ represents an L-arginyl residue, and (cycloalkyl)alkyl;

(bc) $R_{310}$ is is selected from the group consisting of hydrogen, lower alkyl, arylalkyl, alkenyl, (cycloalkyl)alkyl, aminoalkyl, and guanidinoalkyl;

(bd) $R_{325}$ and $R_{326}$ are independently selected from the group consisting of hydrogen, lower alkyl, aryl, arylalkyl, and (cycloalkyl)alkyl;

all of the foregoing with the provisos that (i) when more than one sulfhydrylalkyl is present in the compound, the compound exists in the oxidized disulfide form producing a cyclic molecule, or the two sulfhydryl moieties are connected by a $C_2$ to $C_8$ alkylene chain and (ii) when the compound contains a free amino group and carboxyl group, they can be cyclized to give the corresponding lactam.

2. A compound as defined by claim 1 wherein $R_5$ is selected from the group consisting of $>CR_{201}R_{202}$; $>NR_{203}$; $>C=CR_{205}R_{206}$, existing in the Z- or E-configuration; and substituted cyclopropyl of the formula

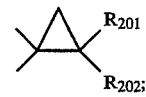

where $R_{201}$ is selected from the group consisting of aryl, arylalkyl, alkyl, and (cycloalkyl)alkyl;

$R_{202}$ and $R_{205}$ are selected from the group consisting of hydrogen and lower alkyl;

$R_{203}$ is arylalkyl; and $R_{206}$ is selected from aryl or arylalkyl.

3. A compound as defined by claim 1 wherein $R_8$ is selected from the group consisting of $>CR_{210}R_{211}$; $>NR_{213}$; $>C=CR_{215}R_{216}$, existing in either the Z- or E-configuration; and substituted cyclopropyl of the formula

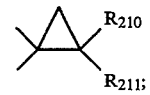

wherein $R_{210}$ is selected from the group consisting of arylalkyl; aminoalkyl; guanidinoalkyl; and lower alkyl;

$R_{211}$ and $R_{215}$ is selected from the group consisting of hydrogen and lower alkyl;

$R_{213}$ is selected from the group consisting of arylalkyl; aminoalkyl; guanidinoalkyl; and lower alkyl; with the proviso that $R_{213}$ may not have a heteroatom directly attached to the nitrogen or separated from it by one methylene unit; and $R_{216}$ is selected from arylalkyl or lower alkyl.

4. A compound as defined by claim 1 wherein $R_{17}$ is selected from the group consisting of $>CR_{301}R_{302}$; $>NR_{303}$; $>C=CR_{305}R_{306}$, existing in either the Z- or E -configuration; and substituted cyclopropyl of the formula

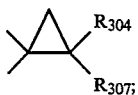

wherein
R$_{301}$ is selected from the group consisting of lower alkyl; arylalkyl, wherein arylalkyl is limited to benzyl when R$_{19}$-R$_{20}$-R$_{21}$ represents an L-arginyl residue; and (cycloalkyl)alkyl;

R$_{302}$, R$_{305}$ and R$_{307}$ are selected from the group consisting of hydrogen and lower alkyl;

R$_{303}$ is selected from the group consisting of hydrogen; lower alkyl; (cycloalkyl)alkyl; and arylalkyl, wherein arylalkyl is limited to benzyl when R$_{19}$-R$_{20}$-R$_{21}$ represents an L-arginyl residue;

R$_{304}$ is selected from the group consisting of lower alkyl; arylalkyl, wherein arylalkyl is excluded when R$_{19}$-R$_{20}$-R$_{21}$ represents an L-arginine residue; and (cycloalkyl)alkyl; and R$_{306}$ is selected from the group consisting of aryl; arylalkyl, wherein arylalkyl is excluded when R$_{19}$-R$_{20}$-R$_{21}$ represents an L-arginyl residue; lower alkyl; hydrogen; and (cycloalkyl)alkyl.

5. A compound as defined by claim 1 wherein R$_{20}$ is selected from the group consisting of >CR$_{310}$R$_{311}$; >C=CR$_{315}$R$_{316}$, existing in either the Z- or E- configuration; and substituted cyclopropyl of the formula

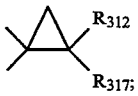

wherein
R$_{310}$ is selected from the group consisting of arylalkyl and guanidinoalkyl, wherein arylalkyl is limited to benzyl when R$_{22}$-R$_{23}$-R$_{24}$ represents an L-arginyl residue;

R$_{311}$, R$_{315}$ and R$_{317}$ are selected from the group consisting of hydrogen and lower alkyl;

R$_{312}$ is selected from the group consisting of arylalkyl and guanidinoalkyl, wherein arylalkyl is excluded when R$_{22}$-R$_{23}$-R$_{24}$ represents an L-arginine residue; and R$_{316}$ is selected from the group consisting of arylalkyl and aryl, wherein arylalkyl is excluded when R$_{22}$-R$_{23}$-R$_{24}$ represents an L-arginyl residue.

6. A compound as defined by claim 1 wherein when G and L are alpha amino acid residues, the preferred chirality of R$_{14}$ and R$_{20}$ is of the D- or unnatural configuration.

7. A compound as defined by claim 1 wherein R$_1$-R$_2$-R$_3$, taken together is selected from the group consisting of hydrogen, acetyl and lower alkyl.

8. A compound as defined by claim 1 wherein R$_4$, R$_7$, R$_{10}$, R$_{13}$, R$_{16}$, R$_{19}$, and R$_{22}$ are independently selected from the group consisting of >NH and >N-(lower alkyl).

9. A compound as defined by claim 1 wherein R$_6$, R$_9$, R$_{12}$, R$_{15}$, R$_{18}$, R$_{21}$, and R$_{24}$ are independently selected from the group consisting of >C=O and >CH$_2$.

10. A compound as defined by claim 1 selected from the group consisting of:

H-Phenylalanyl-Lysyl-{3-Aminomethylbenzoyl}-{(2R/S)-2-Amino-5-phenylpentanoyl}-DArginyl-OH;

H-Phenylalanyl-Lysyl-{3-Aminomethylbenzoyl}-{(2S)-2-Amino-3-cyclohexylpropanoyl}-DArginyl-OH;

(N-Methyl)Phenylalanyl-Lysyl-Prolyl-Ψ{CH$_2$NH}-{(2R)-2-Amino-3-cyclohexylpropanoyl}-{(2S)-2-Amino-3-cyclohexylpropanoyl }-DArginyl-OH;

(N-Methyl)Phenylalanyl-Lysyl-Sarcosyl-D{1-Naphthylalanyl}-{(2S)-2-Amino-3-cyclohexylpropanoyl}-DArginyl-OH;

(N-Methyl)Phenylalanyl-Lysyl-{(N-Methyl)[(2R/S)-2-Benzyl-4-aminobutanoyl]}-Phenylalanyl-DArginyl-OH;

{(N-[(3'R/S)-3'-Methylamino-3'-phenylpropyl])Lysyl-Prolyl-{(2R)-2-Amino-3-cyclohexylpropanoyl}-Phenylalanyl-DArginyl-OH;

(N-Methyl)Phenylalanyl-Lysyl-{(N-Methyl)[(2R/S)-2-Cyclohexylmethyl-6-aminohexanoyl ]}-Phenylalanyl-DArginyl-OH;

(N-Methyl)Phenylalanyl-Lysyl-Prolyl-Ψ{CH$_2$NH}-(2R)-2-Amino-3-cyclohexylpropanoyl}-Phenylalanyl-DArginyl-OH;

{(N-[(3'R/S)-3'-Amino-3'-phenylpropyl])Lysyl-Prolyl-{(2R)-2-Amino-3-cyclohexylpropanoyl}-Phenylalanyl-DArginyl-OH;

(N-Methyl)Phenylalanyl-Lysyl-{(N-Methyl)[(2R/S)-2-Benzyl-6-aminohexanoyl}-Phenylalanyl-DArginyl-OH;

(N-Methyl)Phenylalanyl-Lysyl-Prolyl-D {1-Naphthylalanyl}-Phenylalanyl-{(3R)-3-amino-7-guanidinohexanoyl}-OH;

(N-Methyl)Phenylalanyl-Lysyl-Prolyl-D{1-Naphthylalanyl}-{1-Naphthylalanyl}-{(3R)-3-amino-7-guanidinohexanoyl-OH;

(N-Methyl)Phenylalanyl-Lysyl-Prolyl-Ψ(CH$_2$NH)-{(2R)-2-Amino-3-cyclohexylpropanoyl}-{(2S)-2-Amino-3-cyclohexylpropanoyl}-DPhenylalanyl-OH; and (N-Methyl)Phenyl-Lysyl-Prolyl-Ψ(CH$_2$-NH)-{(2R)-2-Amino-3-cyclohexylpropanoyl}-Phenylalanyl-DPhenylalanyl-OH.

11. A compound as defined by claim 1 wherein R$_{13}$-R$_{14}$-R$_{15}$ taken together is {(2R)-2-amino-3-cyclohexylpropanoyl} is selected from the group consisting of:

(N-Methyl)Phenylalanyl-Lysyl-Prolyl-{(2R)-2-Amino-3-cyclohexylpropanoyl}-Phenylalanyl-Ψ(CH$_2$NH)-DArginyl-OH;

(N-Methyl)Phenylalanyl-Lysyl-Prolyl-{(2R)-2-Amino-3-cyclohexylpropanoyl}-Phenylalanyl-{(3R)-3-Amino-7-guanidino-hexanoyl}-OH;

(N-Methyl)Phenylalanyl-Lysyl-Sarcosyl-{(2R)-2-Amino-3-cyclohexylpropanoyl}-Phenylalanyl-DArginyl-OH;

(N-Methyl)Phenylalanyl-Lysyl-(N-Methyl)Alanyl-{(2R)-2-Amino-3-cyclohexylpropanoyl}-Phenylalanyl-DArginyl-OH;

H-Phenylalanyl-Lysyl-{2-[(2'S) Pyrrolidinyl]acetyl}-{(2R)-2-Amino-3-cyclohexylpropanoyl}-Phenylalanyl-DArginyl-OH;

(N-Methyl)Phenylalanyl-Lysyl-Prolyl-{(2R)-2-Amino-3-cyclohexylpropanoyl}-Phenylalanyl-Ψ{(R/S)CH(CH$_3$)NH}-Arginyl-OH;

(N-Methyl)Phenylalanyl-Lysyl-Prolyl-{(2R)-2-Amino-3-cyclohexylpropanoyl}-{1-Naphthylalanyl}-{(3R)-3-amino-7-guanidinohexanoyl}-OH;

(N-Methyl)Phenylalanyl-Lysyl-{(2R/S)-2-
Methylamino-5-phenylpentanoyl }-{(2R)-2-Amino-3-
cyclohexylpropanoyl}-Phenylalanyl-DArginyl-OH;
and H-Phenylalanyl-Lysyl-Alanyl-{(2R)-2-Amino-3-
cyclohexylpropanoyl}-{(N-Methyl)(2S)-2-Amino-3-
cyclohexylpropanoyl}-DArginyl-OH.

12. A compound as defined by claim 1 wherein $R_{13}$-$R_{14}$-$R_{15}$ taken together is {(2R)-2-amino-3-cyclohexyl-propanoyl} and $R_{16}$-$R_{17}$-$R_{18}$ taken together is {(2S)-2-amino-3-cyclohexylpropanoyl} is selected from the group consisting of:

H-Phenylalanyl-Lysyl-{(3R/S)-1,2,3, 4-Tetrahydroisoquinolin-3-carbonyl}-{(2R)-2-Amino-3-
cyclohexylpropanoyl}-{(2S)-2-Amino-3-cyclohexyl-
propanoyl}-DArginyl-OH;

(N-Allyl)Phenylalanyl-Lysyl-(N-Methyl)Alanyl-{(2R)-
2-Amino-3-cyclohexylpropanoyl}-{(2S)-2-Amino-3-
cyclohexylpropanoyl}-DArginyl-OH;

(N,N-Dimethyl)Phenylalanyl-Lysyl-(N-Methyl)Alanyl-{(2R)-2-Amino-3-cyclohexylpropanoyl}-{(2S)-2-
Amino-3-cyclohexylpropanoyl}-DArginyl-OH;

N-Acetyl-Phenylalanyl-Lysyl-(N-Methyl)Alanyl-
{(2R)-2-Amino-3-cyclohexylpropanoyl}-{(2S)-2-
Amino-3-cyclohexylpropanoyl}-DArginyl-OH;

(N-Methyl)Phenylalanyl-Lysyl-{(2S)-Azetidine-2-carbonyl}-{(2R)-2-Amino-3-cyclohexylpropanoyl}-
{(2S)-2-Amino-3-cyclohexylpropanoyl}-DArginyl-OH;

(N-Methyl)Phenylalanyl-Norleucyl-(N-Methyl)Alanyl-
{(2R)-2-Amino-3-cyclohexylpropanoyl}-{(2S)-2-
Amino-3-cyclohexylpropanoyl}-DArginyl-OH;

H-Phenylalanyl-(N-alpha-Methyl)Lysyl-Prolyl-{(2R)-
2-Amino-3-cyclohexylpropanoyl}-{(2S)-2-Amino-3-
cyclohexylpropanoyl}-DArginyl-OH;

(N-Methyl)Phenylalanyl-Lysyl-Prolyl-{(2R)-2-Amino-
3-cyclohexylpropanoyl}-{(2S)-2-Amino-3-cyclohex-
ylpropanoyl}-(N-Methyl)Arginyl-OH;

(N-Methyl)Phenylalanyl-(N-alpha,N-epsilon,Dimethyl)Lysyl-Prolyl-{(2R)-2-Amino-3-cyclohexyl-
propanoyl}-{(2S)-2-Amino-3-cyclohexylpropanoyl}-
DArginyl-OH;

(N-Methyl)Phenylalanyl-Lysyl-(N-Methyl)Alanyl-
{(2R)-2-Amino-3-cyclohexylpropanoyl}-{(2S)-2-
Amino-3-cyclohexylpropanoyl}-DArginyl-OH;

(N-Ethyl)Phenylalanyl-Lysyl-(N-Methyl)Alanyl-
{(2R)-2-Amino-3-cyclohexylpropanoyl}-{(2S)-2-
Amino-3-cyclohexylpropanoyl}-DArginyl-OH;

H-Phenylalanyl-Lysyl-(N-Methyl)Alanyl-{(2R)-2-
Amino-3-cyclohexylpropanoyl}-{(2S)-2-Amino-3-
cyclohexylpropanoyl}-DArginyl-OH;

H-Phenylalanyl-Lysyl-{(2S)-Azetidine-2-carbonyl}-
{(2R)-2-Amino-3-cyclohexylpropanoyl}-{(2S)-2-
Amino-3-cyclohexylpropanoyl}-DArginyl-OH;

(N-Isopropyl)Phenylalanyl-Lysyl-(N-Methyl)Alanyl-
{(2R)-2(N,N-Diethyl)Phenylalanyl-Lysyl-(N-
Methyl)Alanyl-{(2R)-2-Amino-3-cyclohexyl-
propanoyl}-{(2S)-2-Amino-3-cyclohexylpropanoyl}-
DArginyl-OH;

H-Phenylalanyl-Norleucyl-(N-Methyl)Alanyl-{(2R)-2-
Amino-3-cyclohexylpropanoyl}-{(2S)-2-Amino-3-
cyclohexylpropanoyl}-DArginyl-OH;

H-Phenylalanyl-Lysyl-Sarcosyl-{(2R)-2-Amino-3-
cyclohexylpropanoyl}-{(2S)-2-Amino-3-cyclohexyl-
propanoyl}-DArginyl-OH;

(N-Methyl)Phenylalanyl-Lysyl-{(2R)-3,3-Dimethyl-
thiazolidine-2-carbonyl}-{(2R)-2-Amino-3-cyclohex-
ylpropanoyl}-{(2S)-2-Amino-3-cyclohexyl-
propanoyl}-DArginyl-OH;

(N-Methyl)Phenylalanyl-Lysyl-(N-Methyl)Phenylalanyl-{(2R)-2-Amino-3-cyclohexylpropanoyl}-{(2S)-2-
Amino-3-cyclohexylpropanoyl}-DArginyl-OH; and (N-Methyl)Phenylalanyl-Lysyl-D(N-Methyl)Alanyl-
{(2R)-2-Amino-3-cyclohexylpropanoyl}-{(2S)-2-
Amino-3-cyclohexylpropanoyl}-DArginyl-OH.

13. A compound as defined by claim 1 wherein $R_{12}$-$R_{13}$ taken together is $\Psi(CH_2-NH-)$ and $R_{16}$-$R_{17}$-$R_{18}$ taken together is {(2R)-2-amino-3-cyclohexyl-propanoyl} is selected from the group consisting of:

H-Vinylgylcyl-Lysyl-Prolyl-$\Psi\{CH_2$-NH$\}$-{(2R)-2-
Amino-3-cyclohexylpropanoyl}-{(2S)-2-Amino-3-
cyclohexylpropanoyl}-DArginyl-OH;

H-Lysyl(N-epsilon-acetyl)-Lysyl-Prolyl-
$\Psi\{CH_2-NH\}$-{(2R)-2-Amino-3-cyclohexyl-
propanoyl}-{(2S)-2-Amino-3-cyclohexylpropanoyl}-
DArginyl-OH;

H-Seryl-Lysyl-Prolyl-$\Psi\{CH_2\text{-NH}\}$-{(2R)-2-Amino-3-
cyclohexylpropanoyl}-{(2S)-2-Amino-3-cyclohexyl-
propanoyl}-DArginyl-OH;

H-Glutamyl-Lysyl-Prolyl-$\Psi\{CH_2-NH\}$-{(2R)-2-
Amino-3-cyclohexylpropanoyl}-{(2S)-2-Amino-3-
cyclohexylpropanoyl}-DArginyl-OH;

H-Glutaminyl-Lysyl-Prolyl-$\Psi\{CH_2-NH\}$-{(2R)-2-
Amino-3-cyclohexylpropanoyl}-{(2S)-2-Amino-3-
cyclohexylpropanoyl}-DArginyl-OH;

H-Glutamyl (gamma-NHNH$_2$)-Lysyl-Prolyl-
$\Psi\{CH_2-NH\}$-{(2R)-2-Amino-3-cyclohexyl-
propanoyl}-{(2S)-2-Amino-3-cyclohexylpropanoyl}-
DArginyl-OH;

H-Citrullyl-Lysyl-Prolyl-$\Psi\{CH_2-NH\}$-{(2R)-2-
Amino-3-cyclohexylpropanoyl}-{(2S)-2-Amino-3-
cyclohexylpropanoyl}-DArginyl-OH;

H-(S-Benzyl)Cysteinyl-Lysyl-prolyl-$\Psi\{CH_2-NH\}$-
{(2R)-2-Amino-3-cyclohexylpropanoyl}-{(2S)-2-
Amino-3-cyclohexylpropanoyl}-DArginyl-OH;

H-Methionyl-Lysyl-Prolyl-$\Psi\{CH_2-NH\}$-{(2R)-2-
Amino-3-cyclohexylpropanoyl}-{(2S)-2-Amino-3-
cyclohexylpropanoyl}-DArginyl-OH;

H-(S-aminomethyl)Cysteinyl-Lysyl-Prolyl-
$\Psi\{CH_2-NH\}$-{(2R)-2-Amino-3-cyclohexyl-
propanoyl}-{(2S)-2-Amino-3-cyclohexylpropanoyl}-
DArginyl-OH;

H-{(2R)-2-amino-3-chloropropanoyl )-Lysyl-Prolyl-
$\Psi\{CH_2-NH\}$-{(2R)-2-Amino-3-cyclohexyl-
propanoyl}-{(2S)-2-Amino-3-cyclohexylpropanoyl}-
DArginyl-OH;

{2-Acetamido-3-phenylacryloyl}-Lysyl-Prolyl-
$\Psi\{CH_2-NH\}$-{(2R)-2-Amino-3-cyclohexyl-
propanoyl}-{(2S)-2-Amino-3-cyclohexylpropanoyl}-
DArginyl-OH;

(N-Methyl)Phenylglycyl-Lysyl-Prolyl-$\Psi\{CH_2-NH\}$-
{(2R)-2-Amino-3-cyclohexylpropanoyl}-{(2S)-2-
Amino-3-cyclohexylpropanoyl}-DArginyl-OH;

(N-Methyl)Phenylalanyl-Lysyl-Prolyl-$\Psi\{CH_2-NH\}$-
{(2R)-2-Amino-3-cyclohexylpropanoyl}-Aza-
phenylalanyl-DArginyl-OH;

(N-Methyl)Phenylalanyl-Lysyl-Azaglycyl-
$\Psi\{CH_2-NH\}$-{(2R)-2-Amino-3-cyclohexyl-
propanoyl}-{(2S)-2-Amino-3-cyclohexylpropanoyl}-
DArginyl-OH;

(N-Methyl)Phenylalanyl-Lysyl-Prolyl-$\Psi(CH_2NH)$-
{(2R)-2-Amino-3-cyclohexylpropanoyl}-{(2S)-2-
Amino-3-cyclohexylpropanoyl}-DPhenylalanyl-OH;
and (N-Methyl)Phenyl-Lysyl-Prolyl-Ψ(CH₂—NH)-{(2R)-2-Amino-3-cyclohexylpropanoyl}-Phenylalanyl-DPhenylalanyl-OH.

14. A compound as defined by claim 1 wherein $R_1$-$R_2$-$R_3$ taken together as a group is methyl; $R_4$-$R_5$-$R_6$ taken together as a group is L-phenylalanine; and $R_7$-$R_8$-$R_9$ taken together is L-lysine is selected from the group consisting of:

(N-Methyl)Phenylalanyl-Lysyl-Glycyl-Ψ{S(O₂)-NH}-{(2R)-2-Amino-3-cyclohexylpropanoyl}-{(2S)-2-Amino-3-cyclohexylpropanoyl}-Ψ{CH₂-NH}-DArginyl-OH;

(N-Methyl)Phenylalanyl-Lysyl-Prolyl-Ψ{C≡C}-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-Ψ{C(=S)—NH}-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-Ψ{CH₂-O}-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-Ψ{CH₂—S}-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Ψ{C(=O)—S}-Glycyl-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Ψ{CH₂C(=O)—S}-Glycyl-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Ψ{CH=CH}-Glycyl-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-Ψ{C(=O)—CH₂-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-Ψ{CH(OH)—CH₂}-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-Ψ{C(=CH₂)—CH₂}-{(2R)-2-Amino-3-cyclohexylpropanoyl}-{(2S)-2-Amino-3-cyclohexylpropanoyl}-DArginyl-OH; (N-Methyl)Phenylalanyl-Lysyl-Ψ{C(=O)-N(OMe)}-Glycyl{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-Ψ{PO(OH)—NH}-{(2R)-2-Amino-3-cyclohexylpropanoyl}-{(2S)-2-Amino-3-cyclohexylpropanoyl}-DArglnyl-OH;

(N-Methyl)Phenylalanyl-Lysyl-Prolyl-Ψ{PO(OMe)—NH}-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-Ψ{PO(NHMe)—NH}-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-Ψ{PO(NMe₂)—NH}-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-Ψ{PO(NH₂)—NH}-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Ψ{CH₂C(=O)—O}-Glycyl-{(2R)-2-Amino-3-cyclohexylpropanoyl}-{(2S)-2-Amino-3-cyclohexyl-propanoyl}-DArginyl-OH; and (N-Methyl)Phenylalanyl-Lysyl-Prolyl-{(2R)-2-Amino-3-cyclohexylpropanoyl}-{(2S)-2-Amino-3-cyclohexylpropanoyl}-Ψ{CH₂—N(CH₂CH₂C₆H₅)}-DArginyl-OH.

* * * * *

UNITED STATES PATENT AND TRADEMARK OFFICE
CERTIFICATE OF CORRECTION

PATENT NO.  : 5,387,671　　　　　　　　　　　　　　Page 1 of 2
DATED　　　 : February 7, 1995
INVENTOR(S) : Megumi Kawai; Paul Wiedeman; Jay R. Luly; Yat S. Or It is certified that error appears in the above-indentified patent and that said Letters Patent is hereby corrected as shown below:

COLUMN 3, LINE 34:　　　delete "$CR_{201}R_{202}$,"
　　　　　　　　　　　　　insert -->$CR_{201}R_{202}$,—

COLUMN 7, LINE 35:　　　delete "$R_{16}$; and"
　　　　　　　　　　　　　insert --$R_{16}$; $R_{18}$ and $R_{19}$;--

COLUMN 7, LINE 57:　　　delete "rep,resent" and insert --represent--

COLUMN 17, LINE 67:　　　delete "{(1-Naphthylalanyl- "

COLUMN 29, LINE 57:　　　delete "(Sequence ID NO. 1)"

COLUMN 32, LINE 26:　　　delete "(Sequence ID NO. 2)"

UNITED STATES PATENT AND TRADEMARK OFFICE
CERTIFICATE OF CORRECTION

PATENT NO. : 5,387,671
DATED : February 7, 1995
INVENTOR(S) : Megumi Kawai, et al.

It is certified that error appears in the above-indentified patent and that said Letters Patent is hereby corrected as shown below:

COLUMN 53, LINE 35:  delete "0.18 mole"
insert --0.18 mmole--

Signed and Sealed this

Twenty-third Day of January, 1996

Attest:

BRUCE LEHMAN

Attesting Officer  Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 6 amino acids
( B ) TYPE: amino acid (C) STRANDEDNESS: single
(D) TOPOLOGY: linear (ii) MOLECULE TYPE: peptide (ix) FEATURE:
  (A) NAME/KEY: Modified-site
  (B) LOCATION: 2
  (D) OTHER INFORMATION: /note="XAA at position 2 is a 6- aminohexanoyl residue"

(xi) SEQUENCE DESCRIPTION: SEQ ID NO:1:

His Xaa Gln Leu Gly Arg
1               5

(2) INFORMATION FOR SEQ ID NO:2:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="XAA at position 1 is an N- methylphenylalanyl residue"

(ix) FEATURE:
    (A) NAME/KEY: Modified-site
    (B) LOCATION: 4
    (D) OTHER INFORMATION: /note="XAA at position 4 is an L- cyclohexylalanyl residue"

(ix) FEATURE:
    (A) NAME/KEY: Modified-site
    (B) LOCATION: 6
    (D) OTHER INFORMATION: /note="XAA at position 6 is an N- methylalanyl residue"

(xi) SEQUENCE DESCRIPTION: SEQ ID NO:2:

Xaa Lys Ala Xaa Ala Xaa Arg
1               5